United States Patent
Nakao et al.

(10) Patent No.: US 8,598,212 B2
(45) Date of Patent: Dec. 3, 2013

(54) THERAPEUTIC AGENT AND PREVENTATIVE AGENT FOR ALZHEIMER'S DISEASE

(75) Inventors: Kaoru Nakao, Kamakura (JP); Yohei Miyamoto, Kamakura (JP); Naohiro Yamada, Urayasu (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 13/643,742

(22) PCT Filed: Apr. 28, 2011

(86) PCT No.: PCT/JP2011/060355
§ 371 (c)(1),
(2), (4) Date: Oct. 26, 2012

(87) PCT Pub. No.: WO2011/136318
PCT Pub. Date: Nov. 3, 2011

(65) Prior Publication Data
US 2013/0041158 A1    Feb. 14, 2013

(30) Foreign Application Priority Data
Apr. 28, 2010   (JP) .................... 2010-103246

(51) Int. Cl.
A61K 31/4427   (2006.01)
A61K 31/426    (2006.01)
A61K 31/421    (2006.01)
A61K 31/415    (2006.01)
C07D 401/02    (2006.01)
C07D 277/20    (2006.01)
C07D 263/30    (2006.01)
C07D 231/10    (2006.01)

(52) U.S. Cl.
USPC ........ 514/341; 546/275.4; 548/202; 548/235; 548/377.1; 514/365; 514/374; 514/406

(58) Field of Classification Search
USPC ............... 514/341, 365, 374, 406; 546/275.4; 548/202, 235, 377.1
See application file for complete search history.

(56) References Cited

U.S. PATENT DOCUMENTS 8,247,569 B2 *   8/2012   Morita et al. .............. 546/275.4
8,349,874 B2 *   1/2013   Morita et al. ................. 514/341

FOREIGN PATENT DOCUMENTS

| WO | 00/7996 A2 | 2/2000 |
| WO | 00/66562 A1 | 11/2000 |
| WO | 01/01986 | 1/2001 |
| WO | 02/051442 A1 | 7/2002 |
| WO | 2004/014367 | 2/2004 |
| WO | 2008/105383 A1 | 9/2008 |
| WO | 2010/050577 | 5/2010 |

OTHER PUBLICATIONS

Lah, J.J. et al. "Biology of Alzheimer's Disease," *The American Psychiatric Publishing*, (textbook of psychopharmacology), 2009, Chapter 48, pp. 793-794.

Tune, L.E., "Management of Noncognitive Symptoms of Dementia," *The American Psychiatric Publishing*, (textbook of psychopharmacology), 2009, Chapter 56, pp. 935-936.

Martin, R. et al., "Sequential Copper-Catalyzed Vinylation/Cyclization: An Efficient Synthesis of Functionalized Oxazoles," *Organic Letters*, 2007, vol. 9, No. 26, pp. 5521-5524.

* cited by examiner

*Primary Examiner* — Samantha Shterengarts
(74) *Attorney, Agent, or Firm* — DLA Piper LLP (US)

(57) ABSTRACT

A therapeutic agent or prophylactic agent for Alzheimer's disease has an effect to inhibit or delay the progress of Alzheimer's disease and exhibits a long-lasting therapeutic effect on Alzheimer's disease even when used for a long period of time. The therapeutic agent or prophylactic agent for Alzheimer's disease includes as an effective ingredient a cyclohexane derivative exemplified by the formula below, or a pharmaceutically acceptable salt thereof or a prodrug thereof.

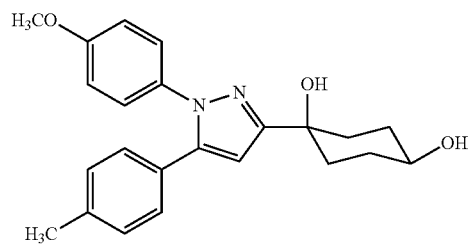

11 Claims, 1 Drawing Sheet

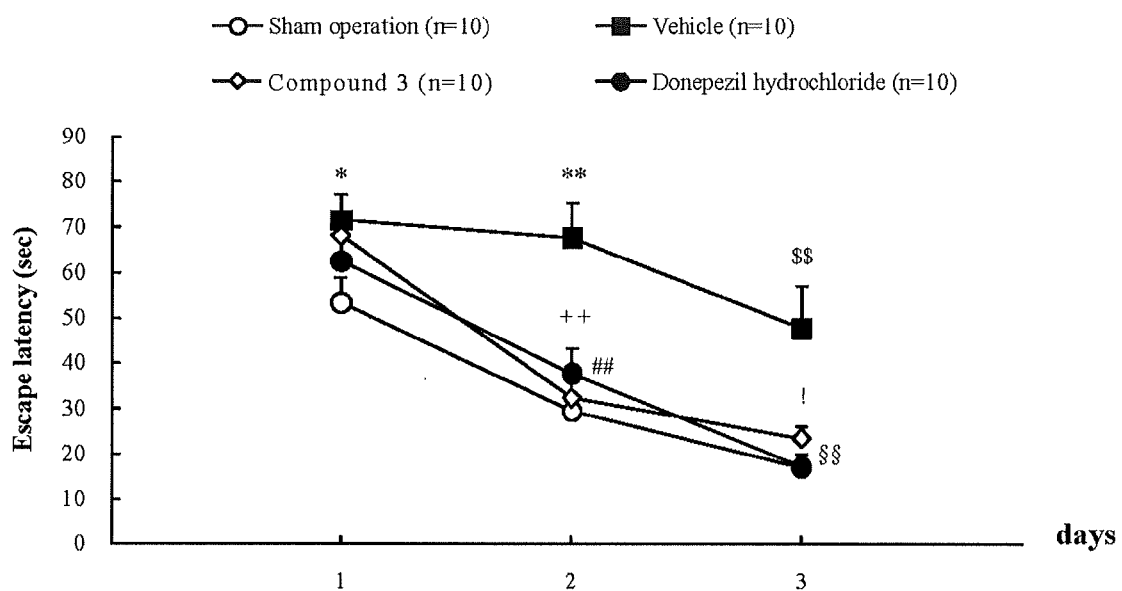

THERAPEUTIC AGENT AND PREVENTATIVE AGENT FOR ALZHEIMER'S DISEASE

RELATED APPLICATIONS

This is a §371 of International Application No. PCT/JP2011/060355, with an international filing date of Apr. 28, 2011 (WO 2011/136318 A1, published Nov. 3, 2011), which is based on Japanese Patent Application No. 2010-103246, filed Apr. 28, 2010, the subject matter of which is incorporated herein by reference.

TECHNICAL FIELD

This disclosure relates to a therapeutic agent or prophylactic agent for Alzheimer's disease.

BACKGROUND

Alzheimer's disease is a disease characterized by senile plaques, β-amyloid deposits, and neurofibrillary tangles in the cerebral cortex and subcortical gray matter. Its main symptom is progressive cognitive deterioration (hereinafter "dementia") and, in addition to this symptom, depression, schizophrenia-like symptoms (such as delusions and hallucinations), agitation, aggressive behaviors, and so-called apathy, which is an enervation-like symptom, are also known to occur (Schatzberg et al., "Seishin Shinkei Yakurigagu Daijiten," Nishimura Shoten, 2009, p. 785). The incidence rate of Alzheimer's disease is increased with age, and it is said that, in people aged 85 years or older, the rate reaches as high as 40% or more. Therefore, in aging societies such as Japan, it is an urgent task to develop a therapeutic agent for Alzheimer's disease.

At present, donepezil, rivastigmine, galantamine and tacrine, which are inhibitors of cholinesterase, an acetylcholine-degrading enzyme, have been used as a therapeutic agent or a prophylactic agent for dementia caused by Alzheimer's disease. In addition, memantine, which is an N-methyl-D-aspartate (hereinafter "NMDA") receptor antagonist, has been used in Europe and the U.S. (Miller et al., Geriatr Nurs, 2004, Vol. 25, p. 56).

Some of the existing therapeutic agents for Alzheimer's disease have been reported to have an analgesic effect on neuropathic pain. For example, it has been reported that donepezil exhibits an analgesic effect on a rat neuropathic pain model (Clayton et al., Anesthesiology, 2007, Vol. 106, p. 1010). In addition, it has been reported that memantine exhibits an analgesic effect on a rat diabetic neuropathic pain model (Chen et al., Neuropharmacoogy, 2009, Vol. 57, p. 121) and also exhibits an analgesic effect on patients with complex regional pain syndrome which is one of neuropathic pains (Sinia et al., Clin J Pain, 2007, Vol. 23, p. 273).

On the other hand, although there are reports suggesting that a pyrazole derivative of the following Formula which is characterized by having the sulfonyl group on the aromatic ring (WO 00/066562) and a pyrazole derivative which acts on estrogen receptors (WO 00/007996) are effective in treating Alzheimer's disease, such effectiveness of a cyclohexane derivative is not disclosed nor suggest at all.

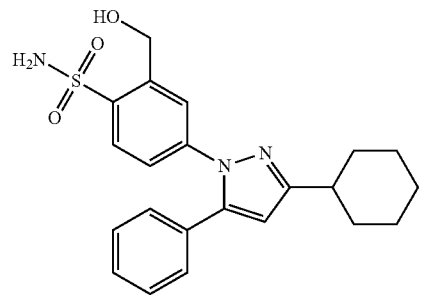

In addition, although a pyrazole derivative that is effective as an analgesic or a therapeutic agent for neuropathic pain has been known (WO 08/105,383), there are no reports about its therapeutic effect on Alzheimer's disease.

However, there is concern that cholinesterase inhibitors, which are the existing therapeutic agents for Alzheimer's disease, may produce side effects on autonomically innervated organs such as heart and intestine and, therefore, the dose thereof is restricted (Schatzberg et al. eds., "Seishin Shinkei Yakurigagu Daijiten," Nishimura Shoten, 2009, p. 669). Hence, a sufficient therapeutic effect against Alzheimer's disease cannot be obtained and, moreover, the therapeutic effect tends to be reduced if they are used continually.

Accordingly, it could be helpful to provide a therapeutic agent and a prophylactic agent for Alzheimer's disease which have an effect to inhibit or delay the progress of Alzheimer's disease and whose therapeutic effect against Alzheimer's disease last for a long time even when used for a long period of time.

SUMMARY

We discovered novel cyclohexane derivatives having an excellent analgesic effect on neuropathic pain and also excellent therapeutic and prophylactic effects against Alzheimer's disease.

That is, we provide a therapeutic agent or prophylactic agent for Alzheimer's disease, the agent comprising as an effective ingredient a cyclohexane derivative represented by Formula (I):

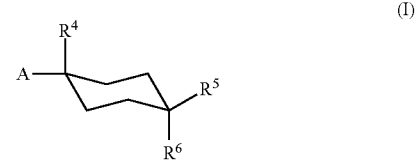

or a pharmaceutically acceptable salt thereof or a prodrug thereof, wherein A is a substituent represented by Formula (IIa) or (IIb):

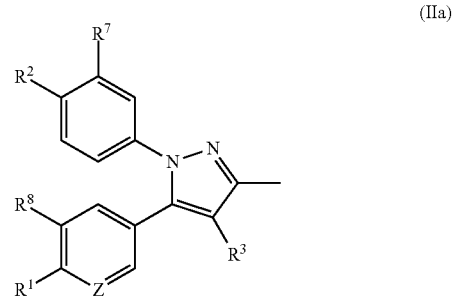

(IIb)

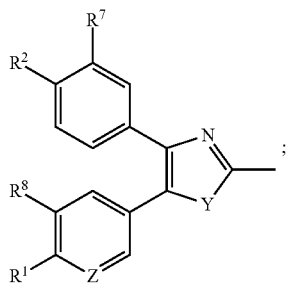

$R^1$ and $R^2$ are each independently a hydrogen atom, chlorine atom, $C_1$-$C_3$ haloalkyl group, $C_1$-$C_4$ alkyl group or a $C_1$-$C_4$ alkoxy group; $R^3$ is a hydrogen atom or a chlorine atom; $R^4$ is a fluorine atom, hydroxymethyl group or a hydroxyl group; $R^5$ and $R^6$ are each independently a hydrogen atom, fluorine atom, $C_1$-$C_3$ haloalkyl group, carboxyl group, methoxycarbonyl group, ethoxycarbonyl group, $C_1$-$C_4$ alkoxy group, hydroxyl group or a $C_2$-$C_5$ alkylcarbonyloxy group, or optionally together form an oxo group; $R^7$ and $R^8$ are each independently a hydrogen atom or a fluorine atom; Y is an oxygen atom or a sulfur atom; Z is a nitrogen atom or a methine group.

In the above-described cyclohexane derivative, it is preferred that $R^1$ and $R^2$ be each independently a trifluoromethyl group, methyl group or a methoxy group, and it is more preferred that $R^3$ be a hydrogen atom; $R^4$ be a hydroxymethyl group or a hydroxyl group; $R^5$ and $R^6$ be each independently a hydrogen atom, fluorine atom, trifluoromethyl group, carboxyl group, methoxy group, hydroxyl group or an acetyloxy group (or may optionally together form an oxo group).

The cyclohexane derivative or a pharmaceutically acceptable salt thereof or a prodrug thereof has an effect to inhibit or delay the progress of Alzheimer's disease, and has a property to exhibit a long-lasting therapeutic effect against Alzheimer's disease even when used for a long period of time.

BRIEF DESCRIPTION OF THE DRAWING

FIG. 1 shows the effect of the cyclohexane derivative on Alzheimer's disease model rats (oral administration).

DETAILED DESCRIPTION

Our cyclohexane derivative is characterized in that it is a compound represented by Formula (I):

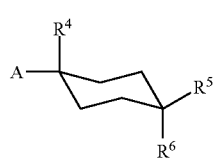

(I)

wherein A is a substituent represented by the following Formula (IIa) or (IIb):

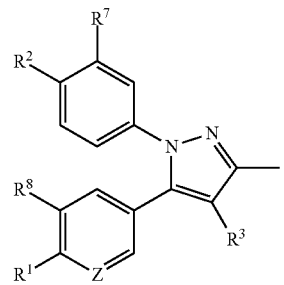

(IIa)

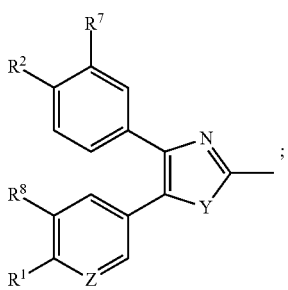

(IIb)

$R^1$ and $R^2$ are each independently a hydrogen atom, a chlorine atom, a $C_1$-$C_3$ haloalkyl group, a $C_1$-$C_4$ alkyl group or a $C_1$-$C_4$ alkoxy group; $R^3$ is a hydrogen atom or a chlorine atom; $R^4$ is a fluorine atom, a hydroxymethyl group or a hydroxyl group; $R^5$ and $R^6$ are each independently a hydrogen atom, a fluorine atom, a $C_1$-$C_3$ haloalkyl group, a carboxyl group, a methoxycarbonyl group, an ethoxycarbonyl group, a $C_1$-$C_4$ alkoxy group, a hydroxyl group or a $C_2$-$C_5$ alkylcarbonyloxy group, or $R^5$ and $R^6$ may optionally together form an oxo group; $R^7$ and $R^8$ are each independently a hydrogen atom or a fluorine atom; Y is an oxygen atom or a sulfur atom; and Z is a nitrogen atom or a methine group,
or a pharmaceutically acceptable salt thereof or a prodrug thereof.

The term "$C_1$-$C_4$ alkyl group" means a linear, branched or cyclic alkyl group having 1 to 4 carbon atoms, and examples thereof include a methyl group, an ethyl group, an n-propyl group, an isopropyl group, a cyclopropyl group, a cyclopropylmethyl group, an n-butyl group, a sec-butyl group and a tert-butyl group.

The term "$C_1$-$C_4$ alkoxy group" means a linear, branched or cyclic alkyl-oxy group having 1 to 4 carbon atoms, and examples thereof include a methoxy group, an ethoxy group, an n-propyloxy group, an isopropyloxy group, a cyclopropyloxy group, an n-butoxy group, a sec-butoxy group and a tert-butoxy group.

The term "$C_1$-$C_3$ haloalkyl group" means a linear alkyl group having 1 to 3 carbon atoms wherein a part or all of the hydrogen atoms on the group are replaced by a halogen atom(s) (the halogen atom means a fluorine atom, a chlorine atom, a bromine atom or an iodine atom), and examples thereof include a monochloromethyl group, a monofluoromethyl group, a difluoromethyl group, a trifluoromethyl group, a trichloromethyl group and a pentafluoroethyl group.

Examples of the "$C_2$-$C_5$ alkylcarbonyloxy group" include an acetyloxy group, an ethanoyloxy group, a propanoyloxy group, an isopropanoyloxy group, a butanoyloxy group and an isobutanoyloxy group and a pivaloyloxy group.

In Formula (I), A is preferably Formula (IIa); Y is preferably an oxygen atom; and Z is preferably a methine group.

$R^1$ is preferably a hydrogen atom, a chlorine atom, a trifluoromethyl group, a methyl group, an ethyl group, an n-propyl group, an isopropyl group, a methoxy group, an ethoxy group, an n-propyloxy group or an isopropyloxy group, more preferably a trifluoromethyl group, a methyl group or a methoxy group, and still more preferably a methyl group.

$R^2$ is preferably a hydrogen atom, a chlorine atom, a trifluoromethyl group, a methyl group, an ethyl group, an n-propyl group, an isopropyl group, a methoxy group, an ethoxy group, an n-propyloxy group or an isopropyloxy group, and more preferably a methoxy group.

$R^3$ is preferably a hydrogen atom; and $R^4$ is preferably a hydroxymethyl group or a hydroxyl group, and more preferably a hydroxyl group.

$R^5$ is preferably a hydrogen atom, a fluorine atom, a trifluoromethyl group, a carboxyl group, a methoxy group, an ethoxy group, an n-propyloxy group, an isopropyloxy group, a hydroxyl group, an acetyloxy group, a propanoyloxy group, a butanoyloxy group or an isobutanoyloxy group, more preferably a hydrogen atom, a hydroxyl group or a carboxyl group, and still more preferably a hydroxyl group.

$R^6$ is preferably a hydrogen atom, a fluorine atom, a trifluoromethyl group, a carboxyl group, a methoxy group, an ethoxy group, an n-propyloxy group, an isopropyloxy group, a hydroxyl group, an acetyloxy group, a propanoyloxy group, a butanoyloxy group or an isobutanoyloxy group, more preferably a hydrogen atom or a hydroxyl group, and still more preferably a hydrogen atom. $R^5$ and $R^6$ may optionally together form an oxo group.

$R^7$ and $R^8$ are each preferably a hydrogen atom.

Among the compounds represented by Formula (I) or the pharmaceutically acceptable salts thereof (hereinafter referred to as "Compound (I)"), preferred specific examples are shown in Table 1, but our therapeutic agents are not limited by these.

TABLE 1

| Compound | Structural Formula |
|---|---|
| 1 | |
| 2 | |

TABLE 1-continued

| Compound | Structural Formula |
|---|---|
| 3 | |
| 4 | |
| 5 | |
| 6 | |
| 7 | |
| 8 | |

TABLE 1-continued

| Compound | Structural Formula |
|---|---|
| 9 | 1-(4-methoxyphenyl)-5-(4-methylphenyl)-4-chloro-pyrazol-3-yl substituted with 4-hydroxycyclohexane-1,4-diol |
| 10 | 1-(4-methoxyphenyl)-5-(4-methylphenyl)-pyrazol-3-yl substituted with 1-hydroxy-4-(trifluoromethyl)-4-hydroxycyclohexyl |
| 11 | 1-(4-methoxyphenyl)-5-(4-methylphenyl)-pyrazol-3-yl substituted with 1-fluoro-4-hydroxycyclohexyl |
| 12 | 1-(4-methoxyphenyl)-5-(4-methylphenyl)-pyrazol-3-yl substituted with 4-hydroxycyclohexyl acetate |
| 13 | 1-(4-methoxyphenyl)-5-(4-methylphenyl)-pyrazol-3-yl substituted with 1-hydroxy-4-methoxycyclohexyl |
| 14 | 1-(4-methoxyphenyl)-5-(4-methylphenyl)-pyrazol-3-yl substituted with 1-hydroxymethyl-4-hydroxycyclohexyl |
| 15 | 1-(4-methoxyphenyl)-5-(6-methylpyridin-3-yl)-pyrazol-3-yl substituted with 1,4-dihydroxycyclohexyl |
| 16 | 1-(4-methoxyphenyl)-5-(4-methylphenyl)-pyrazol-3-yl substituted with 1-hydroxy-4-carboxycyclohexyl |
| 17 | 1-(4-methoxyphenyl)-5-(4-methylphenyl)-pyrazol-3-yl substituted with 1-hydroxy-4,4-difluorocyclohexyl |
| 18 | 1-(4-methoxyphenyl)-5-(4-trifluoromethylphenyl)-pyrazol-3-yl substituted with 1,4-dihydroxycyclohexyl |
| 19 | 1-(4-methoxyphenyl)-5-(4-trifluoromethylphenyl)-pyrazol-3-yl substituted with 1,4-dihydroxycyclohexyl |
| 20 | 1-(4-methoxyphenyl)-5-(4-methylphenyl)-pyrazol-3-yl substituted with 1-hydroxymethyl-4-hydroxycyclohexyl |

TABLE 1-continued

| Compound | Structural Formula |
|---|---|
| 21 | 1-(4-methoxyphenyl)-5-(4-chlorophenyl)-pyrazol-3-yl cyclohexane-1,4-diol |
| 22 | 1-(4-chlorophenyl)-5-(4-methylphenyl)-pyrazol-3-yl cyclohexane-1,4-diol |
| 23 | 1,5-bis(4-chlorophenyl)-pyrazol-3-yl cyclohexane-1,4-diol |
| 24 | 1,5-bis(4-chlorophenyl)-pyrazol-3-yl cyclohexane-1,4-diol |
| 25 | 1-phenyl-5-(4-chlorophenyl)-pyrazol-3-yl cyclohexane-1,4-diol |
| 26 | 1-phenyl-5-(4-chlorophenyl)-pyrazol-3-yl cyclohexane-1,4-diol |
| 27 | 1,5-bis(4-methylphenyl)-pyrazol-3-yl cyclohexane-1,4-diol |
| 28 | 1,5-bis(4-methylphenyl)-pyrazol-3-yl cyclohexane-1,4-diol |
| 29 | 1-phenyl-5-(4-methylphenyl)-pyrazol-3-yl cyclohexane-1,4-diol |
| 30 | 1-phenyl-5-(4-methylphenyl)-pyrazol-3-yl cyclohexane-1,4-diol |
| 31 | 1-(4-methoxyphenyl)-5-phenyl-pyrazol-3-yl cyclohexane-1,4-diol |
| 32 | 1-(4-methoxyphenyl)-5-phenyl-pyrazol-3-yl cyclohexane-1,4-diol |

TABLE 1-continued

| Compound | Structural Formula |
|---|---|
| 33 | 1-(4-methylphenyl)-5-phenyl-3-(4-hydroxycyclohexyl)-pyrazole derivative (cis/trans diol) |
| 34 | 1-(4-methylphenyl)-5-phenyl-3-(4-hydroxycyclohexyl)-pyrazole derivative |
| 35 | 1-(4-methylphenyl)-5-(4-methoxyphenyl)-3-(4-hydroxycyclohexyl)-pyrazole |
| 36 | 1-(4-methylphenyl)-5-(4-methoxyphenyl)-3-(4-hydroxycyclohexyl)-pyrazole |
| 37 | 1-(4-chlorophenyl)-5-(4-methoxyphenyl)-3-(4-hydroxycyclohexyl)-pyrazole |
| 38 | 1-(4-chlorophenyl)-5-(4-methoxyphenyl)-3-(4-hydroxycyclohexyl)-pyrazole |
| 39 | 1-phenyl-5-(4-methoxyphenyl)-3-(4-hydroxycyclohexyl)-pyrazole |
| 40 | 1-phenyl-5-(4-methoxyphenyl)-3-(4-hydroxycyclohexyl)-pyrazole |
| 41 | 4-(4-methoxyphenyl)-5-(4-methylphenyl)-2-(4-hydroxycyclohexyl)-thiazole |
| 42 | 4-(4-methoxyphenyl)-5-(4-methylphenyl)-2-(4-hydroxycyclohexyl)-thiazole |
| 43 | 4-(4-methoxyphenyl)-5-(4-methoxyphenyl)-2-(4-hydroxycyclohexyl)-oxazole |
| 44 | 4-(4-methoxyphenyl)-5-(4-methylphenyl)-2-(4-hydroxycyclohexyl)-oxazole |

TABLE 1-continued

| Compound | Structural Formula |
|---|---|
| 45 | (4-methoxyphenyl and 4-methylphenyl substituted thiazole linked to cyclohexane bearing OH, CF₃, and OH) |
| 46 | (4-methoxyphenyl and 4-methylphenyl substituted thiazole linked to cyclohexane bearing OH, OH, and CF₃) |
| 47 | (4-methoxyphenyl and 4-ethylphenyl substituted pyrazole linked to cyclohexane bearing OH and OH) |
| 48 | (4-methoxyphenyl and 4-ethylphenyl substituted pyrazole linked to cyclohexane bearing OH and OH) |
| 49 | (4-cyanophenyl and 4-methylphenyl substituted pyrazole linked to cyclohexane bearing OH and OH) |
| 50 | (4-cyanophenyl and 4-methylphenyl substituted pyrazole linked to cyclohexane bearing OH and OH) |
| 51 | (4-methoxyphenyl and 4-cyanophenyl substituted pyrazole linked to cyclohexane bearing OH and OH) |
| 52 | (4-methoxyphenyl and 4-cyanophenyl substituted pyrazole linked to cyclohexane bearing OH and OH) |
| 53 | (3-fluoro-4-methoxyphenyl and 4-methylphenyl substituted pyrazole linked to cyclohexane bearing OH and OH) |
| 54 | (3-fluoro-4-methoxyphenyl and 4-methylphenyl substituted pyrazole linked to cyclohexane bearing OH and OH) |
| 55 | (4-methoxyphenyl and 3-fluoro-4-methylphenyl substituted pyrazole linked to cyclohexane bearing OH and OH) |

TABLE 1-continued

| Compound | Structural Formula |
|---|---|
| 56 | (structure) |
| 57 | (structure) |
| 58 | (structure) |

In cases where Compound (I) has an asymmetric carbon(s), all the enantiomers and mixtures thereof are within the scope of our therapeutic agents.

In cases where Compound (I) has a stereoisomer(s), all the stereoisomers and mixtures thereof are also within the scope of our therapeutic agents.

Examples of the "pharmaceutically acceptable salt" include inorganic acid salts such as hydrochloric acid salt, sulfuric acid salt, phosphoric acid salt and hydrobromic acid salt; organic acid salts such as oxalic acid salt, malonic acid salt, citric acid salt, fumaric acid salt, lactic acid salt, malic acid salt, succinic acid salt, tartaric acid salt, acetic acid salt, trifluoroacetic acid salt, maleic acid salt, gluconic acid salt, benzoic acid salt, ascorbic acid salt, methanesulfonic acid salt, p-toluenesulfonic acid salt and cinnamic acid salt; inorganic base salts such as sodium salt, potassium salt, calcium salt, magnesium salt and ammonium salt; and organic base salts such as methylamine salt, diethylamine salt, trimethylamine salt, triethylamine salt, pyridinium salt, triethanolamine salt, ethylenediamine salt and guanidine salt. Further, Compound (I) may form a hydrate or a solvate, and crystalline polymorphs are also included in Compound (I).

Compound (I) can be synthesized, for example, according to the production methods described below. The symbols in each reaction formula have the same meanings as defined above unless otherwise specified.

In cases where a raw material compound has a carboxyl group or a hydroxyl group, a protecting group as commonly used may be introduced thereto, and the protecting group may be removed as required after the reaction. Examples of the protecting group for a hydroxyl group include a $C_1$-$C_4$ alkyl group, a phenyl group, a trityl group, a $C_1$-$C_4$ aralkyl group (e.g., a benzyl group), an acyl group (e.g., a formyl group, an acetyl group or a benzoyl group), a $C_7$-$C_{10}$ aralkyl-carbonyl group (e.g., a benzylcarbonyl group) and a substituted silyl group (e.g., a trimethylsilyl group, a triethylsilyl group or a tert-butyldimethylsilyl group). Examples of the protecting group for a carboxyl group include a $C_1$-$C_4$ alkyl group.

The method to remove the protecting group varies depending on the type of the protecting group, and the removal may be carried out according to a method as described in PROTECTIVE GROUPS IN ORGANIC SYNTHESIS (WILEY-INTERSCIENCE) or a method similar thereto.

In the production methods described below, a salt may be used as a raw material compound. Examples of the salt include the same ones as the pharmaceutically acceptable salts described above.

Compound (I) obtained by the production methods described below may be isolated and purified according to known means, and examples of the known means include solvent extraction, recrystallization and chromatography.

In cases where Compound (I) has optical isomers, stereoisomers, regioisomers and/or rotamers, each of these may be obtained as a single compound by a known synthesis method and a known separation method.

Production Method 1: Production Method of Compound (Ic), Compound (Id), Compound (Ie) and Compound (If)

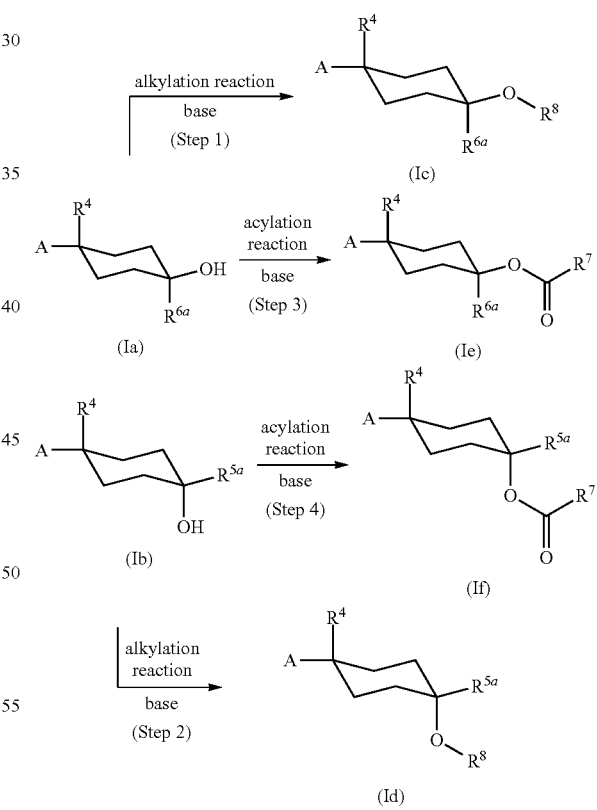

wherein $R^{5a}$ and $R^{6a}$ are each independently a hydrogen atom, a $C_1$-$C_3$ haloalkyl group, a carboxyl group or the like; $R^7$ and $R^8$ are each independently a $C_1$-$C_4$ alkyl group or the like; and the other symbols have the same meanings as defined above.

Compound (Ic) can be obtained by alkylation of Compound (Ia), and Compound (Id) can be obtained by alkylation of Compound (Ib). Compound (Ie) can be obtained by acylation of Compound (Ia), and Compound (If) can be obtained by acylation of Compound (Ib).

Step 1 and Step 2

The alkylation reaction of Compound (Ia) or Compound (Ib) is usually performed by reacting Compound (Ia) or Compound (Ib) with an alkyl halide in a solvent in the presence of a base. As the solvent, a solvent that does not inhibit the reaction is appropriately selected. Examples of the solvent that does not inhibit the reaction include ethers such as tetrahydrofuran, 1,4-dioxane and ethylene glycol dimethyl ether; acetone; acetonitrile; and N,N-dimethylformamide. A mixed solvent of these may also be used as the solvent.

Examples of the base include alkali metal hydrogen carbonates such as sodium hydrogen carbonate and potassium hydrogen carbonate; alkali metal carbonates such as potassium carbonate and cesium carbonate; amines such as triethylamine, diisopropylethylamine and pyridine; potassium tert-butoxide; and sodium hydride.

The amount of the base to be used is preferably 0.5 to 6 mol, more preferably 0.8 to 3 mol, with respect to 1 mol of Compound (Ia) or Compound (Ib).

The amount of the alkyl halide to be used is preferably 0.5 to 5 mol, more preferably 0.8 to 2 mol, with respect to 1 mol of Compound (Ia) or Compound (Ib).

The reaction temperature of the alkylation reaction is preferably −78° C. to 200° C., more preferably −20° C. to 100° C.

The reaction time of the alkylation reaction varies depending on the reaction conditions, and is preferably 5 minutes to 78 hours, more preferably 30 minutes to 48 hours.

Step 3 and Step 4

The acylation reaction of Compound (Ia) or Compound (Ib) is usually performed by reacting Compound (Ia) or Compound (Ib) with an acylating agent, such as an acid halide or an acid anhydride, in a solvent in the presence of a base. As the solvent, a solvent that does not inhibit the reaction is appropriately selected. Examples of the solvent that does not inhibit the reaction include halogenated hydrocarbons such as dichloromethane, chloroform, carbon tetrachloride and 1,2-dichloroethane; and ethers such as tetrahydrofuran, 1,2-dimethoxyethane and 1,4-dioxane. A mixed solvent of these may also be used as the solvent.

Examples of the base include pyridine, triethylamine, diisopropylethylamine, N,N-dimethylaminopyridine and the like.

The amount of the acid halide or the acid anhydride to be used is preferably 0.5 to 3 mol, more preferably 0.8 to 1.5 mol, with respect to 1 mol of Compound (Ia) or Compound (Ib).

The amount of the base to be used is preferably 0.1 to 6 mol, more preferably 0.8 to 3, with respect to 1 mol of Compound (Ia) or Compound (Ib).

The reaction temperature of the acylation reaction is preferably −20° C. to 150° C., more preferably 0° C. to 100° C.

The reaction time of the acylation reaction varies depending on the reaction conditions, and is preferably 5 minutes to 72 hours, more preferably 30 minutes to 48 hours.

Production Method 2: Production Method of Compound (Ih)

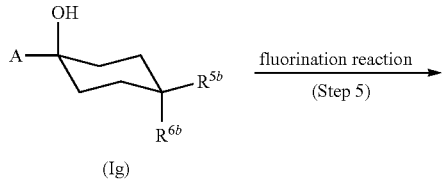

(Ig)

-continued

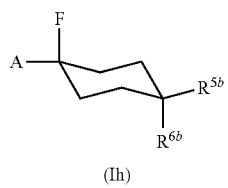

(Ih)

wherein $R^{5b}$ and $R^{6b}$ are each independently a hydrogen atom, a fluorine atom, a $C_1$-$C_3$ haloalkyl group, a $C_1$-$C_4$ alkoxy group, a $C_2$-$C_5$ alkylcarbonyloxy group or the like; and the other symbols have the same meanings as defined above.

Compound (Ih) can be obtained by fluorination of Compound (Ig).

Step 5

The fluorination reaction of Compound (Ig) is usually performed by reacting Compound (Ig) with a fluorinating agent in a solvent. As the solvent, a solvent that does not inhibit the reaction is appropriately selected. Examples of the solvent that does not inhibit the reaction include hydrocarbons such as octane, hexane, benzene and toluene; halogenated hydrocarbons such as dichloromethane, chloroform, carbon tetrachloride and 1,2-dichloroethane; ethers such as tetrahydrofuran, 1,2-dimethoxyethane and 1,4-dioxane; and alkyl nitriles such as acetonitrile. A mixed solvent of these may also be used as the solvent.

Examples of the fluorinating agent include alkylaminosulfur trifluorides such as (dimethylamino)sulfur trifluoride (DAST) and bis(2-methoxyethyl)aminosulfur trifluoride acid.

The amount of the fluorinating agent to be used is preferably 0.25 to 20 mol, more preferably 0.5 to 4 mol, with respect to 1 mol of Compound (Ig).

The reaction temperature of the fluorination reaction is preferably −20° C. to 150° C., more preferably 0° C. to 100° C.

The reaction time of the fluorination reaction varies depending on the reaction conditions, and is preferably 5 minutes to 72 hours, more preferably 30 minutes to 48 hours.

Production Method 3: Production Method of Compound (Ij)

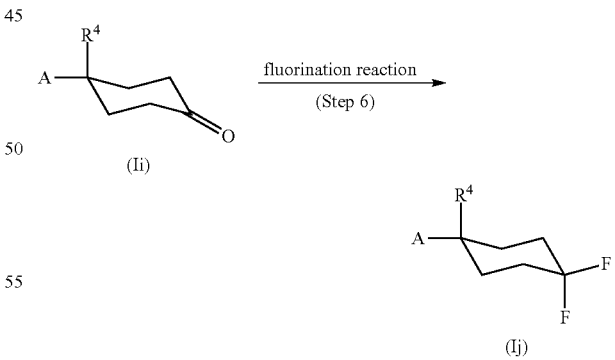

wherein the symbols have the same meanings as defined above.

Compound (Ij) can be obtained by fluorination of Compound (Ii).

Step 6

The fluorination reaction of Compound (Ii) is usually performed by reacting Compound (Ii) with a fluorinating agent in a solvent. As the solvent, a solvent that does not inhibit the reaction is appropriately selected. Examples of the solvent that does not inhibit the reaction include hydrocarbons such as octane, hexane, benzene and toluene; halogenated hydrocarbons such as dichloromethane, chloroform, carbon tetrachloride and 1,2-dichloroethane; ethers such as tetrahydrofuran, 1,2-dimethoxyethane and 1,4-dioxane; and alkyl nitriles such as acetonitrile. Alternatively, a mixed solvent of these may be use as the solvent.

Examples of the fluorinating agent include alkylaminosulfur trifluorides such as (dimethylamino)sulfur trifluoride (DAST) and bis(2-methoxyethyl)aminosulfur trifluoride acid.

The amount of the fluorinating agent to be used is preferably 0.25 to 20 mol, more preferably 0.5 to 4 mol, with respect to 1 mol of Compound (II).

The reaction temperature of the fluorination reaction is preferably −20° C. to 150° C., more preferably 0° C. to 100° C.

The reaction time of the fluorination reaction varies depending on the reaction conditions, and is preferably 5 minutes to 72 hours, more preferably 30 minutes to 48 hours.

Production Method 4: Production Method of Compound (Ik) and Compound (Il)

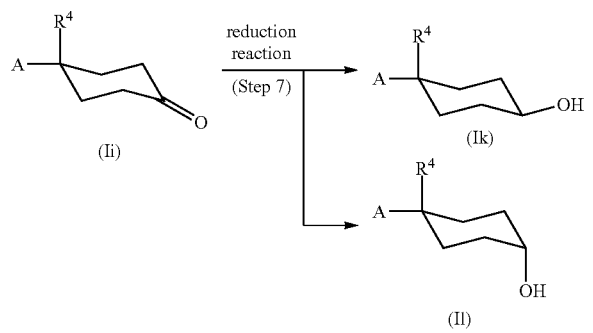

wherein the symbols have the same meanings as defined above.

Compound (Ik) and Compound (Il) can be obtained by reducing Compound (Ii).

Step 7

The reduction reaction of Compound (Ii) is usually performed by reacting Compound (Ii) with a reducing agent in a solvent. As the solvent, a solvent that does not inhibit the reaction is appropriately selected. Examples of the solvent that does not inhibit the reaction include hydrocarbons such as octane, hexane, benzene and toluene; ethers such as tetrahydrofuran, 1,4-dioxane, ethylene glycol dimethyl ether and diethyl ether; and alcohols such as methanol, ethanol and isopropyl alcohol. A mixed solvent of these may also be used as the solvent.

Examples of the reducing agent include sodium borohydride, lithium borohydride, diisobutylaluminium hydride, lithium aluminum hydride, lithium triethyl hydride, sodium bis(2-methoxyethoxy)aluminum hydride and borane complexes.

The amount of the reducing agent to be used is preferably 0.25 to 100 mol, more preferably 0.5 to 20 mol, with respect to 1 mol of Compound (Ii).

The reaction temperature of the reduction reaction is preferably −78° C. to 150° C., more preferably −78° C. to 100° C.

The reaction time of the reduction reaction varies depending on the reaction conditions such as the reaction temperature, the amount of the reducing agent and the like, and is preferably 5 minutes to 72 hours, more preferably 30 minutes to 24 hours.

Production Method 5: Production Method of Compound (Im) and Compound (In)

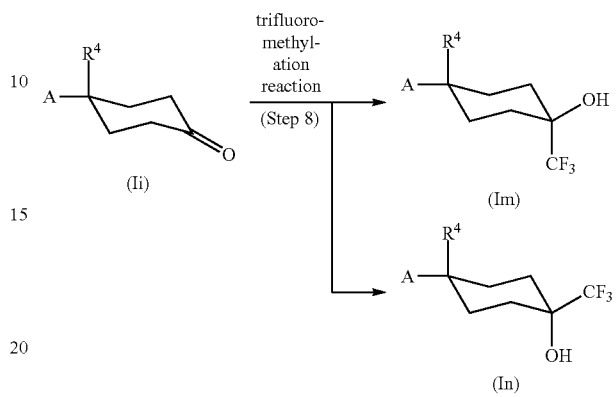

wherein the symbols have the same meanings as defined above.

Compound (Im) and Compound (In) can be obtained by trifluoromethylation of Compound (Ii).

Step 8

Examples of the trifluoromethylating agent include organosilicon compounds such as (trifluoromethyl)trimethylsilane. The trifluoromethylation reaction using an organosilicon compound may be carried out according to a method as described in Journal of the American Chemical Society, 1989, Vol. 39, pp. 393-395 or a method similar thereto.

Production Method 6: Production Method of Compound (Io)

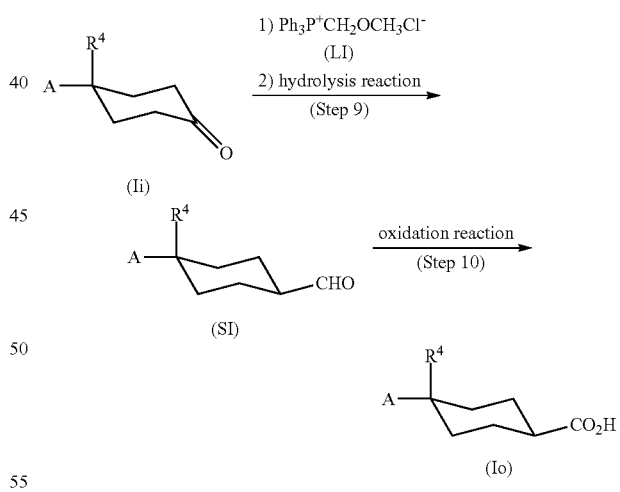

wherein the symbols have the same meanings as defined above.

Compound (SI) can be obtained by allowing a Wittig reagent (LI) to act on Compound (Ii), and then hydrolyzing the resulting compound. As the Wittig reagent, a commercially available compound may be used, or it may be synthesized according to a known method. Compound (Io) can be obtained by oxidizing Compound (SI).

Step 9

The Wittig reaction of Compound (Ii) is usually performed by reacting Compound (Ii) with a Wittig reagent in a solvent in the presence of a base. As the solvent, a solvent that does not inhibit the reaction is appropriately selected. Examples of the solvent that does not inhibit the reaction include hydrocarbons such as octane, hexane, benzene and toluene; and ethers such as tetrahydrofuran, 1,4-dioxane, ethylene glycol dimethyl ether and diethyl ether. A mixed solvent of these may also be used as the solvent.

Examples of the base include lithium diisopropylamide, potassium tert-butoxide, sodium hydride, phenyllithium and tert-butyllithium.

The amount of the base to be used is preferably 0.5 to 3 mol, more preferably 0.8 to 2 mol, with respect to 1 mol of Compound (Ii).

The amount of Compound (LI) to be used is preferably 0.5 to 3 mol, more preferably 0.8 to 2 mol, with respect to 1 mol of Compound (Ii).

The reaction temperature of the Wittig reaction is preferably −78° C. to 100° C., more preferably −78° C. to 50° C.

The reaction time of the Wittig reaction varies depending on the reaction conditions such as the reaction temperature, and is preferably 5 minutes to 48 hours, more preferably 30 minutes to 24 hours.

The hydrolysis reaction to obtain Compound (SI) is performed in an appropriately selected solvent that does not inhibit the reaction. Examples of the solvent that does not inhibit the reaction include ethers such as tetrahydrofuran, 1,4-dioxane and ethylene glycol dimethyl ether; alcohols such as methanol, ethanol and tert-butanol; acetonitrile; and water. A mixed solvent of these may also be used as the solvent.

The concentration of the acid which is used in the hydrolysis reaction is preferably 0.1 M to 12 M, and the amount of the acid to be used is preferably from 1 mol to an excess amount with respect to 1 mol of Compound (Ii)

Examples of the acid which is used in the hydrolysis reaction include inorganic acids such as hydrochloric acid and sulfuric acid; and organic acids such as acetic acid.

The reaction temperature of the hydrolysis reaction is preferably −20° C. to 200° C., more preferably 0° C. to 100° C.

The reaction time of the hydrolysis reaction varies depending on the reaction conditions, and is preferably 5 minutes to 48 hours, more preferably 30 minutes to 24 hours.

Step 10

Examples of the oxidizing agent which is used in oxidation reaction of Compound (SI) include chromium (VI) oxide-acetic acid, Jones reagent, sodium chlorite and the like. The oxidation reaction may be carried out according to a known method.

Production Method 7: Production Method of Compound (Ii)

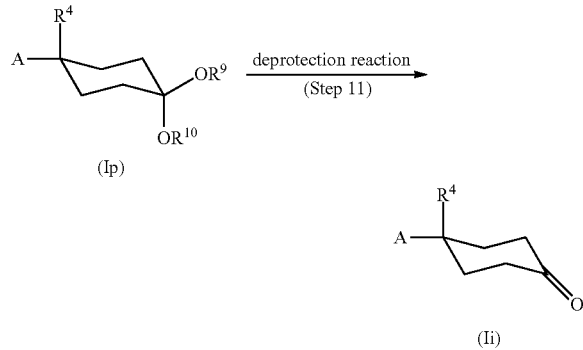

wherein $R^9$ and $R^{10}$ are each independently a methyl group, an ethyl group, an n-propyl group, an isopropyl group, an n-butyl group, a sec-butyl group or a tert-butyl group or the like, or $R^9$ and $R^{10}$ may together form an ethylene group (—CH$_2$CH$_2$—), a propylene group (—CH$_2$CH$_2$CH$_2$—) or the like; and the other symbols have the same meanings as defined above.

Compound (Ii) can be obtained by deprotection of Compound (Ip).

Step 11

The deprotection reaction of Compound (Ip) may be carried out according to a method as described in PROTECTIVE GROUPS IN ORGANIC SYNTHESIS (WILEY-INTERSCIENCE) or a method similar thereto.

Production Method 8: Production Method of Compound (IIIb)

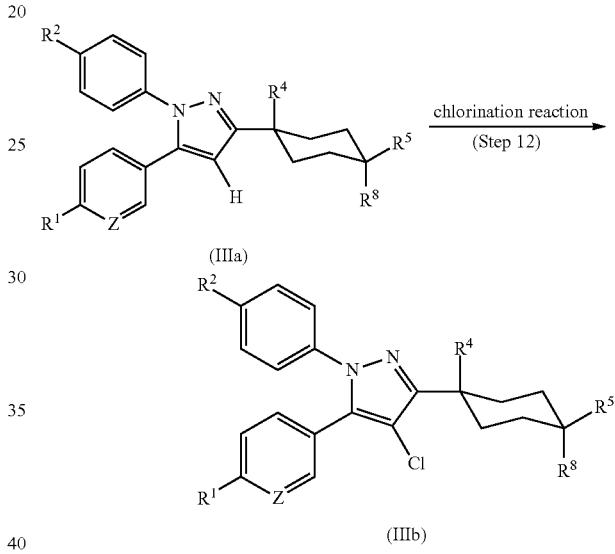

wherein the symbols have the same meanings as defined above.

Compound (IIIb) can be obtained by chlorination of Compound (IIIa).

Step 12

The chlorination reaction of Compound (IIIa) is usually performed by reacting Compound (IIIa) with a chlorinating agent in a solvent. As the solvent, a solvent that does not inhibit the reaction is appropriately selected. Examples of the solvent that does not inhibit the reaction include halogenated hydrocarbons such as dichloromethane, chloroform, carbon tetrachloride and 1,2-dichloroethane; acetonitrile: and ethyl acetate. A mixed solvent of these may also be used as the solvent.

Examples of the chlorinating agent include N-chlorosuccinimide (NCS).

The amount of the chlorinating agent to be used is preferably 0.5 to 2 mol, more preferably 0.8 to 1.2 mol, with respect to 1 mol of Compound (IIIa).

The reaction temperature of the chlorination reaction is preferably 0° C. to 200° C., more preferably 0° C. to 120° C.

The reaction time of the chlorination reaction varies depending on the reaction conditions such as the reaction temperature, and is preferably 5 minutes to 72 hours, more preferably 30 minutes to 48 hours.

Production Method 9: Production Method of Compound (IIIa)

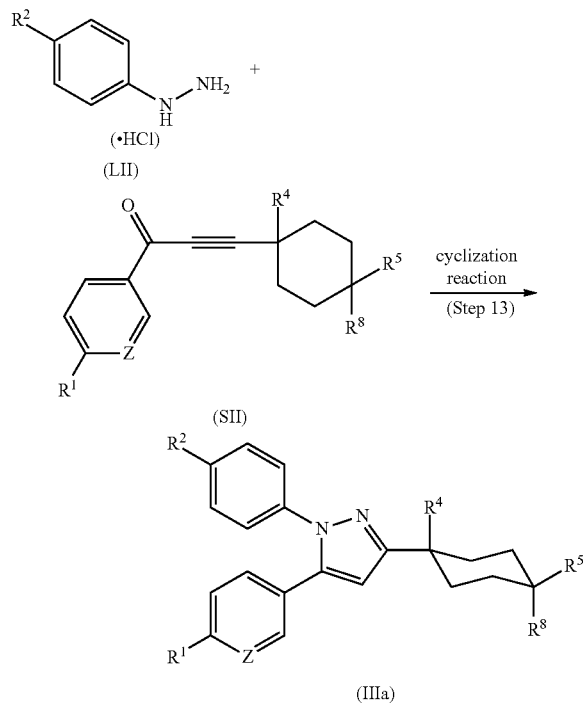

wherein the symbols have the same meanings as defined above.

Step 13

The cyclization reaction of Compound (LII) with Compound (SII) is usually performed in an appropriately selected solvent that does not inhibit the reaction. Examples of the solvent that does not inhibit the reaction include alcohols such as methanol, ethanol and isopropyl alcohol; halogenated hydrocarbons such as dichloromethane, chloroform, carbon tetrachloride and 1,2-dichloroethane; ethers such as tetrahydrofuran, 1,2-dimethoxyethane and 1,4-dioxane; benzene; toluene; acetic acid; and water. A mixed solvent of these may also be used as the solvent.

The amount of Compound (LII) to be used is preferably 0.5 to 1.5 mol, more preferably 0.8 to 1.2 mol, with respect to 1 mol of Compound (SII).

In the cyclization reaction, a catalyst may be used, and examples of the catalyst include organic bases such as triethylamine and pyridine; inorganic acids such as hydrochloric acid and sulfuric acid; and organic acids such as acetic acid.

The amount of the catalyst to be used is preferably 0.1 to 3 mol with respect to 1 mol of Compound (SII).

The reaction temperature of the cyclization reaction is preferably 0° C. to 200° C., more preferably 0° C. to 120° C.

The reaction time of the cyclization reaction varies depending on the reaction conditions such as the reaction temperature, and is preferably 5 minutes to 72 hours, more preferably 30 minutes to 48 hours.

Production Method 10: Production Method of Compound (IV)

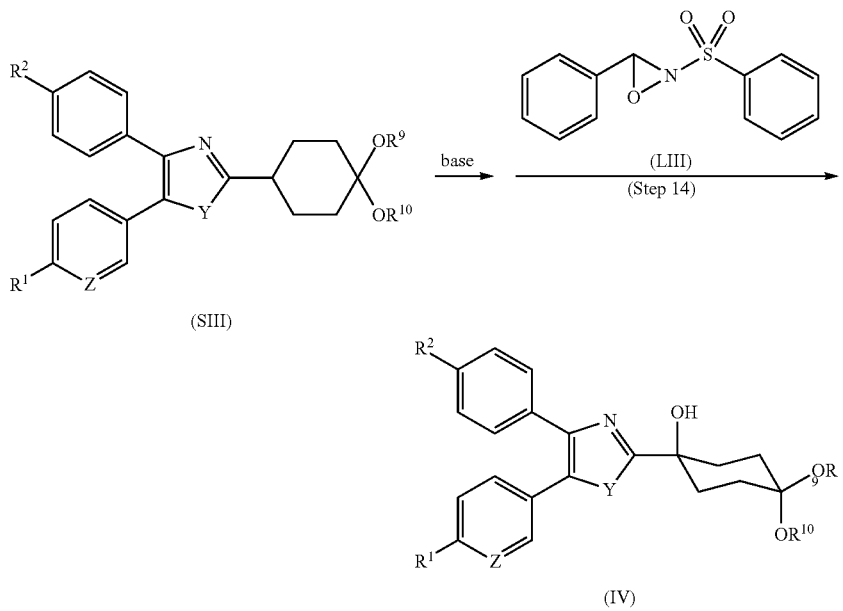

Compound (IIIa) can be obtained by cyclization of Compound (LII) with Compound (SII). As Compound (LII), a commercially available compound may be used, or it may be synthesized according to a known method.

wherein the symbols have the same meanings as defined above.

Compound (IV) can be obtained by deprotonation and oxidization of Compound (SIII). The oxidation reaction may be carried out according to a method as described in Tetrahedron, 1989, Vol. 45, pp. 5703-5742 or a method similar thereto.

Step 14

The deprotonation reaction and the oxidation reaction of Compound (SIII) are usually performed by reacting Compound (SIII) with a base and an oxidizing agent in an anhydrous solvent. As the solvent, a solvent that does not inhibit the reaction is appropriately selected. Examples of the solvent that does not inhibit the reaction include hydrocarbons such as octane, hexane and heptane; and ethers such as tetrahydrofuran, 1,4-dioxane, ethylene glycol dimethyl ether and diethyl ether. A mixed solvent of these may also be used as the solvent.

Examples of the base include butyllithiums such as n-butyllithium, sec-butyllithium and tert-butyllithium.

The amount of the base to be used is preferably 0.8 to 5 mol, more preferably 0.9 to 3 mol, with respect to 1 mol of Compound (SIII).

The amount of Compound (LIII) to be used is preferably 0.8 to 5 mol, more preferably 0.9 to 3 mol, with respect to 1 mol of Compound (SIII).

Examples of the oxidizing agent which is used in the oxidation reaction include 3-phenyl-2-(phenylsulfonyl)-1,2-oxaziridine.

The reaction temperature of the deprotonation reaction and the oxidation reaction is preferably $-78°$ C. to $150°$ C., more preferably $0°$ C. to $50°$ C.

The reaction time of the deprotonation reaction and the oxidation reaction varies depending on the reaction conditions, and is preferably 5 minutes to 72 hours, more preferably 30 minutes to 48 hours.

Production Method 11: Production Method of Intermediate Compound (VI)

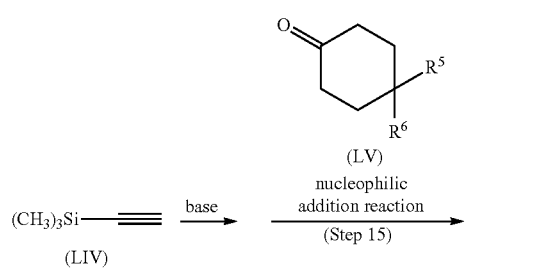

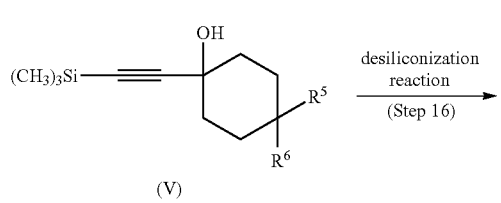

-continued

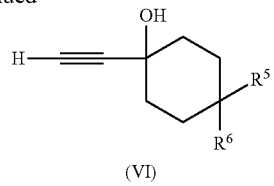

wherein the symbols have the same meanings as defined above.

Compound (VI) can be obtained by solvolysis of Compound (V) which has been obtained by reacting Compound (LIV) and Compound (LV). As Compound (LIV) and Compound (LV), commercially available compounds may be used, or they may be synthesized according to known methods.

Step 15

The reaction between Compound (LIV) and Compound (LV) is usually performed in an anhydrous solvent in the presence of a base; and, as the solvent, a solvent that does not inhibit the reaction is appropriately selected. Examples of the solvent that does not inhibit the reaction include hydrocarbons such as octane, hexane, benzene and toluene; and ethers such as tetrahydrofuran, 1,4-dioxane, ethylene glycol dimethyl ether and diethyl ether. A mixed solvent of these may also be used as the solvent.

Examples of the base include alkyllithiums such as methyllithium and n-butyllithium; and salts of dialkylamines such as lithium diisopropylamide, lithium bis(trimethylsilyl)amide and potassium bis(trimethylsilyl)amide.

The amount of the base to be used is preferably 0.8 to 5 mol, more preferably 0.9 to 3 mol, with respect to 1 mol of Compound (LIV).

The amount of Compound (LV) to be used is preferably 0.8 to 5 mol, more preferably 0.9 to 3 mol, with respect to 1 mol of Compound (LIV).

The reaction temperature of the reaction between Compound (LIV) and Compound (LV) is preferably $-78°$ C. to $150°$ C., more preferably $-78°$ C. to $100°$ C.

The reaction time of the reaction between Compound (LIV) and Compound (LV) varies depending on the reaction conditions, and is preferably 5 minutes to 72 hours, more preferably 30 minutes to 48 hours.

Step 16

The solvolysis reaction is usually performed in a solvent in the presence of a base; and, as the solvent, a solvent that does not inhibit the reaction is appropriately selected. Examples of the solvent that does not inhibit the reaction include alcohols such as methanol and ethanol; and water. A mixed solvent of these may also be used as the solvent.

Examples of the base include potassium carbonate, sodium carbonate, potassium hydroxide and sodium hydroxide.

The amount of the base to be used is preferably 0.5 to 10 mol, more preferably 0.8 to 3 mol, with respect to 1 mol of Compound (V).

The reaction temperature of the solvolysis reaction is preferably $-20°$ C. to $150°$ C., more preferably $0°$ C. to $100°$ C.

The reaction time of the solvolysis reaction varies depending on the reaction conditions, and is preferably 5 minutes to 72 hours, more preferably 30 minutes to 48 hours.

Production Method 12: Production Method of Intermediate Compound (SIIa)

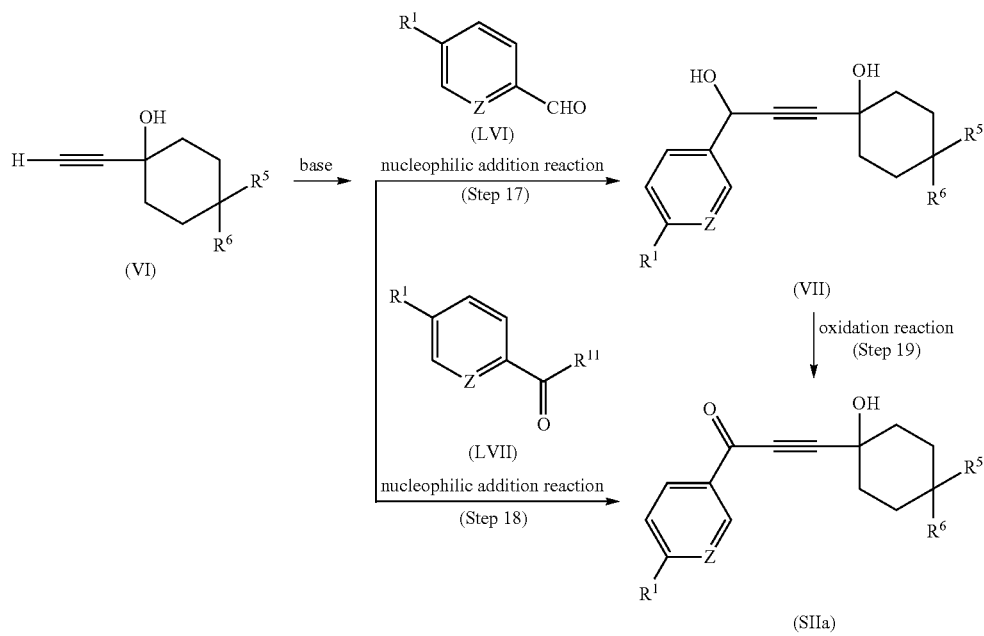

wherein $R^{11}$ represents a chlorine atom, an imidazolyl group, an N-methoxy-N-methylamino group, an alkoxy group such as a methoxy group or an ethoxy group, or the like; and the other symbols have the same meanings as defined above.

Compound (SIIa) can be obtained by oxidizing Compound (VII) which has been obtained by reacting Compound (VI) and Compound (LVI). Compound (SIIa) can also be obtained by reacting Compound (VI) and Compound (LVII). As Compound (LVI) and Compound (LVII), commercially available compounds may be used, or they may be synthesized according to a known method.

Step 17 and Step 18

The reaction between Compound (VI) and Compound (LVI) or Compound (LVII) is usually performed in an anhydrous solvent in the presence of a base; and, as the solvent, a solvent that does not inhibit the reaction is appropriately selected. Examples of the solvent that does not inhibit the reaction include hydrocarbons such as octane, hexane, benzene and toluene; and ethers such as tetrahydrofuran, 1,4-dioxane, ethylene glycol dimethyl ether and diethyl ether. A mixed solvent of these may also be used as the solvent.

Examples of the base include alkyllithiums such as methyllithium and n-butyllithium; and salts of dialkylamines such as lithium diisopropylamide, lithium bis(trimethylsilyl) amide and potassium bis(trimethylsilyl)amide.

The amount of the base to be used is preferably 0.8 to 5 mol, more preferably 0.9 to 3 mol, with respect to 1 mol of Compound (VI).

The amount of Compound (LVI) to be used in Step 17 or Compound (LVII) to be used in Step 18 is preferably 0.8 to 5 mol, more preferably 0.9 to 3 mol, with respect to 1 mol of Compound (VI).

The reaction temperature of the reaction between Compound (VI) and Compound (LVI) in Step 17 or Compound (LVII) in Step 18 is preferably −78° C. to 150° C., more preferably 0° C. to 50° C.

The reaction time of the reaction between Compound (VI) and Compound (LVI) in Step 17 or Compound (LVII) in Step 18 varies depending on the reaction conditions, and is preferably 5 minutes to 72 hours, more preferably 30 minutes to 48 hours.

Step 19

The oxidation reaction of Compound (VII) is usually performed by reacting Compound (VII) with an oxidizing agent in a solvent. As the solvent, a solvent that does not inhibit the reaction is appropriately selected. Examples of the solvent that does not inhibit the reaction include hydrocarbons such as octane, hexane, benzene and toluene; halogenated hydrocarbons such as dichloromethane, chloroform, carbon tetrachloride and 1,2-dichloroethane; ethers such as tetrahydrofuran, 1,2-dimethoxyethane and 1,4-dioxane; and alkyl nitriles such as acetonitrile; trifluoroacetic acid; pyridine; acetone; and the like. A mixed solvent of these may also be used as the solvent.

Examples of the oxidizing agent include commercially available reagents such as manganese dioxide, sulfur trioxide-pyridine, activated dimethyl sulfoxide and Dess-Martin reagent.

The amount of the oxidizing agent to be used is preferably 0.5 to 3 mol, more preferably 0.8 to 2 mol, with respect to 1 mol of Compound (VII).

The reaction temperature of the oxidation reaction varies depending on the type of the oxidizing agent, and is preferably −78° C. to 100° C., more preferably −78° C. to 40° C.

The reaction time of the oxidation reaction varies depending on the reaction conditions such as the type of the oxidizing agent, the reaction temperature and the like, and is preferably 5 minutes to 72 hours, more preferably 1 hour to 24 hours.

Production Method 13: Production Method of Intermediate Compound (IX)

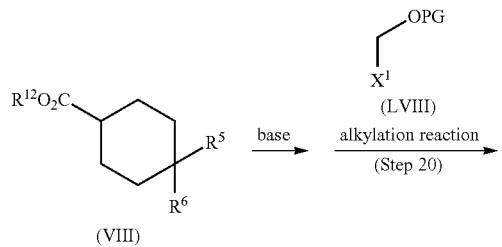

Production Method 14: Production Method of Intermediate Compound (XI)

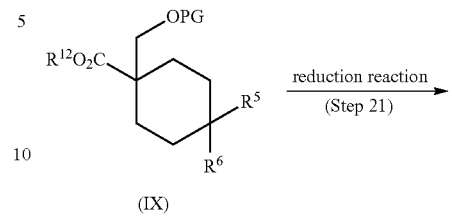

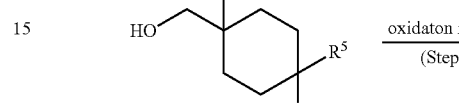

wherein $X^1$ is a halogen atom; PG is a protecting group such as methyl or benzyl; $R^{12}$ is an alkoxy group such as a methoxy group or an ethoxy group, or the like; and the other symbols have the same meanings as defined above.

Compound (IX) can be obtained by reacting Compound (VIII) and Compound (LVIII). As Compound (VIII) and Compound (LVIII), commercially available compounds may be used, or they may be synthesized according to a known method.

Step 20

The reaction between Compound (VIII) and Compound (LVIII) is usually performed in an anhydrous solvent in the presence of a base; and, as the solvent, a solvent that does not inhibit the reaction is appropriately selected. Examples of the solvent that does not inhibit the reaction include hydrocarbons such as octane, hexane, benzene and toluene; and ethers such as tetrahydrofuran, 1,4-dioxane, ethylene glycol dimethyl ether and diethyl ether. A mixed solvent of these may also be used as the solvent.

Examples of the base include lithium diisopropylamide, lithium bis(trimethylsilyl)amide and potassium bis(trimethylsilyl)amide.

The amount of the base to be used is preferably 0.8 to 4 mol, more preferably 0.9 to 3.5 mol, with respect to 1 mol of Compound (VIII).

The amount of Compound (LVIII) to be used is preferably 0.8 to 5 mol, more preferably 0.9 to 3 mol, with respect to 1 mol of Compound (VIII).

The reaction temperature of the reaction between Compound (VIII) and Compound (LVIII) is preferably −78° C. to 150° C., more preferably 0° C. to 50° C.

The reaction time of the reaction between Compound (VIII) and Compound (LVIII) varies depending on the reaction conditions, and is preferably 5 minutes to 72 hours, more preferably 30 minutes to 48 hours.

wherein the symbols have the same meanings as defined above.

Compound (XI) can be obtained by oxidizing Compound (X) which has been obtained by reducing Compound (IX).

Step 21

The reduction reaction of Compound (IX) is usually performed by reacting Compound (IX) with a reducing agent in a solvent. As the solvent, a solvent that does not inhibit the reaction is appropriately selected. Examples of the solvent that does not inhibit the reaction include hydrocarbons such as octane, hexane, benzene and toluene; ethers such as tetrahydrofuran, 1,4-dioxane, ethylene glycol dimethyl ether and diethyl ether; and alcohols such as methanol, ethanol and isopropyl alcohol. A mixed solvent of these may also be used as the solvent.

Examples of the reducing agent include lithium borohydride, diisobutylaluminium hydride, lithium aluminum hydride, lithium triethyl hydride, sodium bis(2-methoxyethoxy)aluminum hydride and borane complexes.

The amount of the reducing agent to be used is preferably 0.25 to 100 mol, more preferably 0.5 to 20 mol, with respect to 1 mol of Compound (IX).

The reaction temperature of the reduction reaction is preferably −78° C. to 150° C., more preferably −78° C. to 100° C.

The reaction time of the reduction reaction varies depending on the reaction conditions such as the reaction temperature, the amount of the reducing agent and the like, and is preferably 5 minutes to 72 hours, more preferably 30 minutes to 24 hours.

Step 22

The oxidation reaction of Compound (X) is usually performed by reacting Compound (X) with an oxidizing agent in a solvent. As the solvent, a solvent that does not inhibit the reaction is appropriately selected. Examples of the solvent that does not inhibit the reaction include trifluoroacetic acid; pyridine; acetone; hydrocarbons such as octane, hexane, benzene and toluene; halogenated hydrocarbons such as dichloromethane, chloroform, carbon tetrachloride and 1,2-dichloroethane; ethers such as tetrahydrofuran, 1,2-dimethoxyethane and 1,4-dioxane; and alkyl nitriles such as acetonitrile. A mixed solvent of these may also be used as the solvent.

Examples of the oxidizing agent include commercially available reagents such as sulfur trioxide-pyridine, activated dimethyl sulfoxide and Dess-Martin reagent.

The amount of the oxidizing agent to be used is preferably 0.5 to 3 mol, more preferably 0.8 to 2 mol, with respect to 1 mol of Compound (X).

The reaction temperature of the oxidation reaction varies depending on the type of the oxidizing agent, and is preferably −78° C. to 100° C., more preferably −78° C. to 40° C.

The reaction time of the oxidation reaction varies depending on the reaction conditions such as the type of the oxidizing agent, the reaction temperature and the like, and is preferably 5 minutes to 72 hours, more preferably 1 hour to 24 hours.

Production Method 15: Production Method of Intermediate Compound (XII)

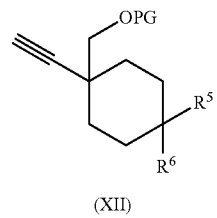

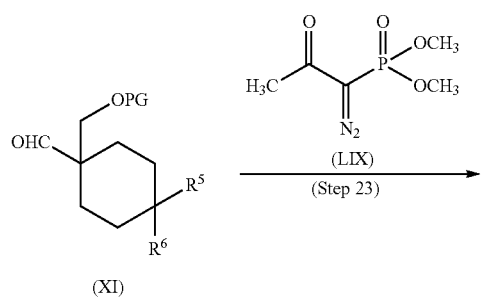

wherein the symbols have the same meanings as defined above.

Step 23

Compound (XII) can be obtained by converting Compound (XI) to an alkyne. Examples of the reagent which is used in the conversion reaction include dimethyl-1-diazo-2-oxopropylphosphonate. The conversion reaction may be carried out according to a method as described in Tetrahedron Letters, 2006, Vol. 47, pp. 1729-1731 or a method similar thereto.

Production Method 16: Production Method of Intermediate Compound (SIIb)

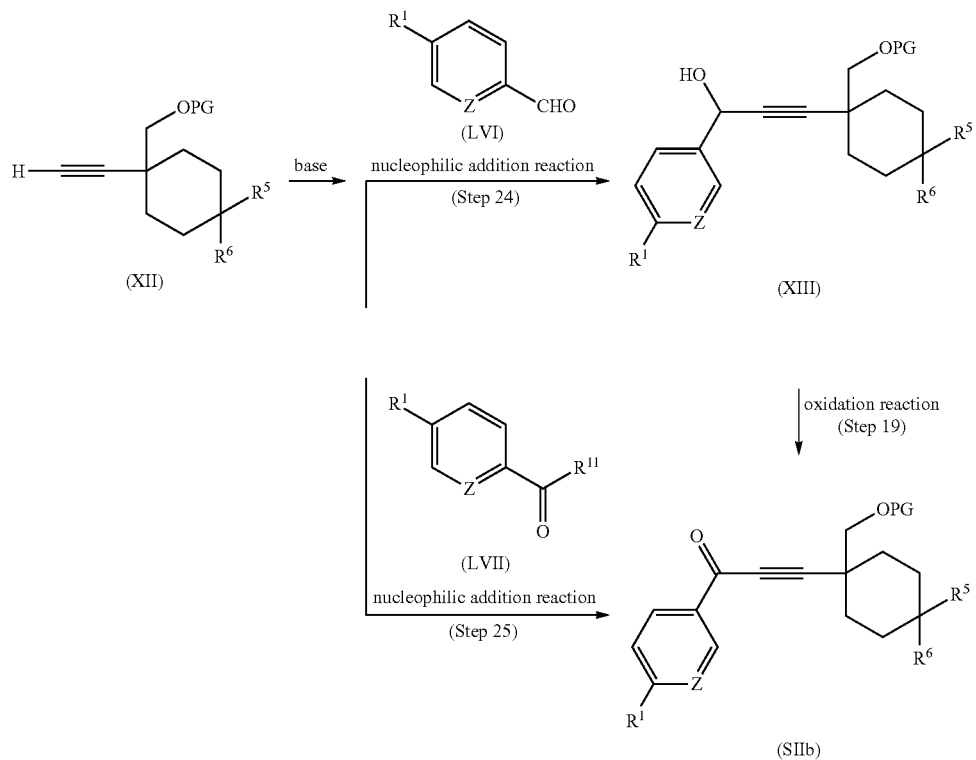

wherein the symbols have the same meanings as defined above.

Compound (SIIb) can be obtained by oxidizing Compound (XIII) which has been obtained by reacting Compound (XII) and Compound (LVI). Compound (SIIb) can also be obtained by reacting Compound (XII) and Compound (LVII). As Compound (LVI) and Compound (LVII), commercially available compounds may be used, or they may be synthesized according to a known method.

Step 24 and Step 25

The nucleophilic addition reaction of Compound (XII) is usually performed in an anhydrous solvent in the presence of a base; and, as the solvent, a solvent that does not inhibit the reaction is appropriately selected. Examples of the solvent that does not inhibit the reaction include hydrocarbons such as octane, hexane, benzene and toluene; and ethers such as tetrahydrofuran, 1,4-dioxane, ethylene glycol dimethyl ether and diethyl ether. A mixed solvent of these may also be used as the solvent.

Examples of the base include alkyllithiums such as methyllithium and n-butyllithium; and salts of dialkylamines such as lithium diisopropylamide, lithium bis(trimethylsilyl)amide and potassium bis(trimethylsilyl)amide.

The amount of the base to be used is preferably 0.8 to 5 mol, more preferably 0.9 to 3 mol, with respect to 1 mol of Compound (XII).

The amount of Compound (LVI) to be used in Step 24 or Compound (LVII) to be used in Step 25 is preferably 0.8 to 5 mol, more preferably 0.9 to 3 mol, with respect to 1 mol of Compound (XII).

The reaction temperature of the nucleophilic addition reaction is preferably −78° C. to 150° C., more preferably 0° C. to 50° C.

The reaction time of the nucleophilic addition reaction varies depending on the reaction conditions, and is preferably 5 minutes to 72 hours, more preferably 30 minutes to 48 hours.

Step 26

The oxidation reaction of Compound (XIII) is usually performed by reacting Compound (XIII) with an oxidizing agent in a solvent. As the solvent, a solvent that does not inhibit the reaction is appropriately selected. Examples of the solvent that does not inhibit the reaction include trifluoroacetic acid; pyridine; acetone; hydrocarbons such as octane, hexane, benzene and toluene; halogenated hydrocarbons such as dichloromethane, chloroform, carbon tetrachloride and 1,2-dichloroethane; ethers such as tetrahydrofuran, 1,2-dimethoxyethane and 1,4-dioxane; and alkyl nitriles such as acetonitrile. A mixed solvent of these may also be used as the solvent.

Examples of the oxidizing agent include commercially available reagents such as manganese dioxide, sulfur trioxide-pyridine, activated dimethyl sulfoxide and Dess-Martin reagent.

The amount of the oxidizing agent to be used is preferably 0.5 to 3 mol, more preferably 0.8 to 2 mol, with respect to 1 mol of Compound (XIII).

The reaction temperature of the oxidation reaction varies depending on the type of the oxidizing agent, and is preferably −78° C. to 100° C., more preferably −78° C. to 40° C.

The reaction time of the oxidation reaction varies depending on the reaction conditions such as the type of the oxidizing agent, the reaction temperature and the like, and is preferably 5 minutes to 72 hours, more preferably 1 hour to 24 hours.

Production Method 17: Production Method of Intermediate Compound (SIIIa)

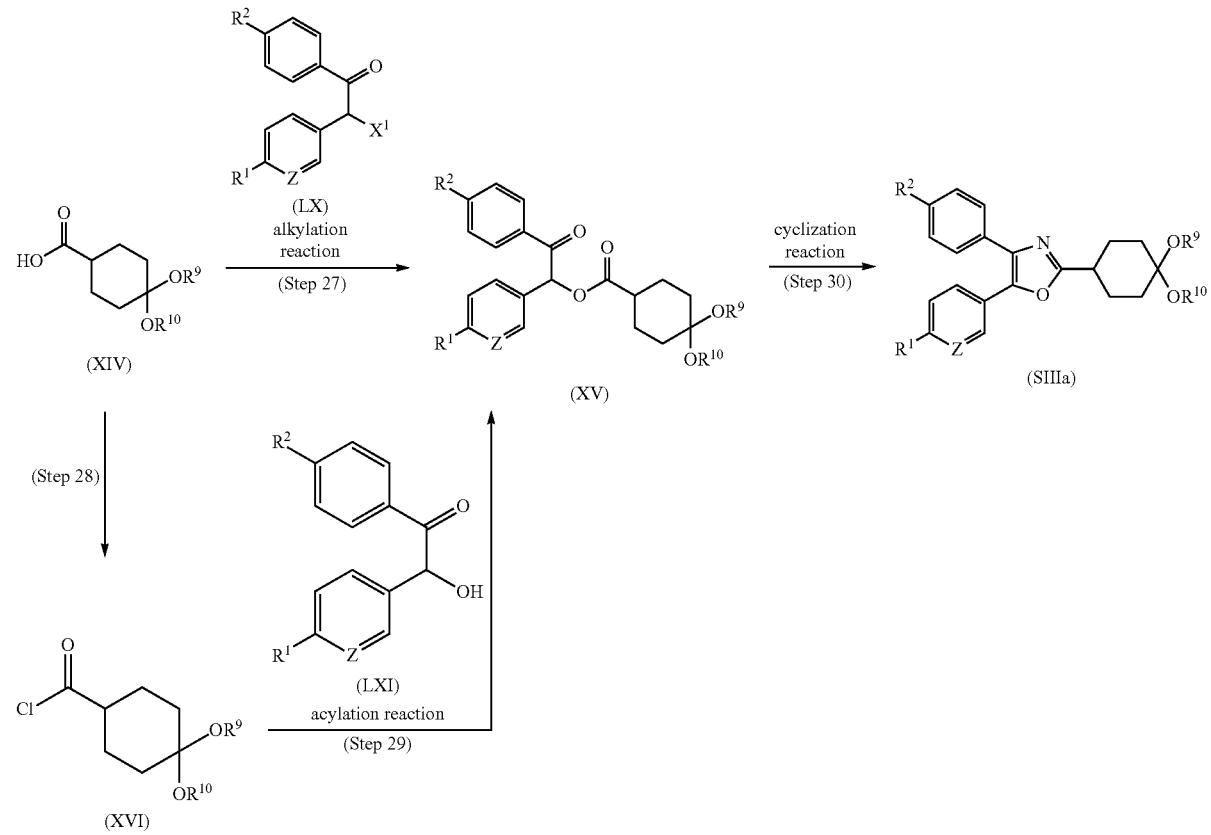

wherein the symbols have the same meanings as defined above.

Compound (SIIIa) can be obtained by cyclizing Compound (XV) which has been obtained by alkylating Compound (XIV) with Compound (LX) or acylating Compound (XVI), obtained from Compound (XIV), with Compound (LXI). Compound (XIV) and Compound (LX) may be synthesized according to known methods. As Compound (LXI), a commercially available compound may be used, or it may be synthesized according to a known method.

Step 27

The alkylation reaction of Compound (XIV) is usually performed by reacting Compound (XIV) with an alkyl halide in a solvent in the presence of a base; and, as the solvent, a solvent that does not inhibit the reaction is appropriately selected. Examples of the solvent that does not inhibit the reaction include ethers such as tetrahydrofuran, 1,4-dioxane and ethylene glycol dimethyl ether; acetone; acetonitrile; and N,N-dimethylformamide. A mixed solvent of these may also be used as the solvent.

Examples of the base include alkali metal hydrogen carbonates such as sodium hydrogen carbonate and potassium hydrogen carbonate; alkali metal carbonates such as potassium carbonate and cesium carbonate; amines such as triethylamine, diisopropylethylamine and pyridine; potassium tert-butoxide; and sodium hydride.

The amount of the base to be used is preferably 0.5 to 6 mol, more preferably 0.8 to 3 mol, with respect to 1 mol of Compound (XIV).

The amount of Compound (LX) to be used is preferably 0.5 to 5 mol, more preferably 0.8 to 2 mol, with respect to 1 mol of Compound (XIV).

The reaction temperature of the alkylation reaction is preferably −78° C. to 200° C., more preferably −20° C. to 100° C.

The reaction time of the alkylation reaction varies depending on the reaction conditions, and is preferably 5 minutes to 78 hours, more preferably 30 minutes to 48 hours.

Step 28

Compound (XVI) can be synthesized from Compound (XIV) according to, for example, a method obvious to those skilled in the art in which thionyl chloride, oxalyl chloride or the like is used.

Step 29

The acylation reaction of Compound (LXI) with Compound (XVI) is usually performed in a solvent in the presence of a base; and, as the solvent, a solvent that does not inhibit the reaction is appropriately selected. Examples of the solvent that does not inhibit the reaction include halogenated hydrocarbons such as dichloromethane, chloroform, carbon tetrachloride and 1,2-dichloroethane; and ethers such as tetrahydrofuran, 1,2-dimethoxyethane and 1,4-dioxane. A mixed solvent of these may also be used as the solvent.

Examples of the base include pyridine, triethylamine, diisopropylethylamine, N,N-dimethylaminopyridine and the like.

The amount of the base to be used is preferably 0.1 to 6 mol, more preferably 0.8 to 3 mol, with respect to 1 mol of Compound (XVI).

The amount of Compound (LXI) to be used is preferably 0.5 to 3 mol, more preferably 0.8 to 1.5 mol, with respect to 1 mol of Compound (XVI).

The reaction temperature of the acylation reaction is preferably −20° C. to 150° C., more preferably 0° C. to 100° C.

The reaction time of the acylation reaction varies depending on the reaction conditions, and is preferably 5 minutes to 72 hours, more preferably 30 minutes to 48 hours.

Step 30

The cyclization reaction of Compound (XV) is usually performed in a solvent in the presence of an ammonium salt and, as the solvent, a solvent that does not inhibit the reaction is appropriately selected. Examples of the solvent that does not inhibit the reaction include acetic acid and formic acid. A mixed solvent of these may also be used as the solvent.

Examples of the ammonium salt include commercially available reagents such as ammonium acetate, ammonium formate and ammonium carbonate.

The amount of the ammonium salt to be used is preferably 1 to 20 mol, more preferably 2 to 15 mol, with respect to 1 mol of Compound (XV).

The reaction temperature of the cyclization reaction is preferably 0° C. to 200° C., more preferably 50° C. to 120° C.

The reaction time of the cyclization reaction varies depending on the reaction conditions, and is preferably 5 minutes to 100 hours, more preferably 30 minutes to 48 hours.

Production Method 18: Production Method of Intermediate Compound (SIIIb)

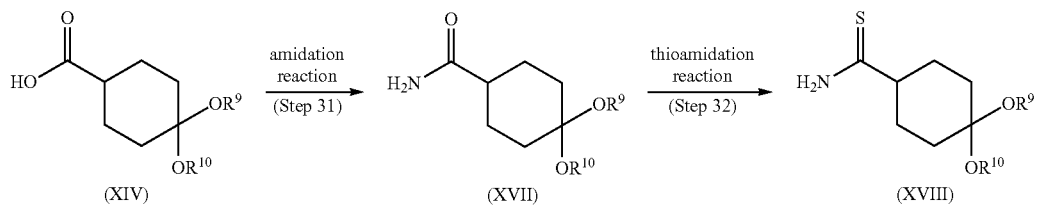

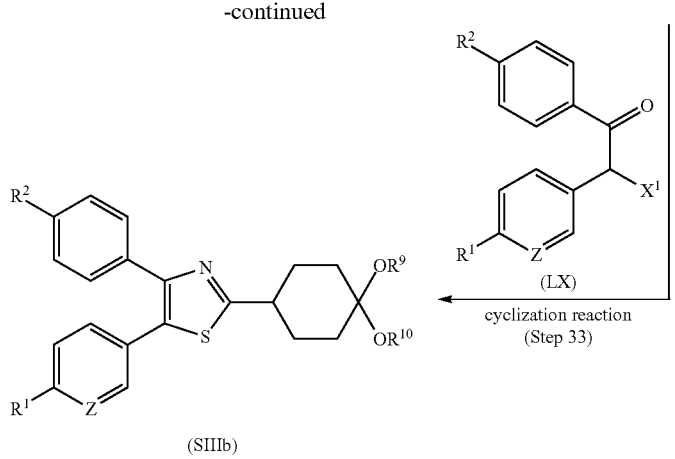

(SIIIb)

cyclization reaction
(Step 33)

wherein the symbols have the same meanings as defined above.

Compound (SIIIb) can be obtained by amidating Compound (XIV) to obtain Compound (XVII), then thioamidating it to obtain Compound (XVIII), and thereafter cyclizing it with Compound (LX). Compound (XIV) may be synthesized according to a known method. Also, Compound (LX) may be synthesized according to a known method.

Step 31

The amidation reaction of Compound (XIV) is usually performed by forming a mixed acid anhydride in a solvent in the presence of a base using a chloroformic ester or the like, and then allowing aqueous ammonia to react therewith. As the solvent, a solvent that does not inhibit the reaction is appropriately selected. Examples of the solvent that does not inhibit the reaction include ethers such as tetrahydrofuran, 1,4-dioxane and ethylene glycol dimethyl ether; halogenated hydrocarbons such as dichloromethane and chloroform; and N,N-dimethylformamide. A mixed solvent of these may also be used as the solvent.

Examples of the chloroformic ester include methyl chloroformate, ethyl chloroformate, isopropyl chloroformate and sec-butyl chloroformate.

The amount of the chloroformic ester to be used is preferably 0.5 to 4 mol, more preferably 0.9 to 2 mol, with respect to 1 mol of Compound (XIV).

Examples of the base include inorganic bases such as sodium hydrogen carbonate, sodium carbonate, potassium carbonate and cesium carbonate; and organic bases such as triethylamine, diisopropylethylamine and pyridine.

The amount of the base to be used is preferably 0.5 to 5 mol, more preferably 0.9 to 2.5 mol, with respect to 1 mol of Compound (XIV).

As for the reaction temperature of the amidation reaction, the formation of a mixed acid anhydride is carried out preferably at −78° C. to 200° C., more preferably at −20° C. to 100° C., and the reaction after adding aqueous ammonia is carried out preferably at −78° C. to 200° C., more preferably at −20° C. to 100° C.

The reaction time of the amidation reaction varies depending on the reaction conditions; and the formation of a mixed acid anhydride is carried out preferably for 5 minutes to 48 hours, more preferably for 30 minutes to 24 hours, and the reaction after adding aqueous ammonia is carried out preferably for 5 minutes to 72 hours, more preferably 30 minutes to 48 hours.

Step 32

The thioamidation reaction of Compound (XVII) is usually performed by reacting Compound (XVII) with a commercially available reagent such as Lawesson's reagent, phosphorus pentasulfide or the like in a solvent. As the solvent, a solvent that does not inhibit the reaction is appropriately selected. Examples of the solvent that does not inhibit the reaction include saturated hydrocarbons such as benzene and toluene; halogenated solvents such as dichloromethane and chloroform; and ethers such as tetrahydrofuran and 1,4-dioxane. A mixed solvent of these may also be used as the solvent.

The amount of the Lawesson's reagent, phosphorus pentasulfide or the like to be used is preferably 0.3 to 4 mol, more preferably 0.4 to 2 mol, with respect to 1 mol of Compound (XVII).

The reaction temperature of the thioamidation reaction is preferably −20° C. to 200° C., more preferably 0° C. to 120° C.

The reaction time of the thioamidation reaction varies depending on the reaction conditions, and is preferably 5 minutes to 72 hours, more preferably 30 minutes to 48 hours.

Step 33

The cyclization reaction of Compound (XVIII) is usually performed in an appropriately selected solvent that does not inhibit the reaction. Examples of the solvent that does not inhibit the reaction include alcohols such as methanol and ethanol; ethers such as tetrahydrofuran and 1,4-dioxane; and acetonitrile. A mixed solvent of these may also be used as the solvent.

The amount of Compound (LX) to be used is preferably 0.5 to 4 mol, more preferably 0.9 to 1.5 mol, with respect to 1 mol of Compound (XVIII).

The reaction temperature of the cyclization reaction is preferably −20° C. to 200° C., more preferably 0° C. to 100° C.

The reaction time of the cyclization reaction varies depending on the reaction conditions, and is preferably 5 minutes to 72 hours, more preferably 30 minutes to 48 hours.

In cases where Compound (I) was obtained in a free form, it may be converted to a desired salt according to a known method or a method similar thereto. Conversely, in cases where it was obtained as a salt, it may be converted to a free form or another desired salt according to a known method or a method similar thereto.

Compound (I) may be used in a prodrug form. Examples of such a prodrug of Compound (I) include compounds which will be changed into Compound (I) by reaction with an enzyme, gastric acid or the like under physiological conditions in a living body; that is, compounds which will be changed into Compound (I) through enzymatic oxidation, reduction, hydrolysis or the like, and compounds having a structure in which a hydroxyl group(s) of Compound (I) is(are) acylated, alkylated, phosphorylated and/or borated, which compounds will be changed into Compound (I) of the present invention through hydrolysis or the like by gastric acid or the like. Preferred specific examples of the prodrug of Compound (I) are shown in Table 2, but our therapeutic agents are not limited by these.

TABLE 2

| Compoun- | Structural Formula |
|---|---|
| 59 | |
| 60 | |
| 61 | |
| 62 | |

TABLE 2-continued
| Compoun- | Structural Formula |
|---|---|
| 63 | 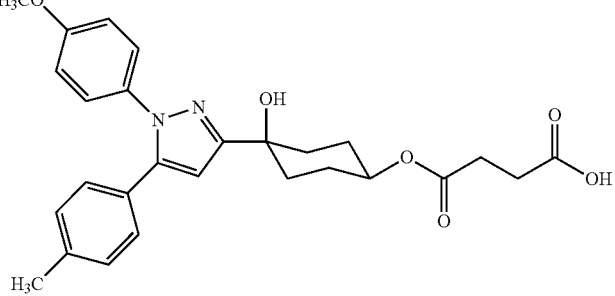 |
| 64 | 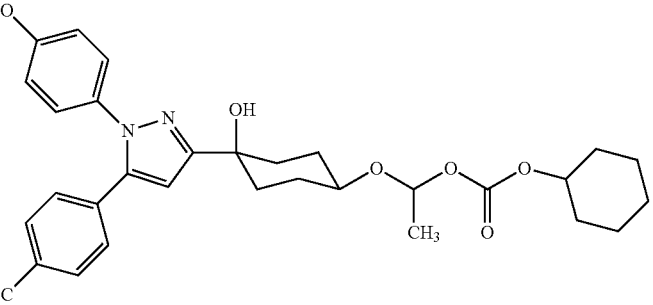 |
| 65 | 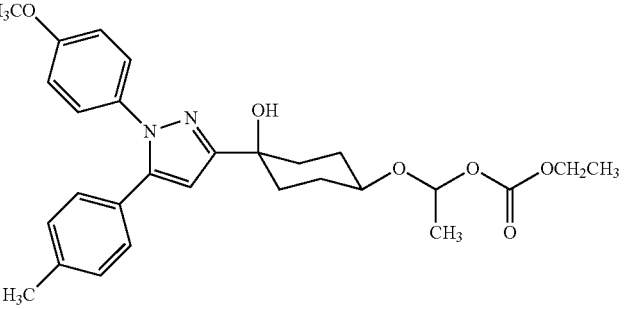 |
| 66 | 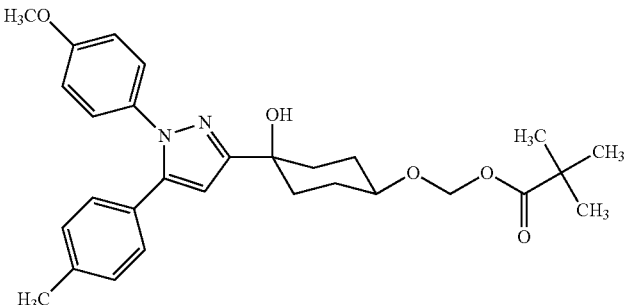 |
| 67 | 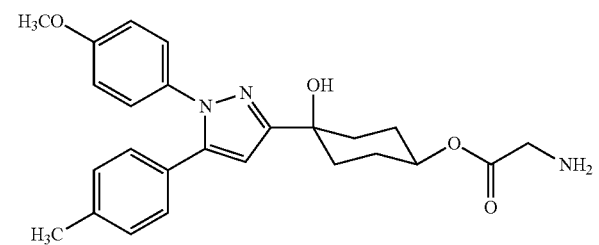 |

TABLE 2-continued

| Compoun- | Structural Formula |
|---|---|
| 68 | |
| 69 | |
| 70 | |

The prodrug of Compound (I) can be synthesized from Compound (I) according to a known method. The prodrug of Compound (I) may be those which will be changed into Compound (I) under the physiological conditions described in "Iyakuhin no Kaihatsu (Development of Pharmaceuticals)," Hirokawa Shoten, 1990, Vol. 7, p. 163-198; and Prog. Med. 5, 1985, p. 2157-2161.

A pharmaceutical comprising Compound (I) shows an excellent therapeutic effect on Alzheimer's disease also in cases where it is administered to a mammal other than human. Examples of the mammal other than human include mouse, rat, hamster, rabbit, cat, dog, bovine, sheep and monkey.

As a mode of administration of Compound (I), Compound (I) may be administered orally or parenterally as it is or after blending it with a pharmaceutically acceptable carrier(s).

In cases where a formulation comprising Compound (I) is orally administered, examples of the dosage form include tablets (including sugar coated tablets and film coated tablets), pills, granules, powders, capsules (including soft capsules and microcapsules), syrups, emulsions and suspensions. In cases where it is parenterally administered, examples of the dosage form include injection solutions, impregnating agents, drops and suppositories. It is also useful to combine the formulation with an appropriate base (for example, a polymer of butyric acid, a polymer of glycolic acid, a copolymer of butyric acid-glycolic acid, a mixture of a polymer of butyric acid and a polymer of glycolic acid, or a polyglycerol fatty acid ester) to form a sustained release formulation.

Preparation of the formulation which comprises Compound (I) and is in the above-mentioned dosage form may be carried out according to a known production method commonly used in the field of formulation of pharmaceuticals. In this case, the formulation may be produced such that an excipient, a binder, a lubricant, a disintegrator, a sweetener, a surfactant, a suspending agent, an emulsifier and/or the like which is(are) commonly used in the field of formulation of pharmaceuticals is(are) contained therein as required.

Preparation of a tablet comprising Compound (I) may be carried out such that an excipient, a binder, a disintegrator, a lubricant and/or the like is(are) contained therein; and preparation of a pill or a granule may be carried out such that an excipient, a binder, a disintegrator and/or the like is(are) contained therein. Preparation of a powder or a capsule may be carried out such that an excipient and/or the like is(are) contained therein; preparation of a syrup may be carried out such that a sweetener and/or the like is(are) contained therein; and preparation of an emulsion or a suspension may be carried out such that a surfactant, a suspending agent, an emulsifier and/or the like is(are) contained therein.

Examples of the excipient include lactose, glucose, starch, sucrose, microcrystalline cellulose, powdered glycyrrhiza, mannitol, sodium hydrogen carbonate, calcium phosphate and calcium sulfate.

Examples of the binder include a starch paste solution, a gum arabic solution, a gelatin solution, a tragacanth solution, a carboxymethylcellulose solution, a sodium alginate solution and glycerin.

Examples of the disintegrator include starch and calcium carbonate.

Examples of the lubricant include magnesium stearate, stearic acid, calcium stearate and purified talc.

Examples of the sweetener include glucose, fructose, invert sugar, sorbitol, xylitol, glycerin and simple syrup.

Examples of the surfactant include sodium lauryl sulfate, polysorbate 80, sorbitan monofatty acid ester and polyoxyl 40 stearate.

Examples of the suspending agent include gum arabic, sodium alginate, sodium carboxymethylcellulose, methylcellulose and bentonite.

Examples of the emulsifier include gum arabic, tragacanth, gelatin and polysorbate 80.

In addition, in cases where the formulation comprising Compound (I) is formulated into the above-mentioned dosage form, a colorant, a preservative, an aromatic, a corrigent, a stabilizer, a thickener and/or the like which is(are) commonly used in the field of formulation of pharmaceuticals may be added therein.

The daily dose of the formulation varies depending on the conditions and the body weight of the patient, type of the compound, administration route and/or the like. For example, in the case of oral administration, it is preferred that administration be carried out at an amount of 1 mg to 1000 mg per adult (body weight: about 60 kg), once or up to three times dividedly. In the case of parenteral administration, it is preferred that, if the formulation is injection solution, administration be carried out at an amount of 0.01 to 100 mg per 1 kg of body weight by intravenous injection.

The therapeutic agent or prophylactic agent for Alzheimer's disease may be used in combination with other therapeutic agent(s) or prophylactic agent(s) for Alzheimer's disease and/or a therapeutic agent(s) or prophylactic agent(s) for symptoms of cognitive disability in Alzheimer's disease patients.

Examples of other therapeutic agent or prophylactic agent for Alzheimer's disease include cholinesterase inhibitors such as Donepezil, Rivastigmine, Galantamine and Tacrine; NMDA receptor antagonists such as Memantine; and the like.

Examples of the therapeutic agent or prophylactic agent for symptoms of cognitive disability in Alzheimer's disease patients include antidepressants such as Amitriptyline, Fluoxetine, Clomipramin, Citalopram, Fluvoxamine, Imipramine, Maprotiline, Moclobemide, Paroxetine and Mirtazapine; therapeutic agents for schizophrenia such as Chlorpromazine, Trifluoperazine, Acetophenazine, Haloperidol, Thiothixene, Olanzapine, Risperidone, Clozapine, Quetiapine, Aripiprazole and Ziprasidone; antidepressants used for agitation and aggressive behaviors such as Carbamazepine, Valproate, Trazodone and Divalproex; benzodiazepine drugs such as Lorazepam; and the like.

EXAMPLES

Our therapeutic agents will now be described practically by way of examples thereof, but this disclosure is not restricted thereto.

Effects in Alzheimer's Disease Model Rats

In the experiments, 10 male Wistar rats of 7 weeks old were used for one experimental group. Rats were anesthetized and fixed in a brain stereotaxic apparatus. The skull of each rat was exposed, and small windows were made at two sites: 1.4 mm posterior to the bregma and 2.8 mm left and right of the midline. A catheter was inserted from the exposed dura mater into the basal ganglia located at 7.6 mm in a ventral direction, and ibotenic acid solution prepared by dissolving 5 μg ibotenic acid in 0.5 μL phosphate buffer (50 mM) was injected over 5 minutes to destroy the basal ganglia, thereby preparing Alzheimer's disease model rats. Rats of sham operation group received injection of 0.5 μL phosphate buffer (50 mM) instead of ibotenic acid solution. The basal ganglia are nuclei of origin of acetylcholine neurons which project to the cerebral cortex and play a critical role in learning and memory function, and it is known that aberrant functioning of acetylcholine neurons leads to learning and memory dysfunction in rats whose basal ganglia have been destroyed (Shinoda et al., Behay. Brain Res., 1999, vol. 99, p. 17).

Learning and memory function of the subject rats were evaluated by the Morris water maze test. Specifically, a round pool with a diameter of 150 cm, a height of 45 cm and a depth of 30 cm was provided, and a colorless, transparent platform with a diameter of 12 cm was arranged at about 1 cm below water surface. The water temperature of the round pool was set at 23±1° C. The illuminations of the room where the round pool was provided were indirect lighting, and visual cues (calendar, desk, personal computer) for the subject rats were arranged around the round pool. The arrangement of these visual cues was not changed at all during the test period. The swimming time until a subject rat placed at the arbitrary start position in the round pool reached the platform (hereinafter "Escape latency") was measured by recording the movement locus of the subject rat with a video image behavioral analysis system.

The day when destruction of the basal ganglia (hereinafter "destruction treatment") was performed was taken as Day 0, and on Day 9 after destruction treatment, subject rats were made to swim in the round pool in which the platform was not arranged so that they were acclimated to water.

Measurement of the Escape latency was carried out from Day 10 to Day 12 after destruction treatment, and three trials were performed each day with 30-minute intervals. The start position was changed every trial, but the platform was arranged at the same position through all the trials. Subject rats which could not reach the platform 90 seconds after the start were allowed to stay on the platform for 30 seconds after swimming. The mean value of the Escape latencies obtained from three trials was taken as an Escape latency of each subject rat.

As a test compound, Compound 3 included in the scope of Compound (I) was used. Donepezil hydrochloric acid salt (Aricept (registered trademark) D tablets 3 mg (Eisai) was ground to be used) was used as a positive control. Compound 3 and donepezil hydrochloric acid salt were suspended in 0.5% methylcellulose solution (hereinafter "0.5% MC") to a concentration of 6 mg/mL and 0.1 mg/mL, respectively, and orally administered at an administration volume of 5 mL per 1 kg body weight. The administered dose of Compound 3 was 30 mg/kg; and as for donepezil hydrochloric acid salt, the administered dose was 0.5 mg/kg, which was reported to be effective in the Morris water maze test using rats with medial septal lesions (Ogura et al., Japanese Pharmacology & Therapeutics, Life Science Publishing, 1998, vol. 26, suppl. 6, p. S-1313).

Compound 3 and donepezil hydrochloric acid salt were administered to subject rats in accordance with the following schedule.

Day 0 after destruction treatment: 60 minutes after the destruction treatment, 0.5% MC was administered to the rats of sham operation group, vehicle-administered group and donepezil hydrochloric acid salt-administered group, and Compound 3 was administered to the rats of Compound 3-administered group.

Day 1 to Day 9 after destruction treatment: 0.5% MC was administered to the rats of sham operation group, vehicle-administered group and donepezil hydrochloric acid salt-administered group, and Compound 3 was administered to the rats of Compound 3-administered group, once per day.

Day 10 to Day 12 after destruction treatment: 60 minutes before the first trial of Morris water maze on each day, 0.5% MC was administered to the rats of sham operation group, vehicle-administered group and Compound 3-administered group, and donepezil hydrochloric acid salt was administered to the rats of donepezil hydrochloric acid salt-administered group. In addition, within 5 minutes after the third trial of Morris water maze on each day, 0.5% MC was administered to the rats of sham operation group, vehicle-administered group and donepezil hydrochloric acid salt-administered group, and Compound 3 was administered to the rats of Compound 3-administered group.

As for statistical processing, Student's t-test was performed if the variances were found to be equal by F-test, and Aspin-Welch test was performed if the variances were found to be unequal. A significance level of 5% (two-sided) was used.

Results are shown in FIG. 1. The horizontal axis shows the day when measurement of Escape latency in Morris water maze was carried out. Day 1 in the FIGURE corresponds to Day 10 after destruction treatment; day 2 therein corresponds to Day 11 after destruction treatment; and day 3 therein corresponds to Day 12 after destruction treatment. The vertical axis shows Escape latency (sec) (mean±standard error, N=10). The symbols *, ** and $$ in the FIGURE indicate a significant difference (*, p<0.05; **, p<0.01 (Student's t-test); $$, p<0.01 (Aspin-Welch test)) from the sham operation group ("Sham operation" in the FIGURE). The symbols ## and ! in the FIGURE indicate a significant difference (##, p<0.01 (Student's t-test); !, p<0.05 (Aspin-Welch test)) from the vehicle-administered group ("Vehicle" in the FIGURE). The symbols ++ and §§ in the FIGURE indicate a significant difference (++, p<0.01 (Student's t-test); §§, p<0.05 (Aspin-Welch test)) from the vehicle-administered group ("Vehicle" in the FIGURE). In FIG. 1, donepezil hydrochloric acid salt is expressed as "Donepezil hydrochloride."

In the sham operation group, Escape latency of the rats was shortened as a trial of Morris water maze was repeated, which indicates that the rats of sham operation group learned and memorized the position where the platform was arranged. On the other hand, in the vehicle-administered group, Escape latency of the rats was statistically significantly prolonged compared to the sham operation group, which clearly indicates that the learning and memory function was impaired in the rats of vehicle-administered group by destruction of the basal ganglia.

In the Compound 3-administered group, Escape latency of the rats was statistically significantly shortened compared to the vehicle-administered group, and found to be the same level as of the sham operation group rats and the donepezil hydrochloric acid salt-administered group rats. These results indicate that Compound (I) having a cyclohexane skeleton is effective against Alzheimer's disease.

Cholinesterase inhibitors including donepezil produce a therapeutic effect on Alzheimer's disease by inhibiting degradation of acetylcholine whose amount is reduced in the brain of Alzheimer's disease patients to increase the brain acetylcholine level. This working mechanism is also apparent from the fact confirmed by the above-described Morris water maze test that Escape latency of the rats of donepezil hydrochloric acid salt-administered group which rats received donepezil hydrochloric acid salt just before the trial was shortened to the same level as of the sham operation group rats. However, it is thought that cholinesterase inhibitors do not have an effect to inhibit or delay the progress of Alzheimer's disease although they can transiently ameliorate the symptoms of Alzheimer's disease (Blennow et al., Lancet, 2006, vol. 368, p. 387). It is also known that the effect of cholinesterase inhibitors to ameliorate the symptoms of Alzheimer's disease is gradually reduced when using them for a long period of time (Bullock et al., Int. J. Clin. Prac., 2005, vol. 59, p. 817).

The administration schedule of Compound 3 was different from that of donepezil hydrochloric acid salt, i.e., Compound 3 was administered once per day repeatedly from Day 0 after destruction treatment, but was not administered just before the trial during a period of Day 10 to Day 12 after destruction treatment. Hence, it is thought that at the time of the trials Compound 3 was not present in the bodies of the rats of Compound 3-administered group. On the other hand, considering the fact that Escape latency of Compound 3-administered group was the same level as of sham operation group, it is thought that Compound 3 has a remarkable effect to inhibit or delay the progress of Alzheimer's disease, which is different from the working mechanism of donepezil hydrochloric acid salt. Thus, the results of the above-described Morris water maze test indicate that Compound (I) having a cyclohexane skeleton can maintain a sufficient therapeutic and/or prophylactic effect on Alzheimer's disease even after long-term use of it.

Effects on Mouse Partial Sciatic Nerve Ligation Model

As a reference example, the mouse partial sciatic nerve ligation model (Seltzer model), by which neuropathic pain can be evaluated, was used to evaluate the analgesic effect of Compound (I).

Mouse models of partial sciatic nerve ligation were prepared according to Seltzer's method (Malmberg et al., Pain, 1998, vol. 76, p. 215-222). Male ICR mice of 5 weeks old were anesthetized with Sodium pentobarbital (70 mg/kg, i.p.), and thereafter, the sciatic nerve at the femoral region of the right hind limb of each mouse was exposed, and the sciatic nerve was triply ligated tightly with silk suture of 8-0 (NATSUME SEISAKUSHO) under microscope so that only half thickness of the nerve was trapped in the ligature, which mice were used as a ligation group. The mice whose sciatic nerves were exposed but not ligated were used as a sham operation group.

Evaluation of neuropathic pain (hereinafter "von Frey test") was carried out as follows. Mice were conditioned for at least 1 hour in an acryl cage for measurement (NATSUME SEISAKUSHO) placed on a wire net. Thereafter, using a filament (North Coast Medical, Inc. CA, USA) which exerted a pressure of 0.16 g, the mice were subjected to mechanical tactile stimulus by applying the filament to the plantar surface of both hindpaws 3 times, each for 3 seconds, with an interval of 3 seconds. The withdrawal response observed during each mechanical tactile stimuli was scored (0, no response; 1, showed slow and slight withdrawal response in response to the stimulation; 2, showed quick withdrawal response without flinching (shaking paws quickly and continuously) nor licking (licking paws) in response to the stimulation; 3, showed quick withdrawal response with flinching and/or licking), and the total of the scores obtained in the triplicate trials (hereinafter "total score") were used as an indicator of pain.

Seven days after the sciatic nerve ligation, test compounds were orally administered to the mice. Prior to the oral administration of the test compounds, the von Frey test was carried out to split the animals of the ligation group into vehicle groups and test compound-administered groups so that the sums of the total scores of the groups were equalized. The mice of the sham operation groups, the vehicle groups and the test compound-administered groups were subjected to the von Frey test 1 hour, 2 hours and 3 hours after oral administration of a vehicle or a test compound, and the obtained scores were used as an indicator of analgesic effect. As a vehicle of test compound solution or suspension, dimethyl sulfoxide (hereinafter "DMSO"):Tween80:distilled water (1:1:8), 27% hydroxypropyl-β-cyclodextrin (hereinafter "27% HP-β-CD") or 0.5% MC was used.

The results obtained 1 hour after oral administration of vehicles and test compounds are shown in Table 3. For evaluation of drug efficacy, data were statistically processed by the unpaired multigroup t test (adjusted by Dunnett), taking the vehicle group of each measurement time as a control.

TABLE 3

| Compound | Dose (mg/kg) (n = 5-6) | Sham Operation Group | Vehicle Group | Test Compound-Administered Group | Score Improvement % | Vehicle |
|---|---|---|---|---|---|---|
| | | | von Frey Total Score of 1 Hour after Oral Administration (Mean ± S.E.) | | | |
| 2  | 0.3 | 1.0 ± 0.5 | 5.5 ± 0.3 | 0.8 ± 0.5 | 104 | B |
| 3  | 0.3 | 0.2 ± 0.2 | 6.0 ± 0.3 | 1.2 ± 0.8 | 83  | A |
| 8  | 10  | 0.8 ± 0.2 | 5.4 ± 0.4 | 2.2 ± 0.5 | 70  | A |
| 9  | 10  | 0.2 ± 0.2 | 4.6 ± 0.5 | 1.7 ± 0.6 | 66  | A |
| 10 | 1   | 0.4 ± 0.4 | 5.4 ± 0.5 | 1.5 ± 0.5 | 78  | B |
| 15 | 10  | 0.2 ± 0.2 | 5.2 ± 0.5 | 1.0 ± 0.4 | 84  | B |
| 16 | 1   | 0.4 ± 0.2 | 4.8 ± 0.4 | 2.3 ± 0.5 | 57  | C |
| 43 | 10  | 0.8 ± 0.2 | 5.4 ± 0.4 | 0.8 ± 0.7 | 100 | A |
| 48 | 10  | 0.2 ± 0.2 | 4.8 ± 0.2 | 1.0 ± 0.5 | 83  | B |
| 54 | 10  | 0.4 ± 0.2 | 5.0 ± 0.3 | 1.2 ± 0.6 | 83  | A |
| 55 | 3   | 0.4 ± 0.2 | 4.8 ± 0.4 | 0.7 ± 0.5 | 93  | B |

Vehicle A is DMSO:Tween80:distilled water = 1:1:8; Vehicle B is 27% HP-β-CD; and Vehicle C is 0.5% MC.
Score Improvement = 100 − ([mean value of total scores of test compound-administered group] − [mean value of total scores of sham operation group])/([mean value of total scores of vehicle group] − [mean value of total scores of sham operation group]) × 100

The compounds listed in Table 3 all significantly decreased total scores in von Frey tests carried out using the mouse partial sciatic nerve ligation model (a significance level of less than 5%), indicating that Compound (I) having a cyclohexane skeleton is effective against neuropathic pain.

Synthesis processes of Compound (I) and source materials and intermediates thereof were described below. Those used in synthesis of intermediates but whose synthesis process was not described hereinbelow were commercially available compounds.

Solvent names in the parentheses shown in the NMR data indicate solvents used for the measurements.

JNM-AL400 nuclear magnetic resonance apparatus produced by JEOL LTD. was used to measure 400 MHz NMR spectrum. Chemical shifts were represented by δ (in ppm) using tetramethylsilane as a standard. Signals were represented by s (singlet), d (doublet), t (triplet), q (quartet), quint (quintet), sept (septet), m (multiplet), br (broad), dd (double doublet), dt (double triplet), ddd (double double doublet), dq (double quartet), td (triple doublet), tt (triple triplet), respectively. IR spectrum was measured using FT/IR-41 produced by Jasco, and ESI-MS spectrum was measured using Micromass ZQ2K produced by Waters or 1200LC/MSD produced by AgilentTechnology. Solvents used were all commercially available products. For flash chromatography, YFLC W-prep2XY produced by Yamazen was used.

Compound 1

As Compound 1, 1-(1-(4-methoxyphenyl)-5-(p-tolyl)-1H-pyrazol-3-yl)cyclohexanol:

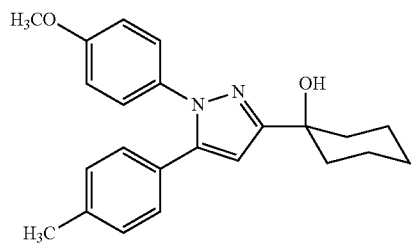

was synthesized by the following procedure.

Triethylamine (258 μL, 1.88 mmol) was added to a suspension of 4-methoxyphenylhydrazine hydrochloric acid salt (165 mg, 0.944 mmol) in ethanol (5.0 mL). The resulting mixture was stirred at room temperature for 30 minutes and then added to a solution of 3-(1-hydroxycyclohexyl)-1-(p-tolyl)-2-propyn-1-one (Intermediate 8) (214 mg, 0.883 mmol) in ethanol (3.0 mL), followed by stirring the mixture at room temperature for 20 hours. The reaction solution was concentrated under reduced pressure, and distilled water was added to the residue, followed by extraction of the resulting mixture with ethyl acetate. The organic layer was dried over anhydrous magnesium sulfate, and concentrated under reduced pressure. The residue was purified by flash chromatography (silica gel, n-hexane/ethyl acetate) to obtain Compound 1 (141 mg, 0.389 mmol, 44%) as a yellow amorphous product.

$^{1}$H-NMR (400 MHz, CDCl$_{3}$) δ: 1.31-1.42 (1H, m), 1.54-2.03 (9H, m), 2.33 (3H, s), 2.52 (1H, brs), 3.81 (3H, s), 6.40 (1H, s), 6.84 (2H, d, J=8.8 Hz), 7.09 (4H, s), 7.21 (2H, d, J=8.8 Hz).

(Compound 2 and Compound 3

As Compound 2, 1-(1-(4-methoxyphenyl)-5-(p-tolyl)-1H-pyrazol-3-yl)cyclohexan-trans-1,4-diol:

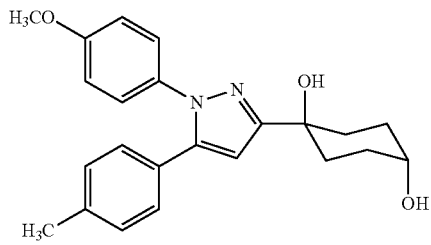

was synthesized by the following procedure. As Compound 3, 1-(1-(4-methoxyphenyl)-5-(p-tolyl)-1H-pyrazol-3-yl)cyclohexan-cis-1,4-diol:

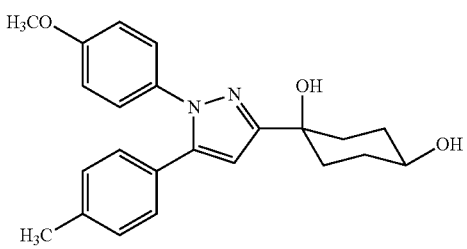

was synthesized by the following procedure.

Sodium borohydride (804 mg, 21.3 mmol) was added to a solution of 4-hydroxy-4-(1-(4-methoxyphenyl)-5-(p-tolyl)-1H-pyrazol-3-yl)-cyclohexan-1-one (Compound 4) (8.00 g, 21.3 mmol) in methanol (200 mL). The resulting mixture was stirred at room temperature for 2 hours, and thereafter poured into 1 M hydrochloric acid. The reaction solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain Compound 2 (1.66 g, 4.39 mmol, 21%) and Compound 3 (4.85 g, 12.8 mmol, 60%) as a white solid, respectively.

Compound 2: $^1$H-NMR (400 MHz, CDCl$_3$) δ: 1.36 (1H, d, J=3.6 Hz), 1.64-1.72 (2H, m), 1.77-1.83 (2H, m), 2.04-2.12 (2H, m), 2.32-2.39 (5H, m), 2.56 (1H, s), 3.81 (3H, s), 4.03-4.06 (1H, m), 6.43 (1H, s), 6.85 (2H, d, J=8.8 Hz), 7.10 (4H, s), 7.21 (2H, d, J=8.8 Hz).

IR (KBr, cm$^{-1}$): 3344, 2929, 2875, 1740, 1516, 1443, 1369, 1251, 1032, 1001, 832.

ESI-MS: m/z=379 (M+H)$^+$

Mp 151-153° C.

Anal. Calcd for C23H26N2O3: C, 72.99; H, 6.92; N, 7.40. found: C, 72.97; H, 6.92; N, 7.34.

Compound 3: $^1$H-NMR (400 MHz, CDCl$_3$) δ: 1.44 (1H, s), 1.81-1.99 (6H, m), 2.04-2.12 (2H, m), 2.33 (3H, s), 2.56 (1H, s), 3.70-3.77 (1H, m), 3.80 (3H, s), 6.37 (1H, s), 6.85 (2H, d, J=8.8 Hz), 7.09 (4H, s), 7.20 (2H, d, J=8.8 Hz).

IR (KBr, cm$^{-1}$): 3303, 2918, 1517, 1442, 1366, 1248, 1063, 1026, 837, 807.

ESI-MS: m/z=379 (M+H)$^+$

Mp 164-166° C.

Anal. Calcd for C23H26N2O3: C, 72.99; H, 6.92; N, 7.40. found: C, 72.87; H, 6.86; N, 7.22.

Compound 5 and Compound 22

As Compound 5, 1-(1-(4-chlorophenyl)-5-(p-tolyl)-1H-pyrazol-3-yl)cyclohexan-trans-1,4-diol:

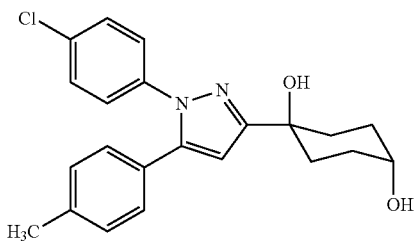

was synthesized by the following procedure. As Compound 22, 1-(1-(4-chlorophenyl)-5-(ptolyl)-1H-pyrazol-3-yl)cyclohexan-cis-1,4-diol:

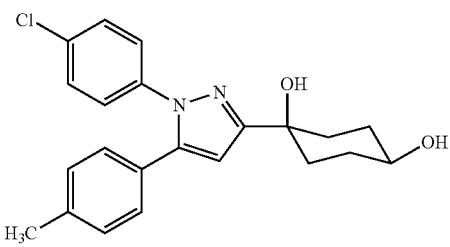

was synthesized by the following procedure.

Sodium borohydride (53 mg, 1.40 mmol) was added to a solution of 4-hydroxy-4-(1-(4-chlorophenyl)-5-(p-tolyl)-1H-pyrazol-3-yl)-cyclohexan-1-one (Intermediate 65) (510 mg, 1.34 mmol) in methanol (13 mL), and the resulting mixture was stirred at room temperature for 2 hours. The reaction solution was concentrated under reduced pressure, and thereafter dissolved in ethyl acetate, and washed with distilled water and brine. The organic layer was dried over anhydrous sodium sulfate, and concentrated under reduced pressure. The residue was purified by flash chromatography (silica gel, n-hexane/ethyl acetate) to obtain Compound 5 (114 mg, 0.298 mmol, 22%) and Compound 22 (360 mg, 0.940 mmol, 70%) as a white solid, respectively.

Compound 5: $^1$H-NMR (400 MHz, CDCl$_3$) δ: 1.36 (1H, br), 1.65-1.72 (2H, m), 1.77-1.82 (2H, m), 2.04-2.11 (2H, m), 2.31-2.38 (2H, m), 2.36 (3H, s), 2.51 (1H, s), 4.03-4.08 (1H, m), 6.44 (1H, s), 7.10 (2H, d, J=8.8 Hz), 7.13 (2H, d, J=8.8 Hz), 7.22-7.30 (4H, m).

IR (KBr, cm$^{-1}$): 3349, 2918, 1497, 1440, 1366, 1240, 1098, 1007, 969, 833, 810.

ESI-MS: m/z=383 (M+H)$^+$

Compound 22: $^1$H-NMR (400 MHz, CDCl$_3$) δ: 1.45 (1H, br), 1.80-1.99 (6H, m), 2.03-2.07 (2H, m), 2.35 (3H, s), 2.51 (1H, s), 3.70-3.80 (1H, m), 6.39 (1H, s), 7.09 (2H, d, J=8.4 Hz), 7.13 (2H, d, J=8.4 Hz), 7.21-7.24 (2H, m), 7.27-7.31 (2H, m).

IR (KBr, cm$^{-1}$): 3365, 2946, 1496, 1442, 1368, 1241, 1095, 1059, 1014, 970, 887.

ESI-MS: m/z=365 (M–OH)$^+$

Compound 6 and Compound 8

As Compound 6, 1-(1,5-bis(4-methoxyphenyl)-1H-pyrazol-3-yl)cyclohexan-trans-1,4-diol:

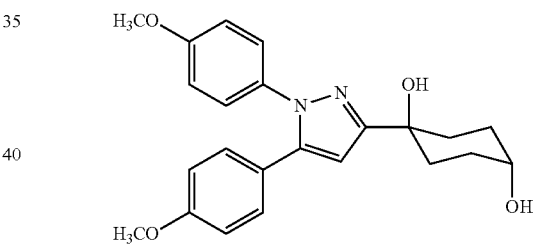

was synthesized by the following procedure. As Compound 8,1-(1,5-bis(4-methoxyphenyl)-1H-pyrazol-3-yl)cyclohexan-cis-1,4-diol:

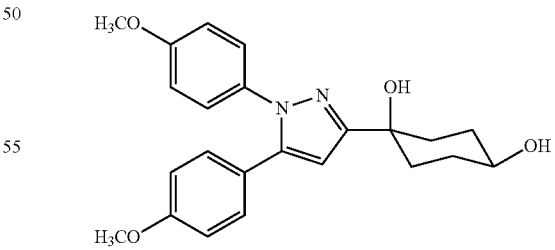

was synthesized by the following procedure.

Sodium borohydride (65 mg, 1.7 mmol) was added to a solution of 4-(1,5-bis(4-methoxyphenyl)-1H-pyrazol-3-yl)-4-hydroxy-cyclohexan-1-one (Intermediate 63) (523 mg, 1.38 mmol) in methanol, and the resulting mixture was stirred at room temperature for 1.5 hours and concentrated under reduced pressure. Distilled water was added to the residue, and the resulting solution was extracted with ethyl acetate. The organic layer was dried over anhydrous magnesium sulfate, and concentrated under reduced pressure. The residue was purified by flash chromatography to separate into low polar components and high polar components. The low polar components were purified by recrystallization (ethyl acetate/n-hexane=2/1) to obtain Compound 6 (79 mg, 0.20 mmol, 14%) as a white crystal. The high polar components were purified by recrystallization (ethyl acetate/n-hexane=2/1) to obtain Compound 8 (186 mg, 0.471 mmol, 34%) as a white crystal.

Compound 6: $^1$H-NMR (400 MHz, CDCl$_3$) δ: 1.33 (1H, d, J=3.4 Hz), 1.63-1.73 (2H, m), 1.75-1.84 (2H, m), 2.03-2.13 (2H, m), 2.30-2.39 (2H, m), 2.55 (1H, s), 3.80 (3H, s), 3.81 (3H, s), 4.02-4.08 (1H, m), 6.40 (1H, s), 6.82 (2H, d, J=8.8 Hz), 6.85 (2H, d, J=8.8 Hz), 7.14 (2H, d, J=8.8 Hz), 7.21 (2H, d, J=8.8 Hz).

IR (KBr, cm$^{-1}$): 3379, 1613, 1517, 1503, 1251, 1180, 1032, 1001, 835.

ESI-MS: m/z=395 (M+H)$^+$

Compound 8: $^1$H-NMR (400 MHz, CDCl$_3$) δ: 1.41 (1H, d, J=4.1 Hz), 1.79-2.55 (8H, m), 2.55 (1H, s), 3.69-3.78 (1H, m), 3.80 (3H, s), 3.81 (3H, s), 6.34 (1H, s), 6.81 (2H, d, J=8.8 Hz), 6.85 (2H, d, J=8.8 Hz), 7.13 (2H, d, J=8.8 Hz), 7.20 (2H, d, J=8.8 Hz).

IR (KBr, cm$^{-1}$): 3385, 1613, 1517, 1503, 1250, 1064, 1031, 970, 835.

ESI-MS: m/z=395 (M+H)$^+$

Compound 7 and Compound 21

As Compound 7, 1-(5-(4-chlorophenyl)-1-(4-methoxyphenyl)-1H-pyrazol-3-yl)cyclohexan-trans-1,4-diol:

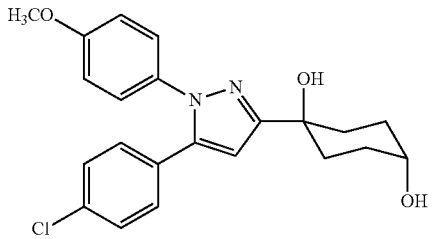

was synthesized by the following procedure. As Compound 21, 1-(5-(4-chlorophenyl)-1-(4-methoxyphenyl)-1H-pyrazol-3-yl)cyclohexan-cis-1,4-diol:

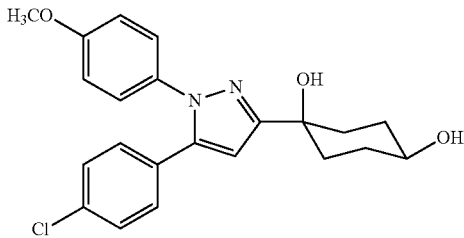

was synthesized by the following procedure.

Sodium borohydride (59.0 mg, 1.56 mmol) was added to a solution of 4-(5-(4-chlorophenyl)-1-(4-methoxyphenyl)-1H-pyrazol-3-yl)-4-hydroxy-cyclohexan-1-one (Intermediate 64) (619 mg, 1.56 mmol) in methanol (15.6 mL). The resulting mixture was stirred at room temperature for 1 hour, and thereafter poured into 1 M hydrochloric acid. The reaction solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain Compound 7 (131 mg, 0.328 mmol, 21%) and Compound 21 (291 mg, 0.730 mmol, 47%) as a white solid, respectively.

Compound 7: $^1$H-NMR (400 MHz, CDCl$_3$) δ: 1.32 (1H, d, J=3.2 Hz), 1.63-1.73 (2H, m), 1.76-1.84 (2H, m), 2.03-2.12 (2H, m), 2.30-2.39 (2H, m), 2.50 (1H, s), 3.82 (3H, s), 4.02-4.09 (1H, m), 6.46 (1H, s), 6.84-6.87 (2H, m), 7.14 (2H, d, J=8.8 Hz), 7.19 (2H, d, J=8.8 Hz), 7.26-7.28 (2H, m).

ESI-MS: m/z=399 (M+H)$^+$

Compound 21: $^1$H-NMR (400 MHz, CDCl$_3$) δ: 1.41 (1H, d, J=5.2 Hz), 1.82-2.09 (8H, m), 2.49 (1H, s), 3.70-3.78 (1H, s), 3.82 (3H, s), 6.41 (1H, s), 6.85-6.87 (2H, m), 7.13 (2H, d, J=8.4 Hz), 7.18 (2H, d, J=8.4 Hz), 7.25-7.27 (2H, m).

ESI-MS: m/z=399 (M+H)$^+$

Compound 9

As Compound 9, 1-(4-chloro-1-(4-methoxyphenyl)-5-(p-tolyl)-1H-pyrazol-3-yl)cyclohexan-cis-1,4-diol:

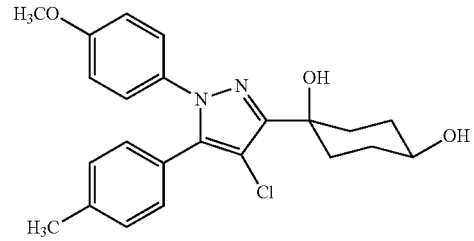

was synthesized by the following procedure.

Potassium carbonate (102 mg, 0.736 mmol) was added to a solution of 4-(4-chloro-1-(4-methoxyphenyl)-5-(p-tolyl)-1H-pyrazol-3-yl)-c-4-hydroxy-cyclohexan-r-1-yl acetate (Intermediate 81) (67 mg, 0.147 mmol) in methanol (1.5 mL), and the resulting mixture was stirred at room temperature for 2 hours. Water was added to the reaction solution to stop the reaction, and the resulting solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain Compound 9 (58 mg, 0.140 mmol, 95%) as a white solid.

$^1$H-NMR (400 MHz, CDCl$_3$) δ: 1.45 (1H, s), 1.83-2.05 (6H, m), 2.21-2.23 (2H, m), 2.36 (3H, s), 3.04 (1H, s), 3.76-3.79 (4H, m), 6.79-6.83 (2H, m), 7.11-7.16 (6H, m).

ESI-MS: m/z=395, 397 (M−OH)$^+$

Compound 10

As Compound 10, 1-(1-(4-methoxyphenyl)-5-(p-tolyl)-1H-pyrazol-3-yl)-4-(trifluoromethyl)cyclohexan-cis-1,4-diol:

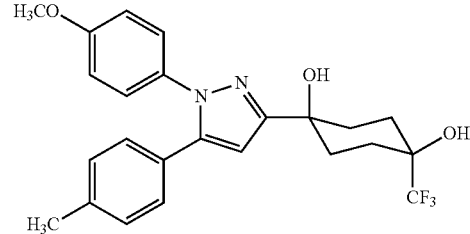

was synthesized by the following procedure.

To a solution of 4-hydroxy-4-(1-(4-methoxyphenyl)-5-(p-tolyl)-1H-pyrazol-3-yl)cyclohexan-1-one (Compound 4) (620 mg, 1.65 mmol) in tetrahydrofuran (6.60 mL), (trifluoromethyl)trimethylsilane (535 μL, 3.62 mmol) was added at 0° C. Thereafter, tetra-n-butylammonium fluoride (TBAF, 1 M solution in tetrahydrofuran) (362 μL, 0.36 mmol) was added dropwise thereto, and the obtained solution was stirred at room temperature for 6 hours. To the reaction solution, tetra-n-butylammonium fluoride (TBAF, 1 M solution in tetrahydrofuran) (3.29 mL, 3.29 mmol) was added. The resulting mixture was stirred at room temperature for 1 hour, and thereafter poured into 1 M hydrochloric acid. The reaction solution was extracted with diethyl ether. The organic layer was washed with brine, dried over anhydrous sodium sulfate, and concentrated under reduced pressure. The residue was purified by flash chromatography (silica gel, n-hexane/ethyl acetate) to obtain Compound 10 (410 mg, 0.92 mmol, 56%) as a white solid.

$^1$H-NMR (400 MHz, CDCl$_3$) δ: 1.60 (1H, s), 1.87-2.02 (4H, m), 2.09-2.02 (2H, m), 2.34-2.40 (6H, m), 3.82 (3H, s), 6.47 (1H, s), 6.86 (2H, d, J=8.8 Hz), 7.08-7.11 (4H, m), 7.20 (2H, d, J=8.8 Hz).

IR (KBr, cm$^{-1}$): 3402, 2954, 1517, 1463, 1305, 1250, 1249, 1179, 1121, 1056, 1024, 834.

ESI-MS: m/z=447 (M+H)$^+$

Compound 11

As Compound 11, t-4-fluoro-4-(1-(4-methoxyphenyl)-5-(p-tolyl)-1H-pyrazol-3-yl)cyclohexan-r-1-ol:

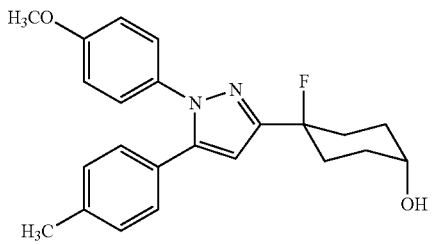

was synthesized by the following procedure.

Deoxofluor™ (48 μL, 0.262 mmol) was added to a solution of c-4-hydroxy-4-(1-(4-methoxyphenyl)-5-(p-tolyl)-1H-pyrazol-3-yl)-cyclohexan-r-1-yl acetate (Compound 12) (100 mg, 0.238 mmol) in dichloromethane (1.19 mL), and the resulting mixture was stirred at room temperature for 15 minutes. To the reaction solution, 1 M hydrochloric acid was added, and the resulting solution was extracted with chloroform. The organic layer was washed with brine, and then dried over anhydrous magnesium sulfate, and concentrated under reduced pressure to obtain a residue.

Potassium carbonate (164 mg, 1.18 mmol) was added to a solution of the obtained residue in methanol (2.4 mL), and the resulting mixture was stirred at room temperature for 2 hours. Water was added to the reaction solution to stop the reaction, and the resulting solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain Compound 11 (22.4 mg, 0.058 mmol, 25%) as a white solid.

$^1$H-NMR (400 MHz, CDCl$_3$) δ: 1.37 (1H, m), 1.72-1.77 (2H, m), 2.02-2.14 (4H, m), 2.34 (3H, s), 2.38-2.49 (2H, m), 3.81 (3H, s), 4.11 (1H, m), 6.52 (1H, m), 6.84 (2H, d, J=8.8 Hz), 7.22 (2H, d, J=8.8 Hz), 7.26 (4H, s).

ESI-MS: m/z=381 (M+H)$^+$

Compound 12

As Compound 12, c-4-hydroxy-4-(1-(4-methoxyphenyl)-5-(p-tolyl)-1H-pyrazol-3-yl)-cyclohexan-r-1-yl acetate:

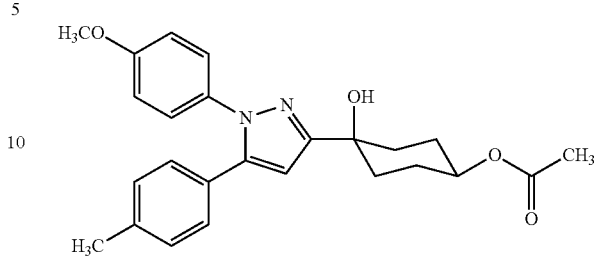

was synthesized by the following procedure.

Acetic anhydride (0.312 mL, 3.30 mmol), pyridine (0.267 mL, 3.30 mmol), and 4-dimethylaminopyridine (16.1 mg, 0.132 mmol) were added to a suspension of 1-(1-(4-methoxyphenyl)-5-(p-tolyl)-1H-pyrazol-3-yl)cyclohexan-cis-1,4-diol (Compound 3) (500 mg, 1.32 mmol) in dichloromethane (4.4 mL), and the resulting mixture was stirred at room temperature for 45 minutes. Water was added to the reaction solution to stop the reaction, and the resulting solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain Compound 12 (556 mg, 1.32 mmol, quant.) as an amorphous product.

$^1$H-NMR (400 MHz, CDCl$_3$) δ: 1.89-2.08 (11H, m), 2.34 (3H, s), 2.64 (1H, brs), 3.81 (3H, s), 4.80-4.88 (1H, m), 6.36 (1H, s), 6.85 (2H, d, J=8.8 Hz), 7.00 (4H, s), 7.20 (2H, d, J=8.8 Hz).

ESI-MS: m/z=421 (M+H)$^+$

Compound 13

As Compound 13, 4-methoxy-1-(1-(4-methoxyphenyl)-5-(p-tolyl)-1H-pyrazol-3-yl)cyclohexanol:

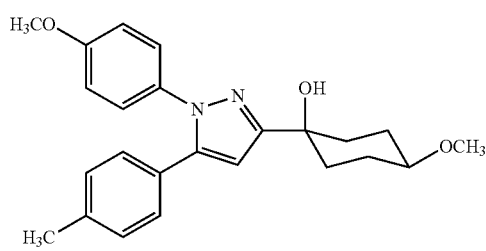

was synthesized by the following procedure.

Potassium carbonate (197 mg, 1.42 mmol) was added to a solution of c-4-methoxy-1-(1-(4-methoxyphenyl)-5-(p-tolyl)-1H-pyrazol-3-yl)-cyclohexan-r-1-yl acetate (Intermediate 39) (124 mg, 0.284 mmol) in methanol (2.8 mL), and the resulting mixture was stirred at room temperature for 18 hours. Water was added to the reaction solution to stop the reaction, and the resulting solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain Compound 13 (102 mg, 0.260 mmol, 91%) as a white amorphous product.

$^1$H-NMR (400 MHz, CDCl$_3$) δ: 1.78-1.88 (2H, m), 1.90-1.99 (4H, m), 2.03-2.09 (2H, m), 2.33 (3H, s), 2.49 (1H, s), 3.24-3.32 (1H, m), 3.39 (3H, s), 3.81 (3H, s), 6.39 (1H, s), 6.85 (2H, d, J=8.8 Hz), 7.09 (4H, s), 7.20 (2H, d, J=8.8 Hz).

IR (KBr, cm$^{-1}$): 3425, 2937, 1516, 1443, 1369, 1300, 1249, 1171, 1099, 1030, 968, 834, 801.

ESI-MS: m/z=393 (M+H)$^+$

Compound 14 and Compound 20

As Compound 14, 4-(hydroxymethyl)-4-(1-(4-methoxyphenyl)-5-(p-tolyl)-1H-pyrazol-3-yl)-trans-1,4-cyclohexanol:

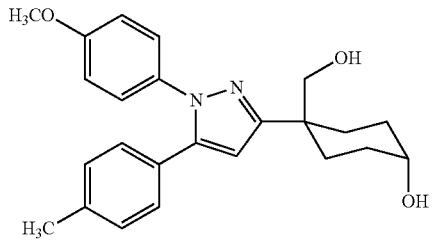

was synthesized by the following procedure. As Compound 20, 4-(hydroxymethyl)-4-(1-(4-methoxyphenyl)-5-(p-tolyl)-1H-pyrazol-3-yl)-cis-1,4-cyclohexanol:

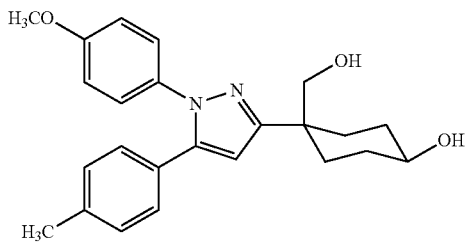

was synthesized by the following procedure.

Sodium borohydride (30.4 mg, 0.804 mmol) was added to a solution of 4-(benzyloxymethyl)-4-(1-(4-methoxyphenyl)-5-(p-tolyl)-1H-pyrazol-3-yl)cyclohexan-1-one (Intermediate 51) (387 mg, 0.804 mmol) in methanol (8.0 mL). The resulting mixture was stirred at room temperature for 1 hour, and thereafter poured into 1 M hydrochloric acid. The reaction solution was extracted with ethyl acetate. The organic layer was washed with brine, dried over anhydrous sodium sulfate, and concentrated under reduced pressure to obtain a residue.

To a solution of the obtained residue in methanol (8.0 mL), 10% palladium carbon (86.0 mg, 0.080 mmol) was added under hydrogen atmosphere, and the resulting mixture was stirred at room temperature for 3 hours. The reaction solution was filtered through Celite, and the filtrate was concentrated under reduced pressure. The residue was purified by flash chromatography (amine silica gel, n-hexane/ethyl acetate) to obtain Compound 14 (51.6 mg, 0.131 mmol, 16%) as a white solid and Compound 20 (164 mg, 0.418 mmol, 52%) as a white amorphous product.

Compound 14: $^1$H-NMR (400 MHz, CDCl$_3$) δ: 1.43 (1H, brs), 1.54-1.67 (2H, m), 1.83-1.91 (4H, m), 2.00-2.08 (2H, m), 2.34 (3H, s), 3.24-3.33 (1H, m), 3.78-3.86 (6H, m), 6.32 (1H, s), 6.84 (2H, d, J=8.8 Hz), 7.10 (4H, s), 7.19 (2H, d, J=8.8 Hz).

ESI-MS: m/z=393 (M+H)$^+$

Compound 20: $^1$H-NMR (400 MHz, CDCl$_3$) δ: 1.39 (1H, d, J=4.8 Hz), 1.46-1.60 (4H, m), 1.85-1.95 (2H, m), 2.33-2.40 (5H, m), 2.71 (1H, t, J=6.4 Hz), 3.55 (2H, d, J=6.4 Hz), 3.71-3.83 (4H, m), 6.37 (1H, s), 6.85 (2H, d, J=8.8 Hz), 7.10 (4H, s), 7.20 (2H, d, J=8.8 Hz).

ESI-MS: m/z=393 (M+H)$^+$

Compound 15

As Compound 15, 1-(1-(4-methoxyphenyl)-5-(6-methylpyridin-3-yl)-1H-pyrazol-3-yl)cyclohexan-cis-1,4-diol:

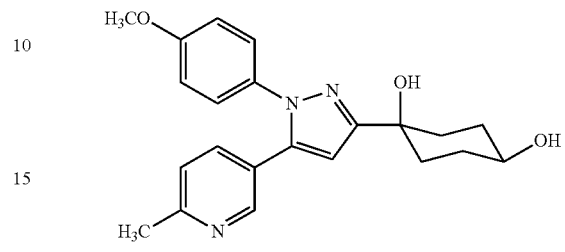

was synthesized by the following procedure.

Sodium borohydride (12.1 mg, 0.32 mmol) was added to a solution of 4-hydroxy-4-(1-(4-methoxyphenyl)-5-(6-methylpyridin-3-yl)-1H-pyrazol-3-yl)-cyclohexan-1-one (Intermediate 62) (109.5 mg, 0.29 mmol) in methanol (1.5 mL). The resulting mixture was stirred at room temperature for 40 minutes, and thereafter 1 M hydrochloric acid was added thereto. The reaction solution was washed with ethyl acetate, and the aqueous layer was basified with 1 M aqueous sodium hydroxide solution, followed by extraction of the resulting mixture twice with ethyl acetate. The organic layer was washed with brine, dried over anhydrous sodium sulfate, and concentrated under reduced pressure. The residue was purified by flash chromatography (silica gel, ethyl acetate) to obtain Compound 15 (30.6 mg, 0.81 mmol, 28%) as a white solid.

$^1$H-NMR (400 MHz, CDCl$_3$) δ: 1.59 (1H, brs), 1.81-2.00 (6H, m), 2.05-2.08 (2H, m), 2.55 (3H, s), 2.61 (1H, s), 3.71-3.78 (1H, m), 3.81 (3H, s), 6.46 (1H, s), 6.86 (2H, d, J=8.8 Hz), 7.06 (1H, d, J=8.0 Hz), 7.18 (2H, d, J=8.8 Hz), 7.32 (1H, dd, J=2.0, 8.0 Hz), 8.40 (1H, d, J=2.0 Hz).

IR (KBr, cm$^{-1}$): 3444, 2933, 2858, 1516, 1249, 1067, 968, 839.

ESI-MS: m/z=380 (M+H)$^+$

Compound 16

As Compound 16, 4-hydroxy-4-(1-(4-methoxyphenyl)-5-(p-tolyl)-1H-pyrazol-3-yl)cis-cyclohexanecarboxylic acid:

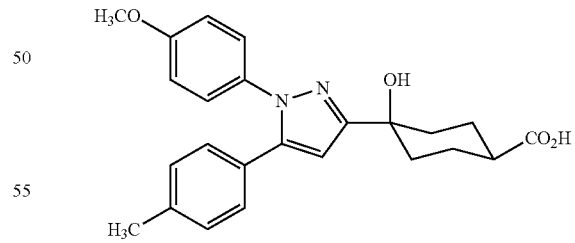

was synthesized by the following procedure.

Distilled water (0.8 ml) and 2-methyl-2-butene (101 μl, 0.96 mmol) were added to a solution of c-4-hydroxy-4-(1-(4-methoxyphenyl)-5-(p-tolyl)-1H-pyrazol-3-yl)-cis-cyclohexan-r-1-carbaldehyde (Intermediate 42) (124.9 mg, 0.32 mmol) in t-butanol (2.4 ml), and the obtained solution was cooled in ice. At 0° C., sodium dihydrogen phosphate (42.1 mg, 0.35 mmol) and sodium chlorite (72.3 mg, 0.80 mmol) were added thereto, and the obtained mixture was stirred for 5 minutes. The mixture was allowed to warm to room temperature, stirred for 1 hour, and then cooled in ice to 0° C. Thereafter, an aqueous sodium thiosulfate solution was added thereto, and the resulting mixture was stirred. To the mixture, 1 M hydrochloric acid and ethyl acetate were added, and the resulting solution was subjected to extraction. The organic layer was washed with brine, dried over anhydrous sodium sulfate, and concentrated under reduced pressure. The residue was purified by flash chromatography (silica gel, n-hexane/ethyl acetate) to obtain Compound 16 (116.6 mg, 0.29 mmol, 93%) as a white solid.

$^1$H-NMR (400 MHz, CDCl$_3$) δ: 1.87-2.11 (9H, m), 2.33 (3H, s), 2.40-2.43 (1H, m), 3.81 (3H, s), 6.38 (1H, s), 6.84 (2H, d, J=9.2 Hz), 7.09-7.09 (4H, m), 7.20 (2H, d, J=9.2 Hz).

IR (KBr, cm$^{-1}$): 3523, 2928, 1706, 1517, 1252, 831.

ESI-MS: m/z=407 (M+H)$^+$

Compound 17

As Compound 17, 4,4-difluoro-1-(1-(4-methoxyphenyl)-5-(p-tolyl)-1H-pyrazol-3-yl)cyclohexanol:

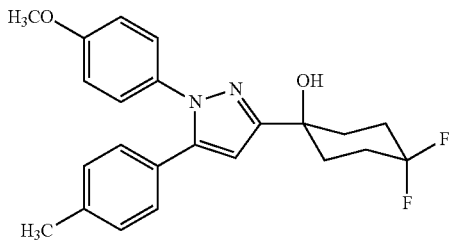

was synthesized by the following procedure.

To a solution of 1-(1-(4-methoxyphenyl)-5-(p-tolyl)-1H-pyrazol-3-yl)-4-oxo-cyclohexan-1-yl acetate (Intermediate 41) (110 mg, 0.263 mmol) in dichloromethane (2.63 mL), (dimethylamino)sulfur trifluoride (DAST) (104 μL, 0.578 mmol) was added, and the resulting mixture was stirred at room temperature for 2 hours. To the reaction solution, 1 M hydrochloric acid was added, and the resulting solution was extracted with chloroform. The organic layer was washed with brine, and then dried over anhydrous magnesium sulfate, and concentrated under reduced pressure to obtain a residue.

To a solution of the obtained residue in tetrahydrofuran (193 μL) and methanol (386 μL), a 4 M aqueous sodium hydroxide solution (193 μL, 0.772 mmol) was added, and the resulting mixture was stirred at room temperature for 6 hours. Water was added to the reaction solution to stop the reaction, and the resulting solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain Compound 17 (41.0 mg, 0.103 mmol, 39%) as a white solid.

$^1$H-NMR (400 MHz, CDCl$_3$) δ: 2.01-2.31 (8H, m), 2.34 (3H, s), 2.77 (1H, s), 3.81 (3H, s), 6.37 (1H, s), 6.86 (2H, d, J=8.8 Hz), 7.10 (4H, s), 7.21 (2H, d, J=8.8 Hz).

ESI-MS: m/z=399 (M+H)$^+$

The following compounds were synthesized in the same manner as in the synthesis of the above-described Compound 2 and Compound 3.

TABLE 4

| Compound | Structural Formula | Compound Data |
|---|---|---|
| 18 | | $^1$H-NMR (400 MHz, CDCl3) δ: 1.44 (1H, d, J = 4.0 Hz), 1.84-2.01 (8H, m), 2.48 (1H, s), 3.75 (1H, s), 3.82 (3H, s), 6.49 (1H, s), 6.87 (2H, d, J = 9.2 Hz), 7.19 (2H, d, J = 9.2 Hz), 7.32 (2H, d, J = 8.2 Hz), 7.55 (2H, d, J = 8.2 Hz). ESI-MS: m/z = 433 (M + H)$^+$ |
| 19 | | $^1$H-NMR (400 MHz, CDCl3) δ: 1.35 (1H, s), 1.67-1.71 (2H, m), 1.78-1.84 (2H, m), 2.0-2.11 (2H, m), 2.33-2.40 (2H, m), 2.49 (1H, s), 3.83 (3H, s), 4.07 (1H, m), 6.53 (1H, s), 6.87 (2H, d, J = 8.2 Hz), 7.19 (2H, d, J = 8.2 Hz), 7.33 (2H, d, J = 8.2 Hz), 7.55 (2H, d, J = 8.2 Hz). ESI-MS: m/z = 433 (M + H)$^+$ |
| 23 | | $^1$H-NMR (400 MHz, CDCl$_3$) δ: 1.34 (1H, d, J = 3.2 Hz), 1.64-1.72 (2H, m), 1.76-1.83 (2H, m), 2.03-2.12 (2H, m), 2.30-2.39 (2H, m), 2.45 (1H, s), 4.03-4.09 (1H, m), 6.48 (1H, s), 7.15 (2H, d, J = 8.8 Hz), 7.22 (2H, d, J = 8.8 Hz), 7.30-7.33 (4H, m). ESI-MS: m/z = 403 (M + H)$^+$ |

TABLE 4-continued

| Compound | Structural Formula | Compound Data |
|---|---|---|
| 24 | (structure: 1,5-bis(4-chlorophenyl)pyrazole with cyclohexane-1,4-diol at 3-position) | $^1$H-NMR (400 MHz, CDCl$_3$) δ: 1.45 (1H, d, J = 4.0 Hz), 1.80-2.07 (8H, m), 2.46 (1H, s), 3.70-3.79 (1H, s), 6.43 (1H, s), 7.14 (2H, d, J = 8.8 Hz), 7.21 (2H, d, J = 8.8 Hz), 7.29-7.33 (4H, m). ESI-MS: m/z = 403 (M + H)$^+$ |
| 25 | (structure: 1-phenyl-5-(4-chlorophenyl)pyrazole with cyclohexane-1,4-diol at 3-position) | $^1$H-NMR (400 MHz, CDCl$_3$) δ: 1.33 (1H, d, J = 3.2 Hz), 1.65-1.73 (2H, m), 1.78-1.84 (2H, m), 2.04-2.13 (2H, m), 2.32-2.40 (2H, m), 2.51 (1H, s), 4.03-4.09 (1H, m), 6.48 (1H, s), 7.14-7.16 (2H, m), 7.26-7.28 (7H, m). ESI-MS: m/z = 369 (M + H)$^+$ |
| 26 | (structure: 1-phenyl-5-(4-chlorophenyl)pyrazole with cyclohexane-1,4-diol at 3-position) | $^1$H-NMR (400 MHz, CDCl$_3$) δ: 1.43 (1H, d, J = 5.2 Hz), 1.81-2.09 (8H, m), 2.50 (1H, s), 3.71-3.79 (1H, m), 6.43 (1H, s), 7.12-7.16 (2H, m), 7.25-7.38 (7H, m). ESI-MS: m/z = 369 (M + H)$^+$ |
| 27 | (structure: 1,5-bis(4-methylphenyl)pyrazole with cyclohexane-1,4-diol at 3-position) | $^1$H-NMR (400 MHz, CDCl$_3$) δ: 1.41 (1H, brs), 1.64-1.72 (2H, m), 1.77-1.83 (2H, m), 2.04-2.11 (2H, m), 2.31-2.38 (2H, m), 2.34 (3H, s), 2.35 (3H, s), 2.59 (1H, s), 4.02-4.07 (1H, m), 6.43 (1H, s), 7.09-7.11 (4H, m), 7.12 (2H, d, J = 8.4 Hz), 7.18 (2H, d, J = 8.4 Hz). IR (KBr, cm$^{-1}$): 3343, 2918, 1518, 1440, 1367, 1266, 1240, 1196, 1159, 1107, 1007, 824, 810. ESI-MS: m/z = 363 (M + H)$^+$ |
| 28 | (structure: 1,5-bis(4-methylphenyl)pyrazole with cyclohexane-1,4-diol at 3-position) | $^1$H-NMR (400 MHz, CDCl$_3$) δ: 1.48 (1H, brs), 1.80-1.99 (6H, m), 2.02-2.09 (2H, m), 2.34 (3H, s), 2.35 (3H, s), 2.61 (1H, s), 3.70-3.78 (1H, m), 6.38 (1H, s), 7.08-7.12 (4H, m), 7.12 (2H, d, J = 8.8 Hz), 7.17 (2H, d, J = 8.8 Hz). IR (KBr, cm$^{-1}$): 3375, 2937, 2870, 1519, 1502, 1440, 1362, 1217, 1193, 1112, 1064, 1042, 1017, 973, 886, 821, 804. ESI-MS: m/z = 345 (M − OH)$^+$ |
| 29 | (structure: 1-phenyl-5-(4-methylphenyl)pyrazole with cyclohexane-1,4-diol at 3-position) | $^1$H-NMR (400 MHz, CDCl$_3$) δ: 1.47 (1H, brs), 1.64-1.73 (2H, m), 1.76-1.85 (2H, m), 2.03-2.12 (2H, m), 2.31-2.40 (2H, m), 2.34 (3H, s), 2.62 (1H, s), 4.02-4.08 (1H, m), 6.45 (1H, s), 7.08-7.14 (4H, m), 7.26-7.36 (5H, m). IR (KBr, cm$^{-1}$): 3337, 2920, 1599, 1506, 1437, 1366, 1005, 810, 765, 696. ESI-MS: m/z = 349 (M + H)$^+$ |

TABLE 4-continued

| Compound | Structural Formula | Compound Data |
|---|---|---|
| 30 | | $^1$H-NMR (400 MHz, CDCl$_3$) δ: 1.50 (1H, brs), 1.80-2.00 (6H, m), 2.03-2.09 (2H, m), 2.34 (3H, s), 2.60 (1H, s), 3.70-3.79 (1H, m), 6.40 (1H, s), 7.08-7.12 (4H, m), 7.27-7.35 (5H, m). IR (KBr, cm$^{-1}$): 3374, 2919, 1596, 1505, 1440, 1361, 1217, 1112, 1064, 1044, 1019, 973, 886, 819, 799, 771, 693. ESI-MS: m/z = 331 (M − OH)$^+$ |
| 31 | | $^1$H-NMR (400 MHz, CDCl$_3$) δ: 1.42 (1H, d, J = 4.8 Hz), 1.79-2.01 (6H, m), 2.03-2.08 (2H, m), 2.54 (1H, s), 3.71-3.80 (1H, m), 3.81 (3H, s), 6.41 (1H, s), 6.84 (2H, d, J = 6.8 Hz), 7.18-7.23 (4H, m), 7.28-7.30 (3H, m). ESI-MS: m/z = 365 (M + H)$^+$ |
| 32 | | $^1$H-NMR (400 MHz, CDCl$_3$) δ: 1.34 (1H, d, J = 3.6 Hz), 1.65-1.73 (2H, m), 1.17-1.85 (2H, m), 2.03-2.12 (2H, m), 2.32-2.40 (2H, m), 2.54 (1H, s), 3.81 (3H, s), 4.00-4.10 (1H, m), 6.46 (1H, s), 6.85 (2H, d, J = 8.8 Hz), 7.19-7.24 (4H, m), 7.28-7.31 (3H, m). ESI-MS: m/z = 365 (M + H)$^+$ |
| 33 | | $^1$H-NMR (400 MHz, CDCl$_3$) δ: 1.34 (1H, d, J = 3.6 Hz), 1.62-1.73 (2H, m), 1.77-1.85 (2H, m), 2.03-2.12 (2H, m), 2.31-2.40 (5H, m), 2.57 (1H, s), 4.00-4.08 (1H, m), 6.61 (1H, s), 7.12 (2H, d, J = 8.4 Hz), 7.17 (2H, d, J = 8.8 Hz), 7.21-7.24 (2H, m), 7.28-7.30 (3H, m). ESI-MS: m/z = 349 (M + H)$^+$ |
| 34 | | $^1$H-NMR (400 MHz, CDCl$_3$) δ: 1.79-2.00 (6H, m), 2.03-2.08 (2H, m), 2.34 (3H, s), 2.57 (1H, s), 3.70-3.79 (1H, m), 6.41 (1H, s), 7.10 (2H, d, J = 8.4 Hz), 7.16 (2H, d, J = 8.4 Hz), 7.27-7.31 (3H, m), 7.19-7.23 (2H, m). ESI-MS: m/z = 349 (M + H)$^+$ |
| 35 | | $^1$H-NMR (400 MHz, CDCl$_3$) δ: 1.35 (1H, d, J = 3.6 Hz), 1.62-1.73 (2H, m), 1.75-1.86 (2H, m), 2.02-2.13 (2H, m), 2.29-2.40 (5H, m), 2.58 (1H, s), 3.80 (3H, s), 4.01-4.09 (1H, m), 6.40 (1H, s), 6.82 (2H, d, J = 8.8 Hz), 7.10-7.20 (6H, m). |

TABLE 4-continued

| Compound | Structural Formula | Compound Data |
|---|---|---|
| 36 | | $^1$H-NMR (400 MHz, CDCl$_3$) δ: 1.34 (1H, d, J = 5.6 Hz), 1.80-2.10 (8H, m), 2.34 (3H, s), 2.59 (1H, s), 3.68-3.79 (1H, m), 3.80 (3H, s), 6.34 (1H, s), 6.81 (2H, d, J = 8.4 Hz), 7.08-7.20 (6H, m). |
| 37 | | $^1$H-NMR (400 MHz, CDCl$_3$) δ: 1.48 (1H, s), 1.62-1.72 (2H, m), 1.73-1.83 (2H, m), 2.02-2.12 (2H, m), 2.30-2.39 (2H, m), 2.57 (1H, s), 3.82 (3H, s), 4.02-4.06 (1H, m), 6.42 (1H, s), 6.84 (2H, d, J = 8.8 Hz), 7.13 (2H, d, J = 12.0 Hz), 7.23 (2H, d, J = 8.8 Hz), 7.29 (2H, d, J = 8.8 Hz).<br>ESI-MS: m/z = 399 (M + H)$^+$ |
| 38 | | $^1$H-NMR (400 MHz, CDCl$_3$) δ: 1.79-1.99 (6H, m), 2.03-2.07 (3H, m), 3.70-3.79 (1H, m), 3.81 (3H, s), 6.37 (1H, s), 6.84 (2H, d, J = 8.8 Hz), 7.14 (2H, d, J = 8.8 Hz), 7.22 (2H, d, J = 8.8 Hz), 7.29 (2H, d, J = 8.8 Hz).<br>ESI-MS: m/z = 399 (M + H)$^+$ |
| 39 | | $^1$H-NMR (400 MHz, CDCl$_3$) δ: 1.38 (1H, s), 1.64-1.74 (2H, m), 1.76-1.85 (2H, m), 2.03-2.13 (2H, m), 2.31-2.40 (2H, m), 2.58 (1H, s), 3.81 (3H, s), 4.06 (1H, s), 6.42 (1H, s), 6.82 (2H, d, J = 8.8 Hz), 7.14 (2H, d, J = 8.8 Hz), 7.28-7.37 (5H, m).<br>ESI-MS: m/z = 365 (M + H)$^+$ |
| 40 | | $^1$H-NMR (400 MHz, CDCl$_3$) δ: 1.47 (1H, s), 1.79-1.99 (6H, m), 2.03-2.07 (2H, m), 2.59 (1H, s), 3.70-3.79 (1H, m), 3.80 (3H, s), 6.37 (1H, s), 6.82 (2H, d, J = 8.6 Hz), 7.13 (2H, d, J = 8.6 Hz), 7.27-7.36 (5H, m).<br>ESI-MS: m/z = 365 (M + H)$^+$ |

Compound 41 and Compound 42

As Compound 41, 1-(4-(4-methoxyphenyl)-5-(p-tolyl)thiazol-2-yl)cyclohexan-trans-1,4-diol:

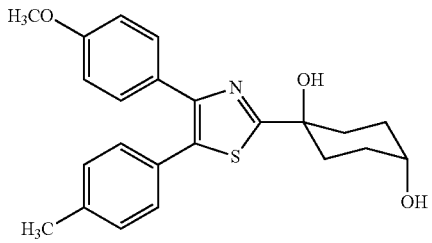

was synthesized by the following procedure. As Compound 42, 1-(4-(4-methoxyphenyl)-5-(ptolyl)thiazol-2-yl)cyclohexan-cis-1,4-diol:

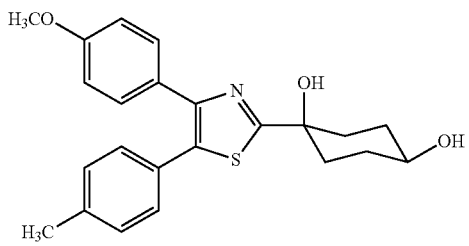

was synthesized by the following procedure.

Sodium borohydride (36 mg, 0.943 mmol) was added to a solution of 4-hydroxy-4-(4-(4-methoxyphenyl)-5-(p-tolyl)thiazol-2-yl)cyclohexan-1-one (Intermediate 83) (186 mg, 0.471 mmol) in methanol (4.7 mL), and the resulting mixture was stirred at room temperature for 1 hour. The reaction solution was concentrated under reduced pressure, and thereafter dissolved in ethyl acetate, and washed with distilled water and brine. The organic layer was dried over anhydrous sodium sulfate, and concentrated under reduced pressure. The residue was purified by flash chromatography (silica gel, n-hexane/ethyl acetate) to obtain Compound 41 (42 mg, 0.106 mmol, 23%) and Compound 42 (136 mg, 0.344 mmol, 73%) as a white solid, respectively.

Compound 41: $^1$H-NMR (400 MHz, CDCl$_3$) δ: 1.53-1.57 (1H, m), 1.76-1.87 (4H, m), 2.05-2.12 (2H, m), 2.35-2.42 (2H, m), 2.36 (3H, s), 3.15 (1H, br), 3.80 (3H, s), 4.10-4.14 (1H, m), 6.80-6.84 (2H, m), 7.13 (2H, d, J=8.0 Hz), 7.24 (2H, d, J=8.0 Hz), 7.45-7.49 (2H, m).

IR (KBr, cm$^{-1}$): 3409, 2923, 1613, 1515, 1252, 1179, 1004, 815.

ESI-MS: m/z=396 (M+H)$^+$

Compound 42: $^1$H-NMR (400 MHz, CDCl$_3$) δ: 1.48 (1H, d, J=4.8 Hz), 1.82-1.89 (2H, m), 1.95-2.01 (2H, m), 2.05-2.09 (4H, m), 2.36 (3H, s), 3.01 (1H, s), 3.76-3.82 (1H, m), 3.80 (3H, s), 6.80-6.83 (2H, m), 7.13 (2H, d, J=8.0 Hz), 7.22 (2H, d, J=8.0 Hz), 7.43-7.47 (2H, m).

IR (KBr, cm$^{-1}$): 3418, 2938, 1611, 1515, 1249, 1177, 1058, 816.

ESI-MS: m/z=396 (M+H)$^+$

Compound 43 and Compound 44

As Compound 43, 4-(4,5-bis(4-methoxyphenyl)oxazol-2-yl)cyclohexan-cis-1,4-diol:

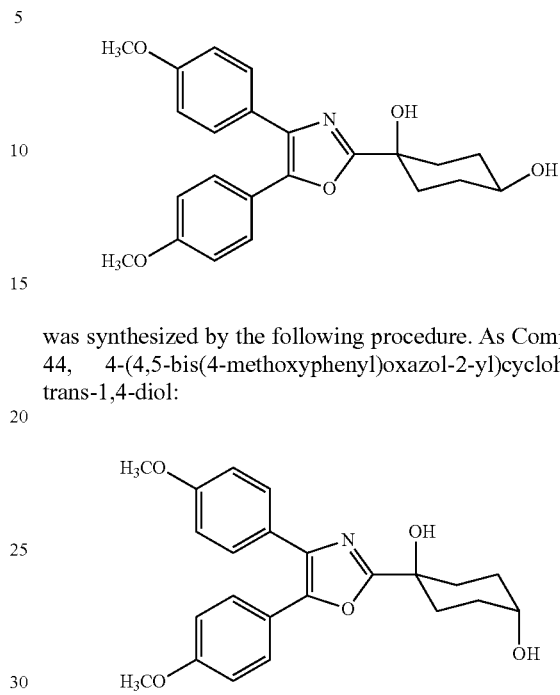

was synthesized by the following procedure. As Compound 44, 4-(4,5-bis(4-methoxyphenyl)oxazol-2-yl)cyclohexan-trans-1,4-diol:

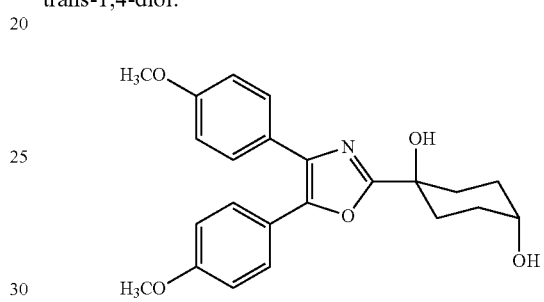

was synthesized by the following procedure.

Sodium borohydride (47 mg, 1.24 mmol) was added to a solution of 4-(4,5-bis(4-methoxyphenyl)oxazol-2-yl)-4-hydroxycyclohexan-1-one (Intermediate 82) (395 mg, 1.00 mmol) in methanol (20 mL), and the resulting mixture was stirred at room temperature for 16 hours. The reaction solution was concentrated under reduced pressure, and distilled water was added to the residue, followed by extraction of the resulting mixture with ethyl acetate. The organic layer was dried over anhydrous magnesium sulfate, and concentrated under reduced pressure. The residue was purified by flash chromatography (silica gel, n-hexane/ethyl acetate) to obtain Compound 43 (207 mg, 0.523 mmol, 52%) and Compound 44 (73 mg, 0.18 mmol, 18%) as a white solid, respectively.

Compound 43: $^1$H-NMR (400 MHz, CDCl$_3$) δ: 1.49 (1H, brs), 1.78-2.13 (8H, m), 2.76 (1H, s), 3.72-3.78 (1H, m), 3.83 (6H, s), 6.89 (2H, d, J=8.8 Hz), 6.90 (2H, d, J=8.8 Hz), 7.49 (2H, d, J=8.8 Hz), 7.55 (2H, d, J=8.8 Hz).

IR (KBr, cm$^{-1}$): 3364, 1615, 1599, 1520, 1500, 1302, 1252, 1176, 1069, 1053, 1028, 965, 833.

ESI-MS: m/z=396 (M+H)$^+$

Compound 44: $^1$H-NMR (400 MHz, CDCl$_3$) δ: 1.63-1.75 (2H, m), 1.78-1.88 (2H, m), 2.01-2.12 (2H, m), 2.44-2.53 (2H, m), 2.67 (1H, s), 4.00-4.07 (1H, m), 6.89 (2H, d, J=8.8 Hz), 6.90 (2H, d, J=8.8 Hz), 7.51 (2H, d, J=8.8 Hz), 7.57 (2H, d, J=8.8 Hz).

IR (KBr, cm$^{-1}$): 3356, 1613, 1600, 1520, 1503, 1254, 1182, 1033, 999, 966, 834.

ESI-MS: m/z=396 (M+H)$^+$

Compound 45 and Compound 46

As Compound 45, 1-(4-(4-methoxyphenyl)-5-(p-tolyl)thiazol-2-yl)-4-(trifluoromethyl)cyclohexan-trans-1,4-diol:

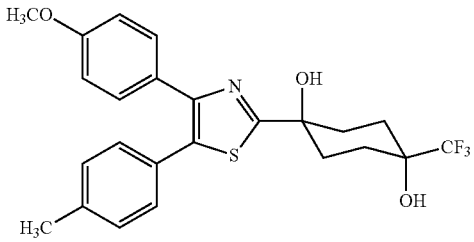

was synthesized by the following procedure. As Compound 46, 1-(4-(4-methoxyphenyl)-5-(ptolyl)thiazol-2-yl)-4-(trifluoromethyl)cyclohexan-cis-1,4-diol:

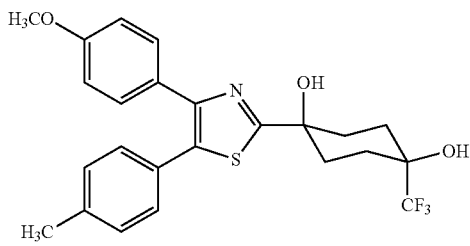

was synthesized by the following procedure.

To a solution of 4-hydroxy-4-(4-(4-methoxyphenyl)-5-(p-tolyl)thiazol-2-yl)cyclohexan-1-one (Intermediate 83) (199 mg, 0.506 mmol) and Ruppert's reagent (0.187 mL, 1.26 mmol) in tetrahydrofuran (2.5 mL), a 1.0 M tetrabutylammonium fluoride/tetrahydrofuran solution (0.051 mL, 0.051 mmol) was added at room temperature, and the resulting mixture was stirred for 10 minutes. The reaction solution was concentrated under reduced pressure, and thereafter dissolved in tetrahydrofuran (3.0 mL). Distilled water (0.2 mL) and a 1.0 M tetrabutylammonium fluoride/tetrahydrofuran solution (1.02 mL, 1.02 mmol) were added thereto, and the resulting mixture was stirred at room temperature for 30 minutes. Distilled water was added to the reaction solution, and the resulting solution was extracted with ethyl acetate, followed by washing with brine. The organic layer was dried over anhydrous sodium sulfate, and concentrated under reduced pressure. The residue was purified by flash chromatography (silica gel, n-hexane/ethyl acetate) to obtain Compound 45 (70 mg, 0.151 mmol, 30%) and Compound 46 (132 mg, 0.285 mmol, 56%) as a white solid, respectively.

Compound 45: $^1$H-NMR (400 MHz, CDCl$_3$) δ: 1.79-1.84 (2H, m), 1.90 (1H, s), 1.96-2.01 (2H, m), 2.21-2.33 (4H, m), 2.37 (3H, s), 3.28 (1H, s), 3.80 (3H, s), 6.80-6.84 (2H, m), 7.13 (2H, d, J=8.0 Hz), 7.23 (21-1, d, J=8.0 Hz), 7.44-7.48 (2H, m).

IR (KBr, cm$^{-1}$): 3460, 2940, 1610, 1515, 1494, 1442, 1310, 1245, 1175, 1035, 1005, 837, 813

ESI-MS: m/z=464 (M+H)$^+$

Compound 46: $^1$H-NMR (400 MHz, CDCl$_3$) δ: 1.90-1.96 (2H, m), 1.97 (1H, br), 2.16-2.23 (2H, m), 2.28-2.36 (4H, m), 2.37 (3H, s), 2.81 (1H, br), 3.80 (3H, s), 6.80-6.83 (2H, m), 7.14 (2H, d, J=8.0 Hz), 7.26 (2H, d, J=8.0 Hz), 7.44-7.48 (2H, m).

IR (KBr, cm$^{-1}$): 3419, 2940, 1611, 1515, 1443, 1290, 1250, 1175, 1120, 1066, 993, 837, 814

ESI-MS: m/z=464 (M+H)$^+$

The following compounds were synthesized in the same manner as in the synthesis of the above-described Compound 2 and Compound 3.

TABLE 5

| Compound | Structural Formula | Compound Data |
|---|---|---|
| 47 | ![structure] | $^1$H-NMR (400 MHz, CDCl3) δ: 1.23 (3H, t, J = 7.6 Hz), 1.33 (1H, br), 1.64-1.73 (2H, m), 1.77-1.84 (2H, m), 2.03-2.12 (2H, m), 2.31-2.40 (2H, m), 2.55 (1H, s), 2.63 (2H, q, J = 7.6 Hz), 3.81 (3H, s), 4.02-4.07 (1H, m), 6.43 (1H, s), 6.83-6.89 (2H, m), 7.12 (4H, s), 7.19-7.28 (2H, m). ESI-MS: m/z = 393 (M + H)$^+$ |
| 48 | ![structure] | $^1$H-NMR (400 MHz, CDCl3) δ: 1.23 (3H, t, J = 7.6 Hz), 1.41 (1H, d, J = 4.4 Hz), 1.80-2.09 (8H, m), 2.55 (1H, s), 2.63 (2H, q, J = 7.6 Hz), 3.69-3.83 (4H, m), 6.38 (1H, s), 6.82-6.87 (2H, m), 7.12 (4H, s), 7.17-7.28 (2H, m). ESI-MS: m/z = 393 (M + H)$^+$ |

TABLE 5-continued

| Compound | Structural Formula | Compound Data |
| --- | --- | --- |
| 49 | | $^1$H-NMR (400 MHz, CDCl$_3$) δ: 1.33 (1H, br), 1.65-1.82 (4H, m), 2.03-2.12 (2H, m), 2.30-2.39 (5H, m), 2.43 (1H, s), 4.03-4.11 (1H, m), 6.48 (1H, s), 7.10-7.19 (4H, m), 7.41-7.45 (2H, m), 7.57-7.61 (2H, m). ESI-MS: m/z = 374 (M + H)$^+$ |
| 50 | | $^1$H-NMR (400 MHz, CDCl$_3$) δ: 1.45 (1H, br), 1.81-2.07 (8H, m), 2.38 (3H, s), 2.45 (1H, br), 3.70-3.80 (1H, m), 6.43 (1H, s), 7.09-7.18 (4H, m), 7.40-7.44 (2H, m), 7.57-7.61 (2H, m). ESI-MS: m/z = 374 (M + H)$^+$ |
| 51 | | $^1$H-NMR (400 MHz, CDCl$_3$) δ: 1.62-1.90 (4H, m), 2.02-2.16 (2H, m), 2.31-2.49 (3H, m), 3.83 (3H, s), 4.03-4.11 (1H, m), 6.55 (1H, s), 6.86-6.90 (2H, m), 7.16-7.22 (2H, m), 7.29-7.33 (2H, m), 7.53-7.60 (2H, m). ESI-MS: m/z = 390 (M + H)$^+$ |
| 52 | | $^1$H-NMR (400 MHz, CDCl$_3$) δ: 1.43 (1H, br), 1.80-2.10 (8H, m), 2.43 (1H, s), 3.70-3.80 (1H, m), 3.83 (3H, s), 6.51 (1H, s), 6.85-6.91 (2H, m), 7.15-7.21 (2H, m), 7.27-7.33 (2H, m), 7.55-7.61 (2H, m). ESI-MS: m/z = 390 (M + H)$^+$ |
| 53 | | $^1$H-NMR (400 MHz, CDCl$_3$) δ: 1.32 (1H, br), 1.65-1.72 (2H, m), 1.77-1.83 (2H, m), 2.04-2.11 (2H, m), 2.30-2.39 (5H, m), 2.48 (1H, br), 3.89 (3H, s), 4.02-4.08 (1H, m), 6.43 (1H, s), 6.88 (1H, t, J = 8.8 Hz), 6.93-7.02 (1H, m), 7.08-7.15 (5H, m). ESI-MS: m/z = 397 (M + H)$^+$ |
| 54 | | $^1$H-NMR (400 MHz, CDCl$_3$) δ: 1.41 (1H, br), 1.80-2.08 (8H, m), 2.35 (3H, s), 2.48 (1H, s), 3.70-3.80 (1H, m), 3.89 (3H, s), 6.38 (1H, s), 6.88 (1H, t, J = 8.8 Hz), 6.96-7.01 (1H, m), 7.06-7.14 (5H, m). ESI-MS: m/z = 397 (M + H)$^+$ |

TABLE 5-continued

| Compound | Structural Formula | Compound Data |
| --- | --- | --- |
| 55 | | ¹H-NMR (400 MHz, CDCl₃) δ: 1.63-1.84 (4H, m), 2.03-2.12 (2H, m), 2.26 (3H, d, J = 1.6 Hz), 2.31-2.41 (2H, m), 2.51 (1H, br), 3.82 (3H, s), 4.03-4.08 (1H, m), 6.44 (1H, s), 6.84-6.90 (4H, m), 7.08 (1H, t, J = 8.0 Hz), 7.18-7.23 (2H, m). ESI-MS: m/z = 397 (M + H)⁺ |
| 56 | | ¹H-NMR (400 MHz, CDCl₃) δ: 1.41 (1H, d, J = 4.8 Hz), 1.81-2.08 (8H, m), 2.25 (3H, d, J = 1.6 Hz), 2.51 (1H, s), 3.69-3.78 (1H, m), 3.82 (3H, s), 6.39 (1H, s), 6.84-6.89 (4H, m), 7.09 (1H, t, J = 7.6 Hz), 7.17-7.24 (2H, m). ESI-MS: m/z = 397 (M + H)⁺ |

Compound 58

As Compound 58, ethyl 4-hydroxy-4-(1-(4-methoxyphenyl)-5-(p-tolyl)-1H-pyrazol-3-yl)-cis-cyclohexanecarboxylate:

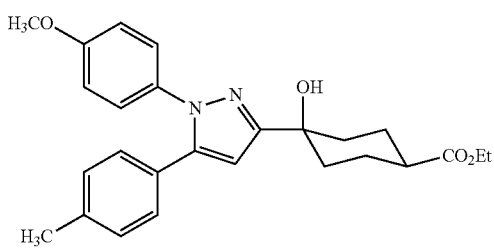

was synthesized by the following procedure.

Potassium carbonate (41.4 mg, 0.3 mmol) and ethyl iodide (24.8 µl, 0.3 mmol) were added to a solution of 4-hydroxy-4-(1-(4-methoxyphenyl)-5-(p-tolyl)-1H-pyrazol-3-yl)-cis-cyclohexanecarboxylic acid (Compound 16) (41.6 mg, 0.10 mmol) in DMF (1.0 ml), and the resulting mixture was stirred for 2 hours. Brine was added to the reaction solution, and the resulting solution was extracted with ethyl acetate. The organic layer was washed with brine, dried over anhydrous sodium sulfate, and concentrated under reduced pressure. The residue was purified by flash column chromatography (silica gel, n-hexane/ethyl acetate) to obtain Compound 58 (44.1 mg, 0.10 mmol, 97%) as a white amorphous product.

¹H-NMR (400 MHz, CDCl₃) δ: 1.27 (3H, t, J=6.8 Hz), 1.85-2.09 (8H, m), 2.33 (3H, s), 2.34-2.41 (1H, m), 2.59 (1H, s), 3.80 (3H, s), 4.15 (2H, q, J=6.8 Hz), 6.38 (1H, s), 6.84 (2H, d, J=8.8 Hz), 7.09-7.09 (4H, m), 7.20 (2H, d, J=8.8 Hz).

ESI-MS: m/z=435 (M+H)⁺

Prodrugs of the above-described Compound 3 were synthesized (Compounds 59 to 70).

Compound 59

As Compound 59, 4-hydroxy-4-(1-(4-methoxyphenyl)-5-(p-tolyl)-1H-pyrazol-3-yl)cis-cyclohexyl dimethylcarbamate:

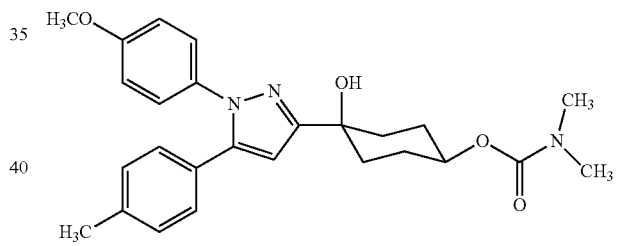

was synthesized by the following procedure.

A solution of 1-(1-(4-methoxyphenyl)-5-(p-tolyl)-1H-pyrazol-3-yl)cyclohexan-cis-1,4-diol (Compound 3) (230 mg, 0.60 mmol) in tetrahydrofuran (6.0 ml) was stirred for 10 minutes under ice-cooling. Sodium hydride (26.4 mg, 0.66 mmol) was added to the reaction solution, and the resulting mixture was stirred at the same temperature for 20 minutes. Dimethylcarbamoyl chloride (84 µL, 0.9 mmol) was added dropwise thereto, and the resulting mixture was stirred at room temperature for 3 hours. Thereafter, brine was added to the reaction solution, and the resulting solution was extracted with ethyl acetate. The organic layer was washed with brine, dried using anhydrous sodium sulfate, and concentrated under reduced pressure. The residue was purified by flash column chromatography (silica gel, n-hexane/ethyl acetate) to obtain Compound 59 (95.6 mg, 0.21 mmol, 35%) as a pale yellow amorphous product.

¹H-NMR (400 MHz, CDCl₃) δ: 1.93-2.04 (8H, m), 2.33 (3H, s), 2.71 (1H, s), 2.92 (6H, s), 3.80 (3H, s), 4.73-4.79 (1H, m), 6.37 (1H, s), 6.84 (2H, d, J=8.8 Hz), 7.09-7.09 (4H, m), 7.20 (2H, J=8.8 Hz).

ESI-MS: m/z=450 (M+H)⁺

Compound 60

As Compound 60, cyclohexyl 4-hydroxy-4-(1-(4-methoxyphenyl)-5-(p-tolyl)-1H-pyrazol-3-yl)-cis-cyclohexyl carbonate:

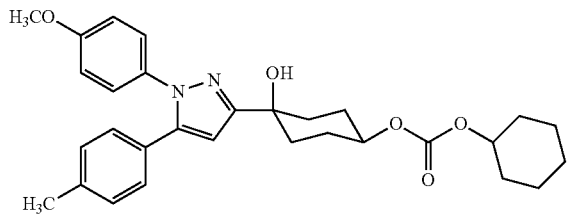

was synthesized by the following procedure.

A solution of 1-(1-(4-methoxyphenyl)-5-(p-tolyl)-1H-pyrazol-3-yl)cyclohexan-cis-1,4-diol (Compound 3) (250 mg, 0.66 mmol) in tetrahydrofuran (2.2 ml) was cooled in ice, and sodium hydride (63.4 mg, 1.45 mmol) was added thereto, followed by stirring the resulting mixture at the same temperature for 10 minutes. Cyclohexyl 1-iodoethyl carbonate (354 mg, 1.18 mmol) was then added to the mixture, and the resulting mixture was stirred at room temperature for 12 hours. Brine was added to the reaction solution, and the resulting solution was extracted with ethyl acetate. The organic layer was washed with brine, dried using anhydrous sodium sulfate, and concentrated under reduced pressure. The residue was purified by flash column chromatography (silica gel, n-hexane/ethyl acetate) to obtain Compound 60 (161 mg, 0.29 mmol, 44%) as a white amorphous product.

$^1$H-NMR (400 MHz, CDCl$_3$) δ: 1.23-1.28 (4H, m), 1.31-1.40 (2H, m), 1.44-1.56 (4H, m), 1.70-1.79 (4H, m), 1.93-2.08 (4H, m), 2.32 (3H, s), 2.82 (1H, s), 3.79 (3H, s), 4.57-4.64 (1H, m), 4.67-4.71 (1H, m), 6.38 (1H, s), 6.84 (2H, d, J=8.4 Hz), 7.08-7.08 (4H, m), 7.19 (2H, J=8.4 Hz).

ESI-MS: m/z=505 (M+H)$^+$

The following compounds were synthesized in the same manner as in the synthesis of the above-described Compound 59 and Compound 60.

Compound 63

As Compound 63, succinic acid mono-4-hydroxy-4-(1-(4-methoxyphenyl)-5-(ptolyl)-1H-pyrazol-3-yl)-cis-cyclohexyl ester:

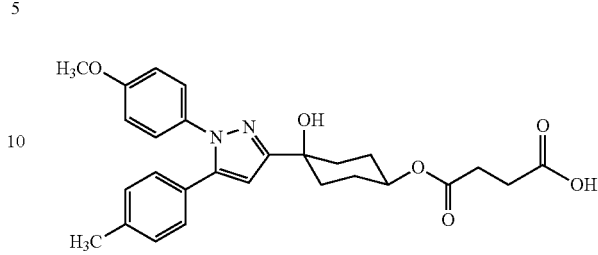

was synthesized by the following procedure.

Sodium hydride (63.4 mg, 1.45 mmol) was added to a solution of 1-(1-(4-methoxyphenyl)-5-(p-tolyl)-1H-pyrazol-3-yl)cyclohexan-cis-1,4-diol (Compound 3) (250 mg, 0.66 mmol) in DMF (3.3 ml), and the resulting mixture was stirred for 30 minutes. Succinic anhydride (99 mg, 0.99 mmol) was added thereto, and the resulting mixture was stirred for 12 hours. Thereafter, 1 M hydrochloric acid and ethyl acetate were added to the reaction solution, and the resulting solution was extracted with ethyl acetate. The organic layer was washed with brine, dried using anhydrous sodium sulfate, and concentrated under reduced pressure. The residue was purified by flash column chromatography (silica gel, n-hexane/ethyl acetate) to obtain Compound 63 (87.0 mg, 0.18 mmol, 28%) as a white amorphous product.

$^1$H-NMR (400 MHz, CDCl$_3$) δ: 1.86-1.88 (2H, m), 1.96-2.02 (4H, m), 2.08-2.11 (3H, m), 2.32 (3H, s), 2.58-2.64 (4H, m), 3.81 (3H, s), 4.82-4.88 (1H, m), 6.38 (1H, s), 6.84 (2H, d, J=8.0 Hz), 7.09-7.09 (4H, m), 7.18 (2H, J=8.0 Hz).

ESI-MS: m/z=479 (M+H)$^+$

TABLE 6

| Compound | Structural Formula | Compound Data |
|---|---|---|
| 61 | H$_3$CO-[pyrazole with OH-cyclohexyl-O-C(O)-OCH$_2$CH$_3$, H$_3$C-phenyl] | $^1$H-NMR (400 MHz, CDCl3) δ: 1.32 (3H, t, J = 8.0 Hz), 1.97-2.09 (8H, m), 2.33 (3H, s), 2.62 (1H, s), 3.80 (3H, s), 4.20 (2H, q, J = 8.0 Hz), 4.69-4.71 (1H, m), 6.37 (1H, s), 6.84 (2H, d, J = 8.8 Hz), 7.09-7.09 (4H, m), 7.20 (2H, J = 8.8 Hz). ESI-MS: m/z = 451 (M + H)$^+$ |
| 62 | H$_3$CO-[pyrazole with OH-cyclohexyl-O-C(O)-C(CH$_3$)$_3$, H$_3$C-phenyl] | $^1$H-NMR (400 MHz, CDCl$_3$) δ: 1.21 (9H, s), 1.92-2.06 (9H, m), 2.33 (3H, s), 3.80 (3H, s), 4.80-4.86 (1H, m), 6.38 (1H, s), 6.84 (2H, d, J = 8.4 Hz), 7.09-7.09 (4H, m), 7.20 (2H, J = 8.4 Hz), ESI-MS: m/z = 463 (M + H)$^+$ |

Compound 64

As Compound 64, cyclohexyl (4-hydroxy-4-(1-(4-methoxyphenyl)-5-(p-tolyl)-1H-pyrazol-3-yl)-cis-cyclohexyloxy)ethyl carbonate:

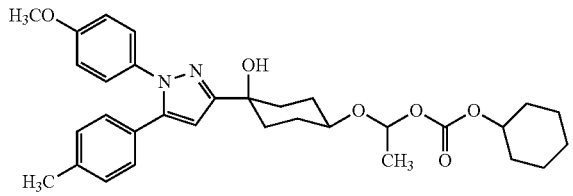

was synthesized by the following procedure.

Cyclohexyl 1-iodoethyl carbonate (567 mg, 1.90 mmol), diisopropylethylamine (460 μl, 2.64 mmol) and silver chloride (273 mg, 1.90 mmol) were added to a solution of 1-(1-(4-methoxyphenyl)-5-(p-tolyl)-1H-pyrazol-3-yl)cyclohexan-cis-1,4-diol (Compound 3) (400 mg, 1.05 mmol) in dichloroethane (5.4 ml), and the resulting mixture was stirred at 80° C. for 12 hours. The mixture was allowed to cool to room temperature, and the reaction solution was filtered through Celite. To the filtrate, 1 M hydrochloric acid and ethyl acetate were added, and thereafter the resulting solution was extracted with ethyl acetate. The organic layer was washed with brine, dried using anhydrous sodium sulfate, and concentrated under reduced pressure. The residue was purified by flash column chromatography (silica gel, n-hexane/ethyl acetate) to obtain Compound 64 (31.9 mg, 0.058 mmol, 5.1%) as a white amorphous product.

$^1$H-NMR (400 MHz, CDCl$_3$) δ: 1.15-1.34 (9H, m), 1.48-1.65 (4H, m), 1.83-1.98 (8H, m), 2.33 (3H, s), 2.49 (1H, s), 3.52-3.58 (1H, m), 3.64-3.71 (1H, m), 3.81 (3H, s), 4.92 (1H, q, J=5.2 Hz), 6.39 (1H, s), 6.84 (2H, d, J=8.8 Hz), 7.09-7.09 (4H, m), 7.19 (2H, J=8.8 Hz).

ESI-MS: m/z=549 (M+H)$^+$

The following compounds were synthesized in the same manner as in the synthesis of the above-described Compound 59 and Compound 60.

Compound 67

As Compound 67, 4-hydroxy-4-(1-(4-methoxyphenyl)-5-(p-tolyl)-1H-pyrazol-3-yl)cis-cyclohexyl 2-aminoacetate:

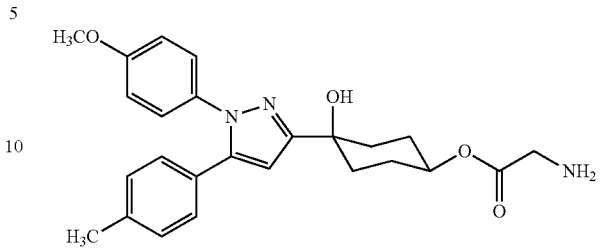

was synthesized by the following procedure.

To a solution of 4-hydroxy-4-(1-(4-methoxyphenyl)-5-(p-tolyl)-1H-pyrazol-3-yl)-cis-cyclohexyl 2-benzyloxycarbonylaminoacetate (Intermediate 57) (33.2 mg, 0.058 mmol) in methanol (2.00 mL), 10% palladium/carbon (6.16 mg, 50 wt %) was added at room temperature, and the resulting mixture was stirred under hydrogen atmosphere for 14 hours. The reaction solution was filtered through Celite, and the filtrate was concentrated under reduced pressure. The residue was purified by flash chromatography (NH silica gel, chloroform/methanol) to obtain Compound 67 (18.4 mg, 0.042 mmol, 73%) as a colorless amorphous product.

$^1$H-NMR (400 MHz, CDCl$_3$) δ: 1.58-1.82 (2H, m), 1.88-2.12 (9H, m), 2.33 (3H, s), 3.43 (2H, s), 3.81 (3H, s), 4.88-4.94 (1H, m), 6.37 (1H, s), 6.83-6.87 (2H, m), 7.09-7.11 (4H, m), 7.18-7.22 (2H, m).

ESI-MS: m/z=436 (M+H)$^+$

The following compound was synthesized in the same manner as in the synthesis of Compound 67 as described above.

TABLE 7

| Compound | Structural Formula | Compound Data |
|---|---|---|
| 65 | | $^1$H-NMR (400 MHz, CDCl$_3$) δ: 1.26 (3H, t, J = 5.0 Hz), 1.33 (3H, d, J = 4.8 Hz), 1.86-2.01 (8H, m), 2.33 (3H, s), 2.49 (1H, s), 3.49-3.53 (1H, m), 3.65-3.70 (2H, m), 3.80 (3H, s), 4.84 (1H, q, J = 4.8 Hz), 6.39 (1H, s), 6.84 (2H, d, J = 8.0 Hz), 7.09-7.09 (4H, m), 7.19 (2H, J = 8.0 Hz). ESI-MS: m/z = 495 (M + H)$^+$ |
| 66 | | $^1$H-NMR (400 MHz, CDCl$_3$) δ: 1.23 (9H, s), 1.89-2.00 (6H, m), 2.05-2.08 (2H, m), 2.33 (3H, s), 2.48 (1H, s), 3.67-3.71 (1H, m), 3.81 (3H, s), 5.39 (2H, s), 6.38 (1H, s), 6.84 (2H, d, J = 9.2 Hz), 7.09-7.09 (4H, m), 7.19 (2H, J = 9.2 Hz). ESI-MS: m/z = 493 (M + H)$^+$ |

TABLE 8

| Compound | Structural Formula | Compound Data |
|---|---|---|
| 68 | 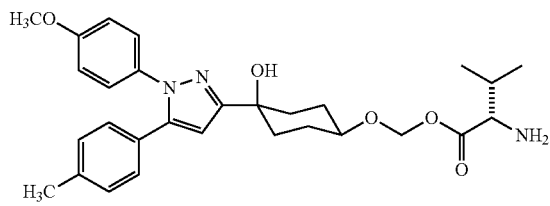 | ¹H-NMR (400 MHz, CDCl₃) δ: 0.93 (3H, d, J = 6.4 Hz), 1.00 (3H, d, J = 6.4 Hz), 1.90-2.10 (9H, m), 2.34 (3H, s), 3.31 (1H, d, J = 8.0 Hz), 3.81 (3H, s), 4.88-4.94 (1H, s), 6.36, (1H, s), 6.83-6.87 (2H, m), 7.09-7.11 (4H, m), 7.18-7.22 (2H, m).<br>ESI-MS: m/z = 460 (M − OH)⁺ |

Compound 69

As Compound 69, (S)-4-hydroxy-4-(1-(4-methoxyphenyl)-5-(p-tolyl)-1H-pyrazol-3-yl)-cis-cyclohexyl 2-amino-3-methylbutanoate:

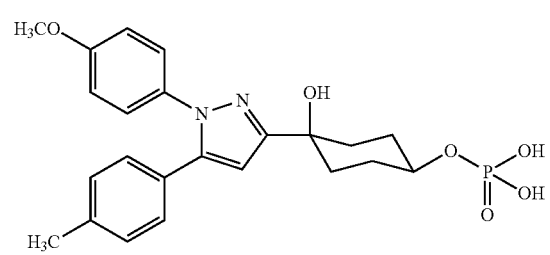

was synthesized by the following procedure.

To a mixed solution of (S)-4-hydroxy-4-(1-(4-methoxyphenyl)-5-(p-tolyl)-1H-pyrazol-3-yl)cyclohexyloxy)methyl 2-(benzyloxycarbonylamino)-3-methylbutanoate (Intermediate 59) (122 mg, 0.190 mmol) in dioxane/ethanol (2.00 mL/2.00 mL), 2,2'-bipyridyl (15.0 mg, 0.096 mmol) and 10% palladium/carbon (49.0 mg, 40 wt %) were added at room temperature, and the resulting mixture was stirred under hydrogen atmosphere for 14 hours. The reaction solution was filtered through Celite, and the filtrate was concentrated under reduced pressure. The residue was purified by flash chromatography (silica gel, chloroform/methanol) to obtain Compound 69 (38.6 mg, 0.076 mmol, 40%) as a colorless amorphous product.

¹H-NMR (400 MHz, CDCl₃) δ: 0.92 (3H, d, J=6.8 Hz), 1.02 (3H, d, J=6.8 Hz), 1.90-2.12 (9H, m), 2.34 (3H, s), 3.32-3.34 (1H, m), 167-3.76 (1H, m), 3.81 (3H, s), 5.41 (1H, d, J=6.4 Hz), 5.47 (1H, d, J=6.4 Hz), 6.38, (1H, s), 6.83-6.87 (2H, m), 7.09-7.12 (4H, m), 7.18-7.22 (2H, m).

ESI-MS: m/z=490 (M−OH)⁺

Compound 70

As Compound 70, 4-hydroxy-4-(1-(4-methoxyphenyl)-5-(p-tolyl)-1H-pyrazol-3-yl)cis-cyclohexyl dihydrogen phosphate:

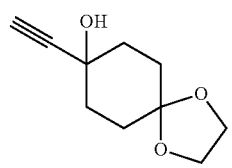

was synthesized by the following procedure.

To a mixed solution of dibenzyl 4-hydroxy-4-(1-(4-methoxyphenyl)-5-(p-tolyl)-1H-pyrazol-3-yl)-cis-cyclohexyl phosphate (Intermediate 60) (251 mg, 0.393 mmol), methanol (2.6 mL) and ethyl acetate (2.6 mL), 10% palladium/carbon (41.8 mg, 50 wt %) was added, and the resulting mixture was stirred under hydrogen atmosphere at room temperature for 2.5 hours. The reaction solution was filtered through Celite, and the filtrate was concentrated under reduced pressure. The residue was recrystallized from dichloromethane/diethyl ether to obtain Compound 70 (97.2 mg, 0.212 mmol, 54%) as a white solid.

¹H-NMR (400 MHz, DMSO-d₆) δ: 1.68-1.98 (8H, m), 2.28 (3H, s), 3.76 (3H, s), 4.13 (1H, br), 4.92 (1H, br), 6.53 (1H, s), 6.91-6.95 (2H, m), 7.08-7.17 (6H, m).

ESI-MS: m/z=459 (M+H)⁺

Intermediate 1

As Intermediate 1,8-ethinyl-1,4-dioxaspiro[4.5]decan-8-ol:

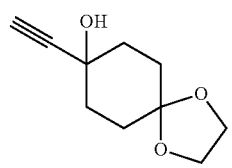

was synthesized by the following procedure.

To a solution of trimethylsilylacetylene (27.1 mL, 0.192 mol) in tetrahydrofuran (300 mL), 2.77 M n-butyllithium (a solution in n-hexane, 69.3 mL, 0.192 mol) was added dropwise at −76° C. for 30 minutes, and the resulting mixture was stirred at the same temperature for 30 minutes. Thereafter, a solution of 1,4-dioxaspiro[4.5]decan-8-one (25.0 g, 0.160 mol) in tetrahydrofuran (100 mL) was added dropwise thereto at −74° C. for 30 minutes, and the resulting mixture was stirred at the same temperature for 1 hour and 30 minutes. The reaction solution was poured into a saturated aqueous ammonium chloride solution, and the resulting solution was extracted with ethyl acetate. The organic layer was washed with brine, dried over anhydrous sodium sulfate, and concentrated under reduced pressure.

Methanol (320 mL) was added to the residue to dissolve it, and potassium carbonate (55.3 g, 0.400 mol) was added thereto. The resulting mixture was stirred at room temperature for 2 hours, and the reaction solution was concentrated under reduced pressure. Distilled water was added to the residue, and the resulting solution was extracted with ethyl acetate. The organic layer was washed with distilled water and brine. The organic layer was dried over anhydrous sodium sulfate, and concentrated under reduced pressure. The residue was purified by flash chromatography (silica gel, n-hexane/ethyl acetate) to obtain Intermediate 1 (29.1 g, 0.160 mol, 100%) as a white solid.

$^1$H-NMR (400 MHz, CDCl$_3$) δ: 1.75-2.03 (9H, m), 2.49 (1H, m), 3.95 (4H, s).

ESI-MS: m/z=165 (M−OH)$^+$

Intermediate 2

As Intermediate 2,1-(3-hydroxy-3-(p-tolyl)propyn-1-yl)cyclohexanol:

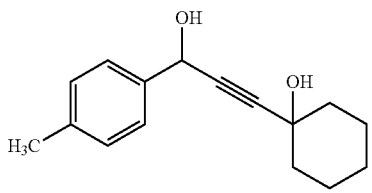

was synthesized by the following procedure.

To a solution of 1-ethynylcyclohexanol (500 mg, 4.02 mmol) in tetrahydrofuran (20 mL), 2.77 M n-butyllithium (a solution in n-hexane, 3.6 mL, 9.90 mmol) was added dropwise at −78° C., and the resulting mixture was stirred at the same temperature for 1 hour. To the reaction solution, p-tolualdehyde (0.52 mL, 4.40 mmol) was added at −78° C., and the obtained solution was allowed to warm gradually to room temperature with stirring. Distilled water and 1 M hydrochloric acid were added to the reaction solution to acidify it, and thereafter the resulting solution was extracted with ethyl acetate. The organic layer was dried over anhydrous magnesium sulfate, and concentrated under reduced pressure. The residue was purified by flash chromatography (silica gel, n-hexane/ethyl acetate) to obtain Intermediate 2 (598 mg, 2.44 mmol, 61%) as a pale yellow solid.

$^1$H-NMR (400 MHz, CDCl$_3$) δ: 1.18-1.30 (1H, m), 1.47-1.74 (7H, m), 1.89-1.98 (2H, m), 2.08 (1H, brs), 2.22 (1H, brs), 2.36 (3H, s), 5.47 (1H, s), 7.19 (2H, d, J=8.0 Hz), 7.43 (2H, d, J=8.0 Hz).

ESI-MS: m/z=227 (M−OH)$^+$

Intermediate 3

As Intermediate 3,8-(3-hydroxy-3-(p-tolyl)propyn-1-yl)-1,4-dioxaspiro[4.5]decan-8-ol

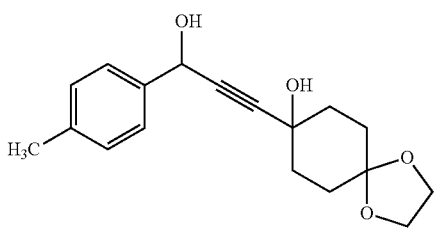

was synthesized by the following procedure.

To a solution of 8-ethinyl-1,4-dioxaspiro[4.5]decan-8-ol (Intermediate 1) (15.0 g, 82.3 mmol) in tetrahydrofuran (165 mL), 2.77 M n-butyllithium (a solution in n-hexane, 62.4 mL, 172.9 mmol) was added dropwise at −72° C. for 25 minutes, and the resulting mixture was stirred at the same temperature for 30 minutes. Then, p-tolualdehyde (10.2 mL, 86.4 mmol) was added dropwise thereto at −72° C. for 5 minutes, and the resulting mixture was stirred at the same temperature for 30 minutes. The reaction solution was allowed to warm to room temperature, and thereafter poured into a saturated aqueous ammonium chloride solution. The reaction solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain Intermediate 3 (17.7 g, 58.5 mmol, 71%) as an amorphous product.

$^1$H-NMR (400 MHz, CDCl$_3$) δ: 1.72-1.85 (4H, m), 1.90-2.04 (4H, m), 2.35 (3H, s), 2.55 (1H, s), 2.78 (1H, d, J=6.0 Hz), 3.93 (4H, s), 5.44 (1H, d, J=6.0 Hz), 7.17 (2H, d, J=8.0 Hz), 7.40 (2H, d, J=8.0 Hz).

ESI-MS: m/z=285 (M−OH)$^+$

Intermediate 4

As Intermediate 4, 8-(3-hydroxy-3-(4-methoxyphenyl)propyn-1-yl)-1,4-dioxaspiro[4.5]decan-8-ol:

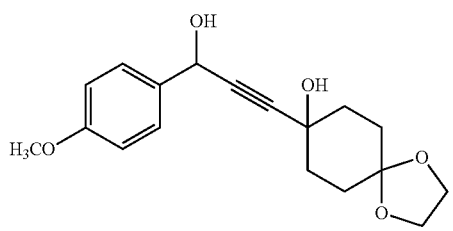

was synthesized by the following procedure.

To a solution of 8-ethinyl-1,4-dioxaspiro[4.5]decan-8-ol (Intermediate 1) (5.02 g, 27.6 mmol) in tetrahydrofuran (100 mL), 2.63 M n-butyllithium (a solution in n-hexane, 22.0 mL, 57.9 mmol) was added dropwise at −72° C. for 15 minutes, and the resulting mixture was stirred at the same temperature for 60 minutes. Then, 4-methoxyaldehyde (3.52 mL, 28.9 mmol) was added dropwise thereto at −72° C. for 10 minutes, and the resulting mixture was stirred at the same temperature for 60 minutes. The reaction solution was allowed to warm to room temperature, and thereafter poured into a saturated aqueous ammonium chloride solution. The reaction solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain Intermediate 4 (7.46 g, 23.4 mmol, 85%) as an amorphous product.

$^1$H-NMR (400 MHz, CDCl$_3$) δ: 1.73-1.85 (4H, m), 1.91-2.04 (4H, m), 2.32 (1H, s), 2.52 (1H, d, J=6.1 Hz), 3.81 (3H, s), 3.94 (4H, s), 5.44 (1H, d, J=6.1 Hz), 6.89 (2H, d, J=8.5 Hz), 7.44 (2H, d, J=8.5 Hz).

Intermediate 5

As Intermediate 5, 8-(3-(4-chlorophenyl)-3-hydroxypropyn-1-yl)-1,4-dioxaspiro[4.5]decan-8-ol

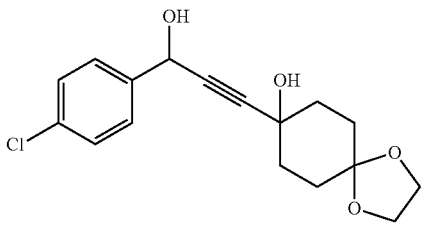

was synthesized by the following procedure.

To a solution of 8-ethinyl-1,4-dioxaspiro[4.5]decan-8-ol (Intermediate 1) (5.03 g, 27.6 mmol) in tetrahydrofuran (100 mL), 2.63 M n-butyllithium (a solution in n-hexane, 22.1 mL, 57.9 mmol) was added dropwise at −72° C. for 15 minutes, and the resulting mixture was stirred at the same temperature for 60 minutes. Then, 4-chlorobenzaldehyde (4.06 g, 28.9 mmol) was added dropwise thereto at −72° C. for 10 minutes, and the resulting mixture was stirred at the same temperature for 60 minutes. The reaction solution was allowed to warm to room temperature, and thereafter poured into a saturated aqueous ammonium chloride solution. The reaction solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain Intermediate 5 (8.13 g, 25.2 mmol, 91%) as an amorphous product.

$^1$H-NMR (400 MHz, CDCl$_3$) δ: 1.68-1.81 (4H, m), 1.86-1.90 (4H, m), 3.55 (1H, s), 3.90 (4H, s), 4.03 (1H, d, J=4.2 Hz), 5.41 (1H, d, J=4.2 Hz), 7.28 (2H, d, J=8.3 Hz), 7.41 (2H, d, J=8.3 Hz).

The following compounds were synthesized in the same manner as in the above-described Intermediates 1 to 5.

Intermediate 9

As Intermediate 9, 3-(8-hydroxy-1,4-dioxaspiro[4.5]decan-8-yl)-1-(p-tolyl)-2-propyn-1-one:

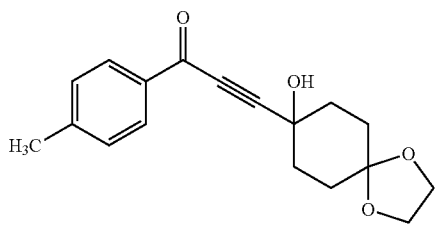

was synthesized by the following procedure.

Manganese dioxide (29.6 g, 289 mmol) was added to a solution of 8-(3-hydroxy-3-(ptolyl)propyn-1-yl)-1,4-dioxaspiro[4.5]decan-8-ol (Intermediate 3) (17.5 g, 57.9 mmol) in dichloromethane (289 mL), and the resulting mixture was stirred at room temperature for 15 hours. The reaction solu-

TABLE 9

| Intermediate Examples | Structural Formula | Compound Data |
|---|---|---|
| 6 | | $^1$H-NMR (400 MHz, CDCl$_3$) δ: 1.71-1.84 (4H, m), 1.88-2.03 (4H, m), 165-331 (2H, m), 3.91 (4H, s), 5.47 (1H, d, J = 5.2 Hz), 7.29-7.38 (3H, m), 7.51 (2H, d, J = 8.4 Hz). ESI-MS: m/z = 271 (M − OH)$^+$ |
| 7 | | $^1$H-NMR (400 MHz, CDCl$_3$) δ: 1.63 (1H, s), 1.75-1.83 (4H, m), 1.95-2.05 (4H, m), 2.62 (1H, s), 3.94 (4H, s), 5.56 (1H, s), 7.64 (4H, s). ESI-MS: m/z = 339 (M − OH)$^+$ |

Intermediate 8

As Intermediate 8, 3-(1-hydroxycyclohexyl)-1-(p-tolyl)-2-propyn-1-one:

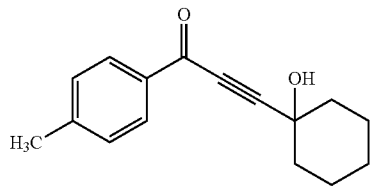

was synthesized by the following procedure.

Manganese dioxide (1.15 g, 13.2 mmol) was added to a solution of 1-(3-hydroxy-3-(p-tolyl)propyn-1-yl)cyclohexanol (Intermediate 2) (593 mg, 2.42 mmol) in dichloromethane (20 mL), and the resulting mixture was stirred at room temperature for 5 hours. The reaction solution was filtered through Celite, and the filtrate was concentrated under reduced pressure. The residue was purified by flash chromatography (silica gel, n-hexane/ethyl acetate) to obtain Intermediate 8 (534 mg, 2.20 mmol, 91%) as a pale yellow oily product.

$^1$H-NMR (400 MHz, CDCl$_3$) δ: 1.28-1.39 (1H, m), 1.55-1.84 (7H, m), 2.02-2.11 (2H, m), 2.23 (1H, brs), 2.43 (3H, s), 7.28 (2H, d, J=8.0 Hz), 8.02 (2H, d, J=8.0 Hz).

tion was filtered through Celite, and the filtrate was concentrated under reduced pressure. The residue was purified by flash chromatography (silica gel, n-hexane/ethyl acetate) to obtain Intermediate 9 (14.3 g, 47.6 mmol, 82%) as an oily product.

$^1$H-NMR (400 MHz, CDCl$_3$) δ: 1.79-1.85 (2H, m), 1.87-1.93 (2H, m), 2.04-2.15 (4H, m), 2.20 (1H, s), 2.43 (3H, s), 3.97 (4H, s), 7.28 (2H, d, J=8.0 Hz), 8.00 (2H, d, J=8.0 Hz).

ESI-MS: m/z=284 (M−OH)$^+$

Intermediate 10

As Intermediate 10, 3-(8-hydroxy-1,4-dioxaspiro[4.5]decan-8-yl)-1-(6-methylpyridin-3-yl)-2-propyn-1-one:

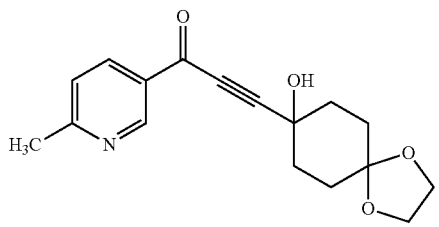

was synthesized by the following procedure.

To a solution of 8-ethinyl-1,4-dioxaspiro[4.5]decan-8-ol (Intermediate 1) (592 mg, 3.25 mmol) in tetrahydrofuran (6 mL), 2.63 M n-butyllithium (a solution in n-hexane, 2.6 mL, 6.82 mmol) was added dropwise at −78° C. for 5 minutes, and the resulting mixture was stirred at the same temperature for 30 minutes. Then, a solution of N-methoxy-N-methyl-6-methylnicotinamide (614.5 mg, 3.41 mmol) in tetrahydrofuran (5 ml) was added dropwise thereto at −78° C. for 20 minutes, and the resulting mixture was stirred at the same temperature for 30 minutes. The reaction solution was allowed to warm to room temperature, and thereafter poured into a saturated aqueous ammonium chloride solution. The reaction solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain Intermediate 10 (626.3 mg, 2.08 mmol, 65%) as a pale yellow solid.

$^1$H-NMR (400 MHz, CDCl$_3$) δ: 1.76-1.83 (2H, m), 1.87-1.94 (2H, m), 2.04-2.10 (2H, m), 2.12-2.19 (2H, m), 2.30 (1H, s), 2.66 (3H, s), 3.97 (4H, s), 7.29 (1H, d, J=8.0 Hz), 8.22 (1H, dd, J=2.4, 8.0 Hz), 9.21 (1H, d, J=2.4 Hz).

ESI-MS: m/z=284 (M−OH)$^+$

Intermediate 11

As Intermediate 11, 3-(8-hydroxy-1,4-dioxaspiro[4.5]decan-8-yl)-1-(4-methoxyphenyl)-2-propyn-1-one:

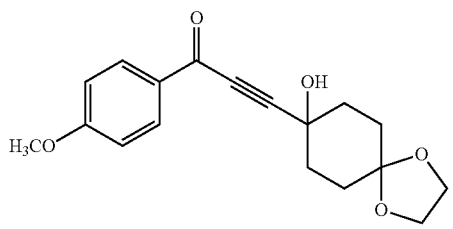

was synthesized by the following procedure.

Manganese dioxide (9.69 g, 112 mmol) was added to a solution of 8-(3-hydroxy-3-(4-methoxyphenyl)propyn-1-yl)-1,4-dioxaspiro[4.5]decan-8-ol (Intermediate 4) (7.10 g, 22.3 mmol) in dichloromethane (100 mL), and the resulting mixture was stirred at room temperature for 18 hours. The reaction solution was filtered through Celite, and the filtrate was concentrated under reduced pressure. The residue was purified by flash chromatography (silica gel, n-hexane/ethyl acetate) to obtain Intermediate 11 (5.45 g, 17.2 mmol, 77%) as an oily product.

$^1$H-NMR (400 MHz, CDCl$_3$) δ: 1.78-1.93 (4H, m), 2.03-2.17 (4H, m), 2.27 (1H, s), 3.89 (3H, s), 3.97 (4H, s), 6.95 (2H, d, J=9.0 Hz), 8.08 (2H, d, J=9.0 Hz).

ESI-MS: m/z=299 (M−OH)$^+$

Intermediate 12

As Intermediate 12, 1-(4-chlorophenyl)-3-(8-hydroxy-1,4-dioxaspiro[4.5]decan-8-yl)-2-propyn-1-one:

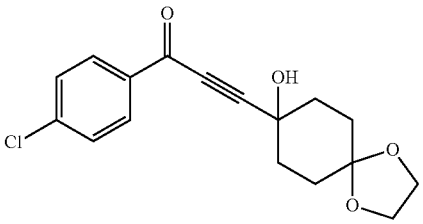

was synthesized by the following procedure.

Manganese dioxide (10.4 g, 119 mmol) was added to a solution of 8-(3-(4-chlorophenyl)-3-hydroxypropyn-1-yl)-1,4-dioxaspiro[4.5]decan-8-ol (Intermediate 5) (7.70 g, 23.9 mmol) in dichloromethane (120 mL), and the resulting mixture was stirred at room temperature for 18 hours. The reaction solution was filtered through Celite, and the filtrate was concentrated under reduced pressure. The residue was purified by flash chromatography (silica gel, n-hexane/ethyl acetate) to obtain Intermediate 12 (5.45 g, 17.0 mmol, 71%) as an oily product.

$^1$H-NMR (400 MHz, CDCl$_3$) δ: 1.77-1.94 (4H, m), 2.04-2.19 (4H, m), 2.15 (1H, s), 3.98 (4H, s), 7.47 (2H, d, J=8.5 Hz), 8.04 (2H, d, J=8.5 Hz).

ESI-MS: m/z=303 (M−OH)$^+$

The following compounds were synthesized in the same manner as in the above-described Intermediates 8 to 12.

TABLE 10

| Intermediate Examples | Structural Formula | Compound Data |
|---|---|---|
| 13 | | $^1$H-NMR (400 MHz, CDCl$_3$) δ: 1.78-1.94 (4H, m), 2.04-2.20 (4H, m), 2.33 (1H, s), 3.97 (4H, s), 7.49 (2H, t, J = 7.2 Hz), 7.62 (1H, t, J = 7.2 Hz), 7.69 (2H, d, J = 7.2 Hz). ESI-MS: m/z = 269 (M − OH)$^+$ |
| 14 | | $^1$H-NMR (400 MHz, CDCl3) δ: 1.81-1.84 (2H, m), 1.89-1.94 (2H, m), 2.09-2.17 (4H, m), 2.38 (1H, s), 3.98 (4H, s), 7.76 (2H, d, J = 8.0 Hz), 821 (2H, d, J = 8.0 Hz). |

TABLE 10-continued

| Intermediate Examples | Structural Formula | Compound Data |
|---|---|---|
| 15 | | $^1$H-NMR (400 MHz, CDCl3) δ: 1.76-1.95 (4H, m), 2.04-2.20 (5H, m), 2.36 (3H, d, J = 2.0 Hz), 3.97 (4H, s), 7.31 (1H, t, J = 8.0 Hz), 7.71 (1H, d, J = 10.0 Hz), 7.81 (1H, d, J = 8.0 Hz). ESI-MS: m/z = 319 (M + H)$^+$ |
| 16 | | $^1$H-NMR (400 MHz, CDCl3) δ: 1.75-1.96 (4H, m), 2.03-2.25 (4H, m), 2.47-2.60 (1H, m), 3.98 (4H, s), 7.77-7.82 (2H, m), 8.16-8.23 (2H, m). ESI-MS: m/z = 312 (M + H)$^+$ |
| 17 | | $^1$H-NMR (400 MHz, CDCl3) δ: 1.26 (3H, t, J = 7.6 Hz), 1.78-1.94 (4H, m), 2.03-2.19 (4H, m), 2.27 (1H, br), 2.72 (2H, q, J = 7.6 Hz), 3.98 (4H, s), 7.30 (2H, d, J = 8.4 Hz), 8.03 (2H, d, J = 8.4 Hz). ESI-MS: m/z = 315 (M + H)$^+$ |

Intermediate 18

As Intermediate 18, 8-(1-(4-methoxyphenyl)-5-(p-tolyl)-1H-pyrazol-3-yl)-1,4-dioxaspiro[4.5]decan-8-ol:

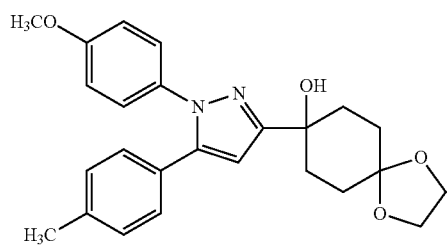

was synthesized by the following procedure.

Triethylamine (5.87 mL, 42.1 mmol) was added dropwise to a solution of 4-methoxyphenylhydrazine hydrochloric acid salt (7.35 g, 42.1 mmol) in ethanol (76.6 mL), and the resulting mixture was stirred at room temperature for 30 minutes. To the reaction solution, a solution of 3-(8-hydroxy-1,4-dioxaspiro[4.5]decan-8-yl)-1-(p-tolyl)-2-propyn-1-one (Intermediate 9) (11.5 g, 38.3 mmol) in ethanol (76.6 mL) was added dropwise, and the resulting mixture was stirred at room temperature for 15 hours. Thereafter, the reaction solution was concentrated under reduced pressure. Water was added to the residue, and the resulting solution was extracted with ethyl acetate. The organic layer was washed with 1 M hydrochloric acid, distilled water and brine, and then dried over anhydrous magnesium sulfate, and concentrated under reduced pressure. The residue was purified by flash chromatography (silica gel, n-hexane/ethyl acetate) to obtain Intermediate 18 (14.7 g, 35.0 mmol, 91%) as an amorphous product.

$^1$H-NMR (400 MHz, CDCl$_3$) δ: 1.71-1.74 (2H, m), 1.99-2.25 (6H, m), 2.33 (3H, s), 2.71 (1H, s), 3.81 (3H, s), 3.96-4.01 (4H, m), 6.39 (1H, s), 6.84 (2H, d, J=8.0 Hz), 7.09 (4H, s), 7.21 (2H, d, J=8.0 Hz).

ESI-MS: m/z=421 (M+H)$^+$

Intermediate 19

As Intermediate 19, 8-(1-(4-methoxyphenyl)-5-(6-methylpyridin-3-yl)-1H-pyrazol-3-yl)-1,4-dioxaspiro[4.5]decan-8-ol:

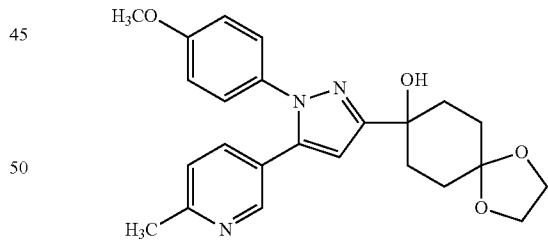

was synthesized by the following procedure.

Triethylamine (286 μL, 2.06 mmol) was added dropwise to a solution of 4-methoxyphenylhydrazine hydrochloric acid salt (359 mg, 2.06 mmol) in ethanol (4 mL), and the resulting mixture was stirred at room temperature for 30 minutes. To the reaction solution, a solution of 3-(8-hydroxy-1,4-dioxaspiro[4.5]decan-8-yl)-1-(6-methylpyridin-3-yl)-2-propyn-1-one (Intermediate 10) (563.7 mg, 1.87 mmol) in ethanol (5.4 mL) was added dropwise, and the resulting mixture was stirred at room temperature for 22 hours. Thereafter, the reaction solution was concentrated under reduced pressure. Water was added to the residue, and the resulting solution was extracted with ethyl acetate. The organic layer was washed with distilled water and brine, and then dried over anhydrous magnesium sulfate, and concentrated under reduced pressure. The residue was purified by flash chromatography (silica gel, n-hexane/ethyl acetate) to obtain Intermediate 19 (177 mg, 0.42 mmol, 22%) as an amorphous product.

¹H-NMR (400 MHz, CDCl₃) δ: 1.72-1.75 (2H, m), 2.00-2.03 (2H, m), 2.07-2.14 (2H, m), 2.19-2.26 (2H, m), 2.55 (3H, s), 2.65 (1H, s), 3.81 (3H, s), 3.96-4.03 (4H, m), 6.47 (1H, s), 6.86 (2H, d, J=8.8 Hz), 7.06 (1H, d, J=8.0 Hz), 7.20 (2H, d, J=8.8 Hz), 7.33 (1H, dd, J=2.2, 8.0 Hz), 8.40 (1H, d, J=2.2 Hz).

ESI-MS: m/z=422 (M+H)⁺

Intermediate 20

As Intermediate 20, 8-(1,5-bis(4-methoxyphenyl)-1H-pyrazol-3-yl)-1,4-dioxaspiro[4.5]decan-8-ol:

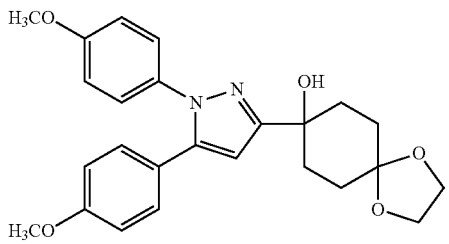

was synthesized by the following procedure.

A solution of 4-methoxyphenylhydrazine hydrochloric acid salt (470 mg, 2.69 mmol) and triethylamine (0.74 mL, 5.41 mmol) in ethanol (4.5 mL) was added to a solution of 3-(8-hydroxy-1,4-dioxaspiro[4.5]decan-8-yl)-1-(4-methoxyphenyl)-2-propyn-1-one (Intermediate 11) (700 mg, 2.24 mmol) in ethanol (4.5 mL), and the resulting mixture was stirred at room temperature for 20 hours. The reaction solution was concentrated under reduced pressure, and distilled water was added to the residue, followed by extraction of the resulting mixture with ethyl acetate. The organic layer was dried over anhydrous magnesium sulfate, and concentrated under reduced pressure. The residue was purified by flash chromatography (silica gel, n-hexane/ethyl acetate) to obtain Intermediate 20 (864 mg, 1.98 mmol, 88%) as a white amorphous product.

¹H-NMR (400 MHz, CDCl₃) δ: 1.68-1.77 (2H, m), 1.96-2.26 (6H, m), 2.70 (1H, brs), 180 (3H, s), 3.81 (3H, s), 3.94-4.04 (4H, m), 6.37 (1H, s), 6.81 (2H, d, J=8.8 Hz), 6.85 (2H, d, J=8.8 Hz), 7.13 (2H, d, J=8.8 Hz), 7.21 (2H, d, J=8.8 Hz).

ESI-MS: m/z=437 (M+H)⁺

Intermediate 21

As Intermediate 21, 8-(5-(4-chlorophenyl)-1-(4-methoxyphenyl)-1H-pyrazol-3-yl)-1,4-dioxaspiro[4.5]decan-8-ol:

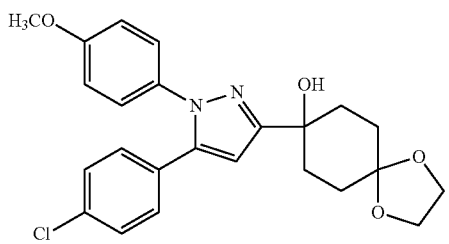

was synthesized by the following procedure.

Triethylamine (0.730 mL, 5.24 mmol) was added dropwise to a solution of 4-methoxyphenylhydrazine hydrochloric acid salt (457 mg, 2.62 mmol) in ethanol (4.4 mL), and the resulting mixture was stirred at room temperature for 30 minutes. To the reaction solution, a solution of 1-(4-chlorophenyl)-3-(8-hydroxy-1,4-dioxaspiro[4.5]decan-8-yl)-2-propyn-1-one (Intermediate 12) (700 mg, 2.18 mmol) in ethanol (4.4 mL) was added dropwise, and the resulting mixture was stirred at room temperature for 14 hours. Thereafter, the reaction solution was concentrated under reduced pressure. Water was added to the residue, and the resulting solution was extracted with ethyl acetate. The organic layer was washed with 1 M hydrochloric acid, distilled water and brine, and then dried over anhydrous magnesium sulfate, and concentrated under reduced pressure. The residue was purified by flash chromatography (silica gel, n-hexane/ethyl acetate) to obtain Intermediate 21 (756 mg, 1.71 mmol, 79%) as an amorphous product.

¹H-NMR (400 MHz, CDCl₃) δ: 1.69-1.76 (2H, m), 1.97-2.25 (6H, m), 2.66 (1H, brs), 3.82 (3H, s), 3.94-4.03 (4H, m), 6.43 (1H, s), 6.85-6.87 (2H, m), 7.13 (2H, d, J=8.4 Hz), 7.19 (2H, d, J=8.4 Hz), 7.25-7.27 (2H, m).

ESI-MS: m/z=441 (M+H)⁺

Intermediate 22

As Intermediate 22, 8-(1-(4-chlorophenyl)-5-(p-tolyl)-1H-pyrazol-3-yl)-1,4-dioxaspiro[4.5]decan-8-ol:

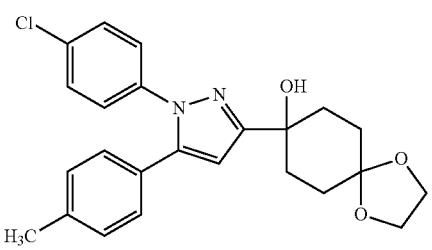

was synthesized by the following procedure.

Triethylamine (5.87 mL, 42.1 mmol) was added dropwise to a solution of 4-chlorophenylhydrazine hydrochloric acid salt (418 mg, 2.33 mmol) in ethanol (4.8 mL), and the resulting mixture was stirred at room temperature for 30 minutes. To the reaction solution, a solution of 3-(8-hydroxy-1,4-dioxaspiro[4.5]decan-8-yl)-1-(p-tolyl)-2-propyn-1-one (Intermediate 9) (698 mg, 2.32 mmol) in ethanol (4.7 mL) was added dropwise, and the resulting mixture was stirred at room temperature for 14 hours. Thereafter, the reaction solution was concentrated under reduced pressure. Water was added to the residue, and the resulting solution was extracted with ethyl acetate. The organic layer was washed with distilled water and brine, and then dried over anhydrous sodium sulfate, and concentrated under reduced pressure. The residue was purified by flash chromatography (silica gel, n-hexane/ethyl acetate) to obtain Intermediate 22 (948 mg, 2.23 mmol, yield: 96%) as an amorphous product.

¹H-NMR (400 MHz, CDCl₃) δ: 1.71-1.75 (2H, m), 1.98-2.14 (4H, m), 2.17-2.25 (2H, m), 2.36 (3H, s), 2.62 (1H, s), 3.96-4.03 (4H, m), 6.41 (1H, s), 7.09 (2H, d, J=8.0 Hz), 7.13 (2H, d, J=8.0 Hz), 7.22-7.30 (4H, m).

ESI-MS: m/z=407 (M−OH)⁺

The following compounds were synthesized in the same manner as in the above-described Intermediates 18 to 22.

TABLE 11

| Intermediate Examples | Structural Formula | Compound Data |
|---|---|---|
| 23 | 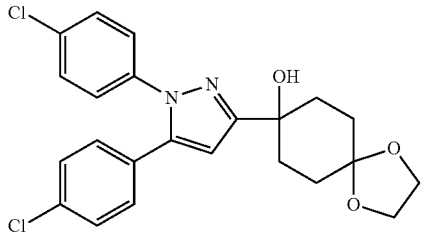 | $^1$H-NMR (400 MHz, CDCl$_3$) δ: 1.69-1.76 (2H, m), 2.16-2.25 (2H, m), 1.96-2.23 (4H, m), 2.63 (1H, s), 3.94-4.03 (4H, m), 6.45 (1H, s), 7.14 (2H, d, J = 8.4 Hz), 7.21 (2H, d, J = 8.4 Hz), 7.29-7.32 (4H, m). ESI-MS: m/z = 445 (M + H)$^+$ |
| 24 | 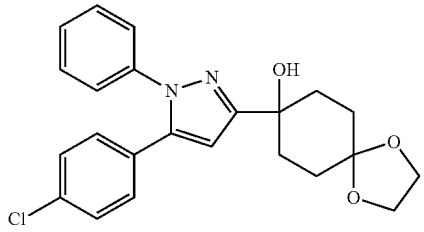 | $^1$H-NMR (400 MHz, CDCl$_3$) δ: 1.70-1.76 (2H, m), 1.98-2.14 (4H, m), 2.18-2.25 (2H, m), 2.68 (1H, s), 3.95-4.02 (4H, m), 6.45 (1H, s), 7.13-7.15 (2H, m), 7.25-7.37 (7H, m). ESI-MS: m/z = 411 (M + H)$^+$ |
| 25 | 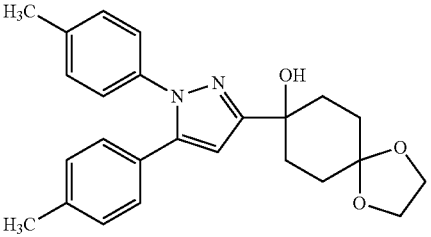 | $^1$H-NMR (400 MHz, CDCl$_3$) δ: 1.70-1.76 (2H, m), 1.98-2.04 (2H, m), 2.07-2.14 (2H, m), 2.18-2.25 (2H, m), 2.34 (3H, s), 2.35 (3H, s), 2.70 (1H, s), 3.95-4.02 (4H, m), 6.40 (1H, s), 7.08-7.11 (4H, m), 7.12 (2H, d, J = 8.4 Hz), 7.17 (2H, d, J = 8.4 Hz). ESI-MS: m/z = 387 (M − OH)$^+$ |
| 26 | 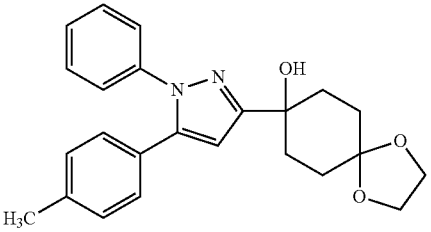 | $^1$H-NMR (400 MHz, CDCl$_3$) δ: 1.71-1.77 (2H, m), 1.98-2.05 (2H, m), 2.07-2.14 (2H, m), 2.18-2.26 (2H, m), 2.34 (3H, s), 2.69 (1H, s), 3.96-4.03 (4H, m), 6.42 (1H, s), 7.09-7.11 (4H, m), 7.26-7.35 (5H, m). ESI-MS: m/z = 373 (M − OH)$^+$ |
| 27 | 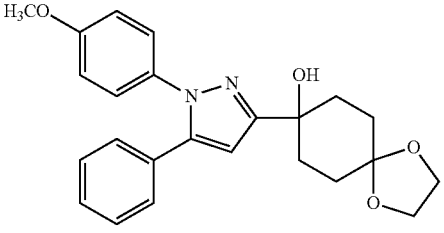 | $^1$H-NMR (400 MHz, CDCl3) δ: 1.60 (2H, m), 1.73 (2H, d, J = 12.4 Hz), 2.10 (2H, td, J = 3.4, 12.8 Hz), 2.22 (2H, td, J = 3.9, 12.4 Hz), 3.80 (3H, s), 3.96-4.03 (4H, m), 6.44 (1H, s), 6.83-6.85 (2H, m), 7.18-7.22 (4H, m), 7.26-7.30 (3H, m). |
| 28 | 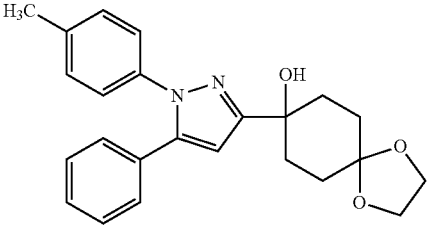 | $^1$H-NMR (400 MHz, CDCl3) δ: 1.73 (2H, d, J = 12.0 Hz), 2.01 (2H, d, J = 12.4 Hz), 2.10 (2H, td, J = 3.2 Hz), 2.22 (2H, td, J = 3.2, J = 12.4 Hz), 2.24 (3H, s), 3.96-4.03 (4H, m), 6.44 (1H, s), 7.12 (2H, d, J = 8.4 Hz), 7.16 (2H, d, J = 8.8 Hz), 7.21-7.23 (2H, m), 7.27-7.30 (3H, m). ESI-MS: m/z = 391 (M + H)$^+$ |

TABLE 11-continued

| Intermediate Examples | Structural Formula | Compound Data |
|---|---|---|
| 29 | | $^1$H-NMR (400 MHz, CDCl3) δ: 1.73 (2H, d, J = 12.4 Hz), 1.99 (2H, d, J = 12.4 Hz), 2.10 (2H, td, J = 3.2, 12.4 Hz), 2.21 (2H, td, J = 3.6, 12.4 Hz), 2.25 (3H, s), 2.73 (1H, s), 3.80 (3H, s), 3.96-4.03 (4H, m), 6.37 (1H, s), 6.82 (2H, m), 7.09-7.18 (6H, m). ESI-MS: m/z = 421 (M + H)$^+$ |
| 30 | | $^1$H-NMR (400 MHz, CDCl3) δ: 1.73 (2H, d, J = 12.4 Hz), 2.01 (2H, d, J = 12.4 Hz), 2.10 (2H, td, J = 3.2, 12.8 Hz), 2.21 (2H, td, J = 3.2, 12.4 Hz), 2.64 (1H, s), 3.82 (3H, s), 3.95-4.03 (4H, m), 6.40 (1H, s), 6.84 (2H, d, J = 8.4 Hz), 7.12 (2H, d, J = 8.8 Hz), 7.23 (2H, d, J = 8.8 Hz), 7.28 (2H, d, J = 8.8 Hz). ESI-MS: m/z = 441 (M + H)$^+$ |
| 31 | | $^1$H-NMR (400 MHz, CDCl3) δ: 1.70 (2H, d, J = 12.0 Hz), 2.01 (2H, d, J = 8.8 Hz), 2.10 (2H, td, J = 4.0, 12.8 Hz), 2.21 (2H, td, J = 3.6, 12.4 Hz), 2.71 (1H, s), 3.80 (3H, s), 3.92-4.03 (4H, m), 6.39 (1H, s), 6.81 (2H, d, J = 12.0 Hz), 7.13 (2H, d, J = 12.0 Hz), 7.22-7.35 (5H, m). |
| 32 | | $^1$H-NMR (400 MHz, CDCl3) δ: 1.71-1.74 (4H, m), 1.96-2.16 (4H, m), 187 (1H, s), 181 (3H, s), 3.94-4.01 (4H, m), 6.52 (1H, s), 6.86 (2H, d, J = 8.0 Hz), 7.19 (2H, d, J = 8.0 Hz), 7.32 (2H, d, J = 8.0 Hz), 7.54 (2H, d, J = 8.0 Hz). |
| 33 | | $^1$H-NMR (400 MHz, CDCl3) δ: 1.23 (3H, t, J = 7.6 Hz), 1.69-1.76 (2H, m), 1.98-2.26 (6H, m), 2.63 (2H, q, J = 7.6 Hz), 2.69 (1H, br), 3.81 (3H, s), 3.95-4.03 (4H, m), 6.40 (1H, s), 6.82-6.87 (2H, m), 7.12 (4H, s), 7.19-7.24 (2H, m). ESI-MS: m/z = 425 (M + H)$^+$ |
| 34 | | $^1$H-NMR (400 MHz, CDCl$_3$) δ: 1.68-1.77 (2H, m), 1.97-2.25 (6H, m), 2.35 (3H, s), 2.64 (1H, s), 3.89 (3H, s), 3.94-4.03 (4H, m), 6.40 (1H, s), 6.87 (1H, t, J = 8.8 Hz), 6.94-7.01 (1H, m), 7.07-7.13 (5H, m). ESI-MS: m/z = 425 (M + H)$^+$ |

TABLE 11-continued

| Intermediate Examples | Structural Formula | Compound Data |
|---|---|---|
| 35 | ![structure] | $^1$H-NMR (400 MHz, CDCl$_3$) δ: 1.69-1.77 (2H, m), 1.97-2.28 (9H, m), 2.64 (1H, s), 3.82 (3H, s), 3.95-4.03 (4H, m), 6.41 (1H, s), 6.83-6.89 (4H, m), 7.08 (1H, t, J = 8.0 Hz), 7.18-7.27 (2H, m). ESI-MS: m/z = 439 (M + H)$^+$ |
| 36 | ![structure] | $^1$H-NMR (400 MHz, CDCl$_3$) δ: 1.70-1.78 (2H, m), 1.97-2.27 (6H, m), 2.38 (3H, s), 2.54 (1H, s), 3.94-4.03 (4H, m), 6.45 (1H, s), 7.09-7.20 (4H, m), 7.40-7.44 (2H, m), 7.57-7.62 (2H, m). ESI-MS: m/z = 416 (M + H)$^+$ |
| 37 | ![structure] | $^1$H-NMR (400 MHz, CDCl$_3$) δ: 1.69-1.76 (2H, m), 1.97-2.26 (6H, m), 2.56 (1H, br), 3.83 (3H, s), 3.94-4.03 (4H, m), 6.52 (1H, s), 6.84-6.90 (2H, m), 7.14-720 (2H, m), 729-7.33 (2H, m), 7.55-7.59 (2H, m). ESI-MS: m/z = 432 (M + H)$^+$ |

Intermediate 38

As Intermediate 38, 1-(1-(4-methoxyphenyl)-5-(p-tolyl)-1H-pyrazol-3-yl)cyclohexan-cis-1,4-diyl diacetate:

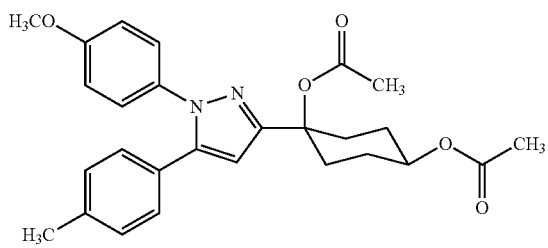

was synthesized by the following procedure.

Acetic anhydride (0.187 mL, 1.98 mmol), pyridine (0.192 mL, 2.38 mmol), and 4-dimethylaminopyridine (48.4 mg, 0.396 mmol) were added to a suspension of 1-(1-(4-methoxyphenyl)-5-(p-tolyl)-1H-pyrazol-3-yl)cyclohexan-cis-1,4-diol (Compound 3) (300 mg, 0.793 mmol) in dichloromethane (2.6 mL), and the resulting mixture was stirred at room temperature for 60 hours. Again, 4-dimethylaminopyridine (48.4 mg, 0.396 mmol) was added thereto, and the resulting mixture was stirred at room temperature for an additional 6 hours. Water was added to the reaction solution to stop the reaction, and the resulting solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain Intermediate 38 (297 mg, 0.642 mmol, 81%) as a white solid.

$^1$H-NMR (400 MHz, CDCl$_3$) δ: 1.74-1.82 (2H, m), 1.92-1.98 (2H, m), 2.01-2.08 (5H, m), 2.10 (3H, s), 2.32 (3H, s), 2.70-2.77 (2H, m), 3.80 (3H, s), 4.80-4.89 (1H, m), 6.38 (1H, s), 6.83 (2H, d, J=8.8 Hz), 7.08 (4H, s), 7.20 (2H, d, J=8.8 Hz).

ESI-MS: m/z=463 (M+H)$^+$

Intermediate 39

As Intermediate 39, c-4-methoxy-1-(1-(4-methoxyphenyl)-5-(p-tolyl)-1H-pyrazol-3-yl)-cyclohexan-r-1-yl acetate:

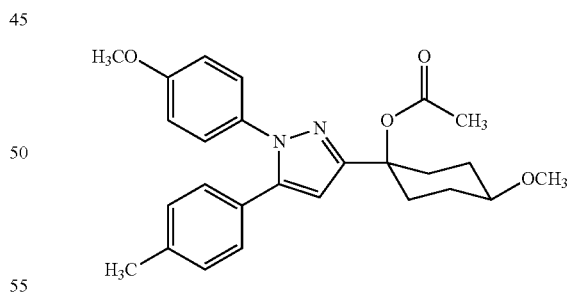

was synthesized by the following procedure.

To a solution of c-4-hydroxy-1-(1-(4-methoxyphenyl)-5-(p-tolyl)-1H-pyrazol-3-yl)cyclohexan-r-1-yl acetate (Intermediate 84) (0.150 g, 0.357 mmol) in N,N-dimethylformamide (1.8 mL), 55% sodium hydride (23.4 mg, 0.535 mmol) and methyl iodide (29.0 μL, 0.464 mmol) were added with stirring under ice-cooling, and the resulting mixture was stirred at room temperature for 9 hours. Water was added to the reaction solution with stirring under ice-cooling to stop the reaction, and the resulting solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain Intermediate 39 (124 mg, 0.284 mmol, 80%) as a white solid.

$^1$H-NMR (400 MHz, CDCl$_3$) δ: 1.60-1.68 (2H, m), 1.94-2.03 (4H, m), 2.08 (3H, s), 2.32 (3H, s), 2.69-2.76 (2H, m), 124-3.33 (1H, m), 3.39 (3H, s), 3.80 (3H, s), 6.37 (1H, s), 6.83 (2H, d, J=8.8 Hz), 7.08 (4H, s), 7.20 (2H, d, J=8.8 Hz).

ESI-MS: m/z=435 (M+H)$^+$

Intermediate 40

As Intermediate 40, 4-(4-fluoro-1-(4-methoxyphenyl)-5-(p-tolyl)-1H-pyrazol-3-yl)-c-4-hydroxy-cyclohexan-r-1-yl acetate:

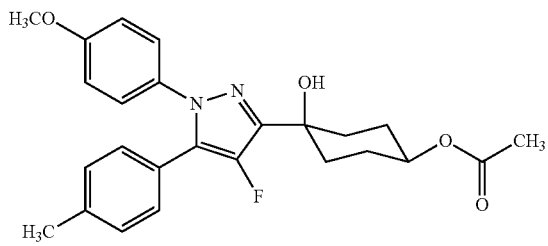

was synthesized by the following procedure.

Selectfluor™ (120 mg, 0.340 mmol) was added to a solution of c-4-hydroxy-4-(1-(4-methoxyphenyl)-5-(p-tolyl)-1H-pyrazol-3-yl)-cyclohexan-r-1-yl acetate (Compound 12) (130 mg, 0.309 mmol) in acetonitrile (3.09 mL), and the resulting mixture was stirred at room temperature for 3 hours. A saturated aqueous sodium thiosulfate solution was added to the reaction solution, and the resulting solution was extracted with ethyl acetate. The organic layer was washed with brine, and then dried over anhydrous magnesium sulfate, and concentrated under reduced pressure. The residue was purified by flash chromatography (silica gel, n-hexane/ethyl acetate) to obtain Intermediate 40 (61 mg, 0.140 mmol, 45%) as a pale yellow amorphous product.

$^1$H-NMR (400 MHz, CDCl$_3$) δ: 1.89-2.15 (11H, m), 2.35 (3H, m), 2.73 (1H, s), 3.81 (3H, s), 4.82-4.89 (1H, m), 6.84-6.86 (2H, m), 7.10-7.18 (6H, m).

ESI-MS: m/z=439 (M+H)$^+$

Intermediate 41

As Intermediate 41, 1-(1-(4-methoxyphenyl)-5-(p-tolyl)-1H-pyrazol-3-yl)-4-oxo-cyclohexan-1-yl acetate:

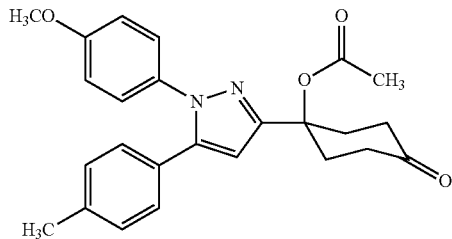

was synthesized by the following procedure.

Dess-Martin reagent (172 mg, 0.405 mmol) was added to a solution of c-4-hydroxy-1-(1-(4-methoxyphenyl)-5-(p-tolyl)-1H-pyrazol-3-yl)-cyclohexan-r-1-yl acetate (Intermediate 84) (142 mg, 0.338 mmol) in dichloromethane (3.38 mL), and the resulting mixture was stirred at 0° C. for 2 hours. The reaction solution was filtered through Celite, and the residue was purified by flash chromatography (silica gel, n-hexane/ethyl acetate) to obtain Intermediate 41 (120 mg, 0.287 mmol, 85%) as a white amorphous product.

$^1$H-NMR (400 MHz, CDCl$_3$) δ: 2.13 (3H, s), 2.33 (3H, s), 2.44-2.52 (4H, m), 2.59-2.65 (2H, m), 2.93-2.96 (2H, m), 3.81 (3H, s), 6.45 (1H, s), 6.84 (2H, d, J=8.8 Hz), 7.08 (4H, s), 7.20 (2H, d, J=8.8 Hz).

ESI-MS: m/z=419 (M+H)$^+$

Intermediate 42

As Intermediate 42, c-4-hydroxy-4-(1-(4-methoxyphenyl)-5-(p-tolyl)-1H-pyrazol-3-yl)-cis-cyclohexan-r-1-carbaldehyde:

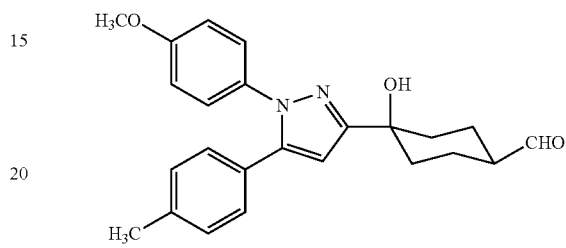

was synthesized by the following procedure.

To a solution of (methoxymethyl)triphenylphosphonium chloride (546.3 mg, 1.59 mmol) in tetrahydrofuran (1.3 mL), potassium tert-butoxide (178.7 mg, 1.59 mmol) was added at −40° C., and the resulting mixture was stirred at the same temperature for 60 minutes. A solution of 4-hydroxy-4-(1-(4-methoxyphenyl)-5-(p-tolyl)-1H-pyrazol-3-yl)cyclohexan-1-one (Compound 4) (200 mg, 0.53 mmol) in tetrahydrofuran (1.35 mL) was added dropwise to the reaction solution at −40° C., and thereafter the resulting mixture was stirred at room temperature for 1.5 hours. To the reaction solution, a 6 M aqueous hydrochloric acid solution was added at 0° C., and the resulting mixture was stirred for 12 hours. Distilled water was added to the reaction solution, and the resulting solution was extracted with ethyl acetate. The organic layer was washed with a saturated aqueous sodium hydrogen carbonate solution and brine, dried over anhydrous sodium sulfate, and concentrated under reduced pressure. The residue was purified by flash chromatography (silica gel, n-hexane/ethyl acetate) to obtain Intermediate 42 (87.5 mg, 0.23 mmol, 42%) as a colorless oily product.

$^1$H-NMR (400 MHz, CDCl$_3$) δ: 1.88-1.96 (6H, m), 2.09-2.11 (2H, m), 2.25-2.36 (5H, m), 3.80 (3H, s), 6.39 (1H, s), 6.84 (2H, d, J=8.8 Hz), 7.09-7.14 (4H, m), 7.20 (2H, d, J=8.8 Hz), 9.66 (1H, d, J=2.0 Hz).

ESI-MS: m/z=391 (M+H)$^+$

Intermediate 43

As Intermediate 43, ethyl 1,4-dioxaspiro[4.5]decan-8-carboxylate:

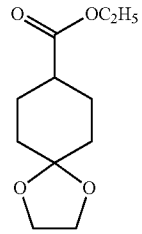

was synthesized by the following procedure.

Ethylene glycol (3.6 mL, 64.6 mmol) and p-toluenesulfonic acid monohydrate (1.12 g, 5.88 mmol) were added to a solution of ethyl 4-oxocyclohexanecarboxylate (10.0 g, 58.8 mmol) in toluene (196 mL), and the obtained solution was heated to reflux at 150° C. The resulting solution was stirred for 18 hours. To the reaction solution, a saturated sodium bicarbonate solution was added to stop the reaction, and the resulting solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain Intermediate 43 (12.3 g, 57.4 mmol, 98%) as a colorless oily compound.

$^1$H-NMR (400 MHz, CDCl$_3$) δ: 1.25 (3H, J=7.2 Hz), 1.51-1.61 (2H, m), 1.75-1.86 (4H, m), 1.90-1.98 (2H, m), 2.29-2.38 (1H, s), 3.95 (4H, s), 4.13 (2H, q, J=7.2 Hz).

ESI-MS: m/z=215 (M+H)$^+$

Intermediate 44

As Intermediate 44, ethyl 8-(benzyloxymethyl)-1,4-dioxaspiro[4.5]decan-8-carboxylate:

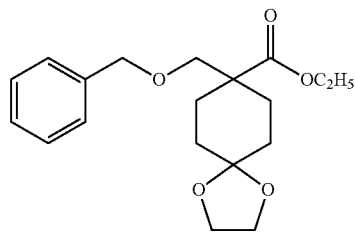

was synthesized by the following procedure.

To a solution of ethyl 1,4-dioxaspiro[4.5]decan-8-carboxylate (Intermediate 43) (500 mg, 2.33 mmol) in tetrahydrofuran (7.8 mL), 0.5 M potassium bis(trimethylsilyl)amide (a solution in toluene, 4.67 mL, 2.33 mmol) was added at −78° C., and the resulting mixture was stirred for 20 minutes. Thereafter, benzylchloromethyl ether (0.379 mL, 2.45 mmol) was added thereto, and the resulting mixture was stirred at −78° C. for 30 minutes and at room temperature for 1.5 hours. A saturated aqueous ammonium chloride solution was added to the reaction solution, and the resulting solution was extracted with ethyl acetate. The organic layer was dried over anhydrous sodium sulfate, and concentrated under reduced pressure. To the residue, a 3 M aqueous sodium hydroxide solution (1.0 mL) was added, and the resulting mixture was stirred for 4 hours. The reaction solution was extracted with ether, and the organic layer was washed with brine, dried over anhydrous sodium sulfate, and concentrated under reduced pressure. The residue was purified by flash chromatography (silica gel, n-hexane/ethyl acetate) to obtain Intermediate 44 (279 mg, 0.834 mmol, 36%) as a colorless oily compound.

$^1$H-NMR (400 MHz, CDCl$_3$) δ: 1.24 (3H, t, J=7.2 Hz), 1.52-1.68 (6H, m), 2.16-2.23 (2H, m), 3.46 (2H, s), 3.88-3.96 (4H, m), 4.17 (2H, q, J=7.2 Hz), 4.49 (2H, s), 7.25-7.39 (5H, m).

ESI-MS: m/z=335 (M+H)$^+$

Intermediate 45

As Intermediate 45, (8-(benzyloxymethyl)-1,4-dioxaspiro[4.5]decan-8-yl)methanol:

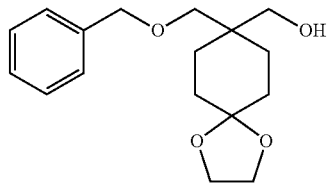

was synthesized by the following procedure.

To a solution of ethyl 8-(benzyloxymethyl)-1,4-dioxaspiro[4.5]decan-8-carboxylate (Intermediate 44) (279 mg, 0.834 mmol) in tetrahydrofuran (4.2 mL), lithium borohydride (91.0 mg, 4.17 mmol) was added with stirring under ice-cooling, and the resulting mixture was stirred at 70° C. for 4 hours. A saturated aqueous ammonium chloride solution was added to the reaction solution to stop the reaction, and the resulting solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain Intermediate 45 (183 mg, 0.625 mmol, 75%) as a colorless oily compound.

$^1$H-NMR (400 MHz, CDCl$_3$) δ: 1.48-1.66 (8H, m), 2.76 (1H, t, J=6.0 Hz), 3.43 (2H, s), 3.60 (2H, d, J=6.0 Hz), 3.91-3.95 (4H, m), 4.52 (2H, s), 7.27-7.38 (5H, m).

ESI-MS: m/z=293 (M+H)$^+$

Intermediate 46

As Intermediate 46, 8-(benzyloxymethyl)-1,4-dioxaspiro[4.5]decan-8-carboaldehyde:

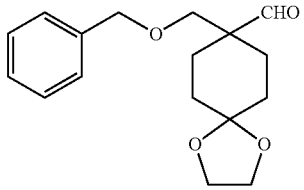

was synthesized by the following procedure.

To a solution of (8-(benzyloxymethyl)-1,4-dioxaspiro[4.5]decan-8-yl)methanol (Intermediate 45) (183 mg, 0.625 mmol) in DMSO (2.1 mL), 50% sulfur trioxide-pyridine complex (596 mg, 1.87 mmol) and triethylamine (0.522 mL, 3.75 mmol) were added, and the resulting mixture was stirred at room temperature for 20 minutes. Water was added to the reaction solution to stop the reaction, and the resulting solution was extracted with ethyl acetate. The organic layer was washed sequentially with a 20% aqueous citric acid solution, a saturated sodium bicarbonate solution and brine, dried over anhydrous sodium sulfate, and concentrated under reduced pressure. The residue was purified by flash chromatography (silica gel, n-hexane/ethyl acetate) to obtain Intermediate 46 (172 mg, 0.592 mmol, 95%) as a colorless oily compound.

$^1$H-NMR (400 MHz, CDCl$_3$) δ: 1.55-1.67 (6H, m), 2.03-2.11 (2H, m), 3.45 (2H, s), 3.90-3.95 (4H, m), 4.47 (2H, s), 7.25-7.36 (5H, m), 9.60 (1H, s).

ESI-MS: m/z=291 (M+H)$^+$

Intermediate 47

As Intermediate 47, 8-(benzyloxymethyl)-8-ethinyl-1,4-dioxaspiro[4,5]decane:

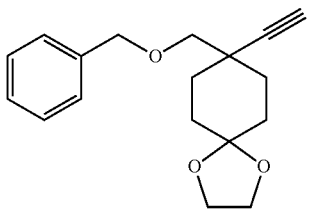

was synthesized by the following procedure.

To a solution of 8-(benzyloxymethyl)-1,4-dioxaspiro[4.5]decan-8-carboaldehyde (Intermediate 46) (100 mg, 0.344 mmol) in methanol (5.2 mL), potassium carbonate (143 mg, 1.03 mmol) and dimethyl-1-diazo-2-oxopropylphosphonate (165 mg, 0.861 mmol) were added with stirring under ice-cooling, and the resulting mixture was stirred at room temperature for 1 hour. Water was added to the reaction solution to stop the reaction, and the resulting solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain Intermediate 47 (88.9 mg, 0.310 mmol, 90%) as a colorless oily compound.

$^1$H-NMR (400 MHz, CDCl$_3$) δ: 1.52-1.71 (4H, m), 1.77-1.85 (2H, m), 1.94-2.04 (2H, m), 2.19 (1H, s), 3.38 (2H, s), 3.89-3.99 (4H, s), 4.61 (2H, s), 7.25-7.37 (5H, m).

ESI-MS: m/z=287 (M+H)$^+$

Intermediate 48

As Intermediate 48, 3-(8-(benzyloxymethyl)-1,4-dioxaspiro[4.5]decan-8-yl)-1-(ptolyl)propyn-1-ol:

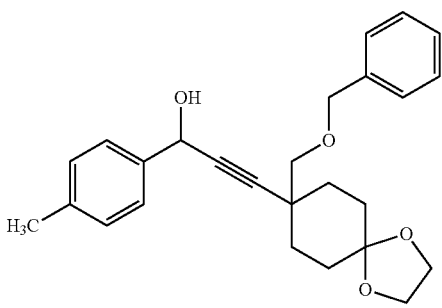

was synthesized by the following procedure.

To a solution of 8-(benzyloxymethyl)-8-ethinyl-1,4-dioxaspiro[4.5]decane (Intermediate 47) (393 mg, 1.37 mmol) in tetrahydrofuran (4.6 mL), 2.6 M n-butyllithium (a solution in hexane, 0.555 mL, 1.44 mmol) was added at −78° C., and the resulting mixture was stirred for 10 minutes. Further, 4-methylbenzaldehyde (0.178 mL, 1.51 mmol) was added thereto, and thereafter the resulting mixture was allowed to warm gradually to room temperature and stirred for 1 hour. A saturated aqueous ammonium chloride solution was added to the reaction solution, and the resulting solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain Intermediate 48 (459 mg, 1.13 mmol, 82%) as a colorless oily compound.

$^1$H-NMR (400 MHz, CDCl$_3$) δ: 1.62-1.71 (4H, m), 1.79-1.86 (2H, m), 1.92-2.02 (2H, m), 2.23 (1H, brs), 2.34 (3H, s), 3.41 (2H, s), 3.89-3.98 (4H, m), 4.59 (2H, m), 5.44 (1H, d, J=5.2 Hz), 7.15 (2H, d, J=8.0 Hz), 7.25-7.35 (5H, m), 7.43 (2H, d, J=8.0 Hz), ESI-MS: m/z=407 (M+H)$^+$ Intermediate 49

As Intermediate 49, 3-(8-(benzyloxymethyl)-1,4-dioxaspiro[4.5]decan-8-yl)-1-(ptolyl)propyn-1-one:

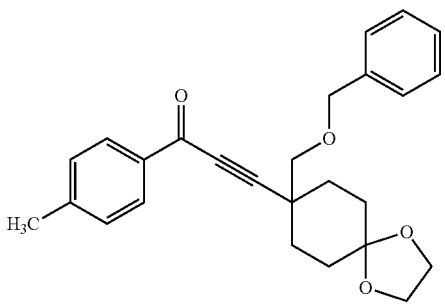

was synthesized by the following procedure.

Manganese dioxide (625 mg, 7.19 mmol) was added to a solution of 3-(8-(benzyloxymethyl)-1,4-dioxaspiro[4.5]decan-8-yl)-1-(p-tolyl)propyn-1-ol (Intermediate 48) (585 mg, 1.44 mmol) in dichloromethane (7.2 mL), and the resulting mixture was stirred at room temperature for 13 hours. The reaction solution was filtered through Celite, and thereafter the filtrate was concentrated under reduced pressure. The residue was purified by flash chromatography (silica gel, n-hexane/ethyl acetate) to obtain Intermediate 49 (540 mg, 1.33 mmol, 93%) as a colorless oily compound.

$^1$H-NMR (400 MHz, CDCl$_3$) δ: 1.71-1.80 (4H, m), 1.97-2.03 (4H, m), 2.41 (3H, s), 3.52 (2H, s), 3.91-4.00 (4H, m), 4.63 (2H, m), 7.21 (2H, d, J=8.0 Hz), 7.25-7.38 (5H, m), 8.03 (2H, d, J=8.0 Hz).

ESI-MS: m/z=405 (M+H)$^+$

Intermediate 50

As Intermediate 50, 3-(8-(benzyloxymethyl)-1,4-dioxaspiro[4.5]decan-8-yl)-1-(4-methoxyphenyl)-5-(p-tolyl)-1H-pyrazole:

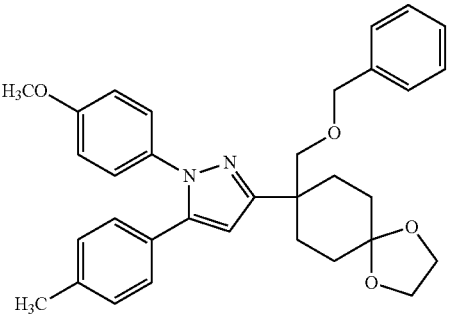

was synthesized by the following procedure.

Triethylamine (0.447 mL, 3.20 mmol) was added dropwise to a solution of 4-methoxyphenylhydrazine hydrochloric acid salt (280 mg, 1.60 mmol) in ethanol (2.7 mL), and the resulting mixture was stirred at room temperature for 30 minutes. To the reaction solution, a solution of 3-(8-(benzyloxymethyl)-1,4-dioxaspiro[4.5]decan-8-yl)-1-(p-tolyl)propyn-1-one (Intermediate 49) (540 mg, 1.33 mmol) in ethanol (2.7 mL) was added dropwise, and the resulting mixture was stirred at room temperature for 14 hours. Thereafter, the reaction solution was concentrated under reduced pressure. Water was added to the residue, and the resulting solution was extracted with ethyl acetate. The organic layer was washed with 1 M hydrochloric acid, distilled water and brine, and then dried over anhydrous magnesium sulfate, and concentrated under reduced pressure. The residue was purified by flash chromatography (silica gel, n-hexane/ethyl acetate) to obtain Intermediate 50 (458 mg, 0,872 mmol, 65%) as a white amorphous product.

$^1$H-NMR (400 MHz, CDCl$_3$) δ: 1.64-1.72 (2H, m), 1.76-1.85 (2H, m), 1.89-1.98 (2H, m), 2.27-2.35 (5H, m), 3.50 (2H, s), 3.80 (3H, s), 3.90-3.99 (4H, m), 4.49 (2H, s), 6.38 (1H, s), 6.80-6.85 (2H, m), 7.06-7.31 (11H, m).

ESI-MS: m/z=525 (M+H)$^+$

Intermediate 51

As Intermediate 51, 4-(benzyloxymethyl)-4-(1-(4-methoxyphenyl)-5-(p-tolyl)-1H-pyrazol-3-yl)cyclohexan-1-one:

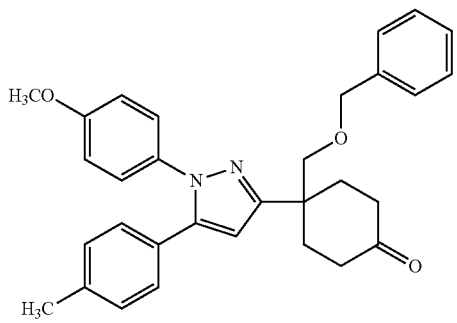

was synthesized by the following procedure.

To a solution of 3-(8-(benzyloxymethyl)-1,4-dioxaspiro [4.5]decan-8-yl)-1-(4-methoxyphenyl)-5-(p-tolyl)-1H-pyrazole (Intermediate 50) (458 mg, 0.872 mmol) in tetrahydrofuran (2.2 mL), 6 M hydrochloric acid (4.4 mL) was added, and the resulting mixture was stirred at room temperature for 15 hours. The reaction solution was cooled in ice, and a 50% aqueous sodium hydroxide solution was added dropwise thereto at 0° C. until it became basic, followed by extraction of the resulting solution with ethyl acetate. The organic layer was washed with brine, dried over anhydrous sodium sulfate, and concentrated under reduced pressure. The residue was purified by flash chromatography (silica gel, n-hexane/ethyl acetate) to obtain Intermediate 51 (387 mg, 0.804 mmol, 92%) as a white amorphous product.

$^1$H-NMR (400 MHz, CDCl$_3$) δ: 2.11-2.21 (2H, m), 2.31-2.39 (5H, m), 2.52-2.68 (4H, m), 3.57 (2H, s), 3.81 (3H, s), 4.51 (2H, s), 6.44 (1H, s), 6.83-6.88 (2H, m), 7.08-7.34 (11H, m).

ESI-MS: m/z=481 (M+H)$^+$

Intermediate 52

As Intermediate 52, 8-(4,5-bis(4-methoxyphenyl)oxazol-2-yl)-1,4-dioxaspiro[4.5]decan-8-ol:

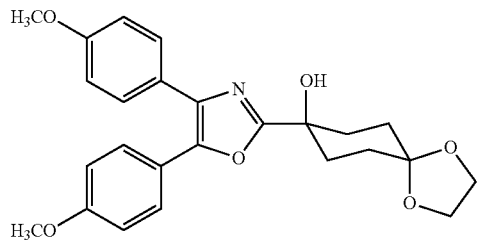

was synthesized by the following procedure.

To a solution of 2-chloro-1,4-bis(4-methoxyphenyl)oxazole (1.01 g, 3.20 mmol) in tetrahydrofuran (32 mL), which had been synthesized by the known production method (WO2007111323), 1.09 M borane-tetrahydrofuran complex (4.0 mL, 4.36 mmol) was added at 0° C., and the resulting mixture was stirred at the same temperature for 1 hour. To the reaction solution, 2.66 M n-butyllithium (1.47 mL, mmol) was added at −78° C., and the resulting mixture was stirred at the same temperature for 1 hour. To the reaction solution, 1,4-cyclohexanedione monoethylene ketal (524 mg, 3.36 mmol) was added, and the obtained solution was allowed to warm gradually to room temperature with stirring. To the reaction solution, 1 M hydrochloric acid was added to acidify it, and the resulting solution was extracted with ethyl acetate. The organic layer was dried over anhydrous magnesium sulfate, and concentrated under reduced pressure. The residue was purified by flash chromatography (silica gel, n-hexane/ ethyl acetate) to obtain Intermediate 52 (844 mg, 1.92 mmol, 60%) as a pale yellow amorphous product.

$^1$H-NMR (400 MHz, CDCl$_3$) δ: 1.71-1.80 (2H, m), 2.01-2.11 (4H, m), 2.30-2.41 (2H, m), 2.76 (1H, s), 3.83 (3H, s), 3.84 (3H, s), 3.99 (4H, dd, J=Hz), 6.89 (2H, d, J=8.8 Hz), 6.90 (2H, d, J=8.8 Hz), 7.50 (2H, d, J=8.8 Hz), 7.56 (2H, d, J=8.8 Hz).

Intermediate 53

As Intermediate 53, 1,4-dioxaspiro[4.5]decan-8-carboxyamide:

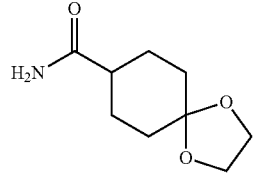

was synthesized by the following procedure.

Triethylamine (5.87 mL, 42.1 mmol) and n-propyl chloroformate were added at 0° C. to a solution of 1,4-dioxaspiro [4.5]decan-8-carboxylic acid (823 mg, 4.42 mmol) in tetrahydrofuran (22 mL), and the resulting mixture was stirred at the same temperature for 1 hour. After adding dropwise, the resulting mixture was stirred at room temperature for 30 minutes. To the reaction solution, 28% aqueous ammonia (1.5 mL) was added, and the resulting mixture was stirred at room temperature for 1 hour. The organic layer was separated from the reaction solution, dried over sodium sulfate and concentrated under reduced pressure. The residue was purified by flash chromatography (silica gel, n-hexane/ethyl acetate) to obtain Intermediate 53 (694 mg, 3.75 mmol, 85%) as a colorless amorphous product.

$^1$H-NMR (400 MHz, CDCl$_3$) δ: 1.53-1.61 (2H, m), 1.72-1.86 (4H, m), 1.91-1.98 (2H, m), 2.17-2.25 (1H, m), 3.95 (4H, s), 5.29 (1H, brs), 5.46 (1H, brs).

ESI-MS: m/z=186 (M+H)$^+$

Intermediate 54

As Intermediate 54, 1,4-dioxaspiro[4.5]decan-8-carbothioamide:

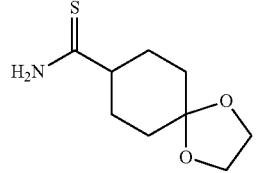

was synthesized by the following procedure.

Lawesson's reagent (337 mg, 0.834 mmol) was added to a solution of 1,4-dioxaspiro[4.5]decan-8-carboxyamide (Intermediate 53) (281 mg, 1.52 mmol) in toluene (5 mL), and the resulting mixture was stirred at 100° C. for 1 hour and then allowed to cool to room temperature. Methanol was added to the reaction solution, and the obtained solution was concentrated under reduced pressure. The residue was purified by flash chromatography (silica gel, n-hexane/ethyl acetate) to obtain Intermediate 54 (147 mg, 0.730 mmol, 48%) as a white solid.

$^1$H-NMR (400 MHz, CDCl$_3$) δ: 1.57-1.66 (2H, m), 1.79-1.90 (4H, m), 1.97-2.03 (2H, m), 2.64-2.72 (1H, m), 3.96 (4H, s), 6.89 (1H, brs), 7.46 (1H, brs).

ESI-MS: m/z=202 (M+H)$^+$

Intermediate 55

As Intermediate 55, 8-(4-(4-methoxyphenyl)-5-(p-tolyl)thiazol-2-yl)-1,4-dioxaspiro[4.5]decane:

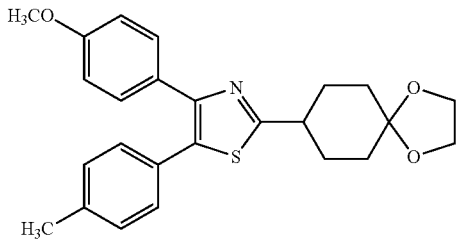

was synthesized by the following procedure.

A solution of 1,4-dioxaspiro[4.5]decane-8-carbothioamide (Intermediate 54) (389 mg, 1.93 mmol) and 2-bromo-1-(4-methoxyphenyl)-2-(p-tolyl)ethanone (588 mg, 1.84 mmol) in acetonitrile (9.2 mL) was stirred at room temperature for 4 hours. A saturated aqueous sodium hydrogen carbonate solution was added to the reaction solution, and the resulting solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain Intermediate 55 (630 mg, 1.49 mmol, 81%) as a colorless amorphous product.

$^1$H-NMR (400 MHz, CDCl$_3$) δ: 1.68-1.76 (2H, m), 1.88-1.98 (4H, m), 2.18-2.24 (2H, m), 2.35 (3H, s), 3.05-3.13 (1H, m), 3.80 (3H, s), 3.99 (4H, s), 6.79-6.82 (2H, m), 7.11 (2H, d, J=8.0 Hz), 7.22 (2H, d, J=8.0 Hz), 7.43-7.46 (2H, m).

ESI-MS: m/z=422 (M+H)$^+$

Intermediate 56

As Intermediate 56, 8-(4-(4-methoxyphenyl)-5-(p-tolyl)thiazol-2-yl)-1,4-dioxaspiro[4.5]decan-8-ol:

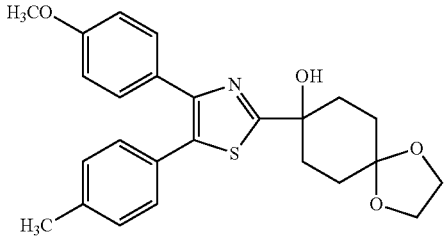

was synthesized by the following procedure.

To a solution of 8-(4-(4-methoxyphenyl)-5-(p-tolyl)thiazol-2-yl)-1,4-dioxaspiro[4.5]decane (Intermediate 55) (734 mg, 1.74 mmol) in tetrahydrofuran (8.7 mL), a 1.63 M n-butyllithium/n-hexane solution (1.17 mL) was added at −78° C., and the resulting mixture was stirred at the same temperature for 1 hour. The reaction solution was added at −78° C. to a solution of 3-phenyl-2-(phenylsulfonyl)-1,2-oxaziridine (546 mg, 2.09 mmol) in tetrahydrofuran (8.7 mL), and the obtained solution was allowed to warm gradually to room temperature with stirring. Distilled water was added to the reaction solution, and the resulting solution was extracted with ethyl acetate. The organic layer was washed with brine, and then dried over sodium sulfate, and concentrated under reduced pressure. The residue was purified by flash chromatography (silica gel, n-hexane/ethyl acetate) to obtain Intermediate 56 (417 mg, 0.954 mmol, 55%) as a colorless amorphous product.

$^1$H-NMR (400 MHz, CDCl$_3$) δ: 1.73-1.79 (2H, m), 2.03-2.10 (4H, m), 2.32-2.39 (2H, m), 2.37 (3H, s), 2.78 (1H, s), 3.84 (3H, s), 3.97-4.02 (4H, m), 6.88-6.92 (2H, m), 7.16 (2H, d, J=8.4 Hz), 7.47 (2H, d, J=8.4 Hz), 7.55-7.58 (2H, m).

ESI-MS: m/z=438 (M+H)$^+$

Intermediate 57

As Intermediate 57, 4-hydroxy-4-(1-(4-methoxyphenyl)-5-(p-tolyl)-1H-pyrazol-3-yl)cis-cyclohexyl 2-benzyloxycarbonylaminoacetate:

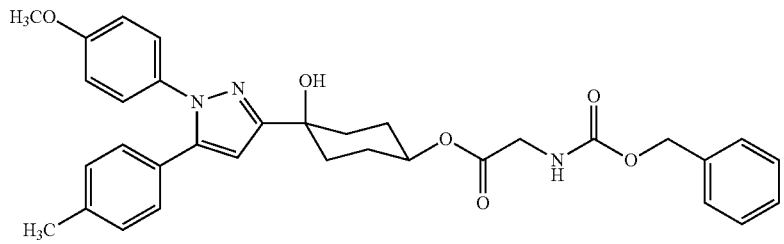

was synthesized by the following procedure.

Triethylamine (0.084 mL, 0.60 mmol), 2-benzyloxycarbonylamino acetic acid (46.2 mg, 0.241 mmol), 1-ethyl-3-(3-dimethylaminopropyl)carbodiimide hydrochloric acid salt (46.2 mg, 0.241 mmol), and 1-hydroxybenzotriazole (15.4 mg, 0.100 mmol) were added at room temperature to a solution of 1-(1-(4-methoxyphenyl)-5-(p-tolyl)-1H-pyrazol-3-yl)-cyclohexan-cis-1,4-diol (Compound 3) (76.0 mg, 0.201 mmol) in dichloromethane (2.00 mL), and the resulting mixture was stirred for 20 hours. Distilled water was added to the reaction solution, and the resulting solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain Intermediate 57 (33.2 mg, 0.058 mmol, 29%) as a colorless amorphous product.

¹H-NMR (400 MHz, CDCl₃) δ: 1.91-2.07 (8H, m), 2.33 (3H, s), 2.75 (1H, s), 3.80 (3H, s), 3.98-3.99 (2H, m), 4.89-4.94 (1H, m), 5.14 (2H, s), 5.33-5.35 (1H, m), 6.36 (1H, s), 6.82-6.86 (2H, m), 7.08-7.10 (4H, m), 7.17-7.21 (2H, m), 7.29-7.38 (5H, m).
ESI-MS: m/z=552 (M−OH)⁺

Intermediate 58

As Intermediate 58, (S)-4-hydroxy-4-(1-(4-methoxyphenyl)-5-(p-tolyl)-1H-pyrazol-3-yl)-cis-cyclohexyl 2-(benzyloxycarbonylamino)-3-methylbutanoate was synthesized in the same manner as Intermediate 57.

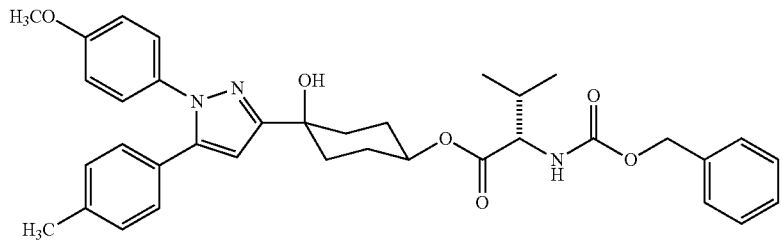

¹H-NMR (400 MHz, CDCl₃) δ: 0.92 (3H, d, J=6.4 Hz), 0.99 (3H, d, J=6.4 Hz), 1.89-2.10 (8H, m), 2.16-2.24 (1H, m), 2.34 (3H, s), 2.63 (1H, s), 3.81 (3H, s), 4.30-4.33 (1H, m), 4.88-4.95 (1H, m), 5.12 (2H, s), 5.28-5.30 (1H, m), 6.36 (1H, s), 6.78-6.82 (2H, m), 7.09-7.10 (4H, m), 7.18-7.24 (2H, m), 7.29-7.38 (5H, m).
ESI-MS: m/z=594 (M−OH)⁺

Intermediate 59

As Intermediate 59, (S)-4-hydroxy-4-(1-(4-methoxyphenyl)-5-(p-tolyl)-1H-pyrazol-3-yl)cyclohexyloxy)methyl 2-(benzyloxycarbonylamino)-3-methylbutanoate:

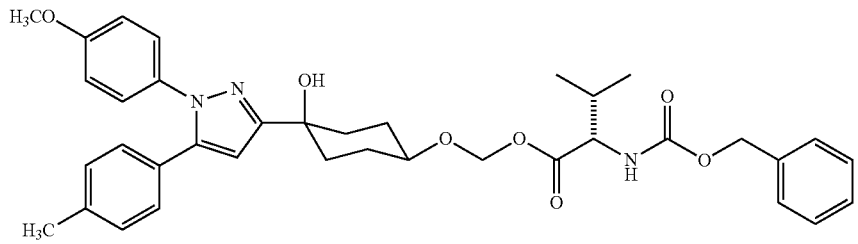

was synthesized by the following procedure.

Molecular sieves 4A (300 mg) and diisopropylethylamine (0.210 mL, 1.21 mmol) were added at room temperature to a solution of 1-(1-(4-methoxyphenyl)-5-(p-tolyl)-1H-pyrazol-3-yl)-cyclohexan-cis-1,4-diol (Compound 3) (199 mg, 0.506 mmol) in dichloromethane (3.00 mL), and the obtained mixture was cooled to −50° C. Then, (S)-iodomethyl 2-benzyloxycarbonylamino-3-methylbutanoate (0.187 mL, 1.26 mmol) and silver trifluoromethanesulfonate (232 mg, 0.904 mmol) were added thereto at the same temperature, and the resulting mixture was stirred for 2 hours, followed by stirring the mixture at −30° C. for 14 hours. A saturated sodium bicarbonate solution was added to the reaction solution, and the resulting solution was filtered through Celite. The filtrate was washed with brine, and the organic layer was dried over anhydrous sodium sulfate and concentrated under reduced pressure. The residue was purified by flash chromatography (silica gel, n-hexane/ethyl acetate) to obtain Intermediate 59 (123 mg, 0.192 mmol, 64%) as a colorless amorphous product.

¹H-NMR (400 MHz, CDCl₃) δ: 0.92 (3H, d, J=6.4 Hz), 1.01 (3H, d, J=6.4 Hz), 1.88-1.99 (6H, m), 2.02-2.09 (2H, m), 2.20-2.26 (1H, m), 2.34 (3H, s), 2.50 (1H, s), 3.66-3.72 (1H, m), 3.81 (3H, s), 4.32-4.36 (1H, m), 5.12 (2H, s), 5.38 (1H, d, J=6.4 Hz), 5.50 (1H, d, J=6.4 Hz), 6.37 (1H, s), 6.83-6.87 (2H, m), 7.08-7.11 (4H, m), 7.18-7.24 (2H, m), 7.29-7.38 (5H, m).
ESI-MS: m/z=624 (M−OH)⁺

Intermediate 60

As Intermediate 60, dibenzyl 4-hydroxy-4-(1-(4-methoxyphenyl)-5-(p-tolyl)-1H-pyrazol-3-yl)-cis-cyclohexyl phosphate:

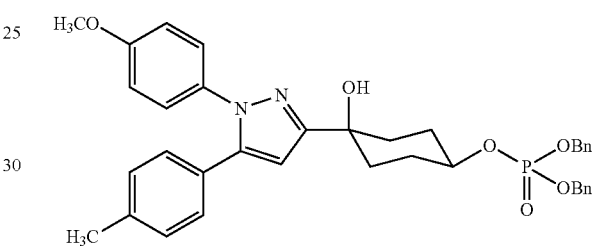

was synthesized by the following procedure.

To a solution of 1-(1-(4-methoxyphenyl)-5-(p-tolyl)-1H-pyrazol-3-yl)cyclohexan-cis-1,4-diol (Compound 3) (200 mg, 0.528 mmol) in tetrahydrofuran (2.6 mL), 55% sodium hydride (55.3 mg, 1.27 mmol) and tetrabenzylpyrophosphonate (370 mg, 0.687 mmol) were sequentially added with stirring under ice-cooling, and the resulting mixture was stirred at room temperature for 15 hours. The reaction solution was cooled in ice, and water was added thereto. The resulting solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain Intermediate 60 (251 mg, 0.393 mmol, 74%) as a colorless transparent oily compound.

¹H-NMR (400 MHz, CDCl₃) δ: 1.87-2.11 (8H, m), 2.33 (3H, s), 3.79 (3H, s), 4.42-4.51 (1H, m), 5.00-5.12 (4H, m), 6.34 (1H, s), 6.81-6.87 (2H, m), 7.09 (4H, s), 7.16-7.23 (2H, m), 7.29-7.37 (10H, m).
ESI-MS: m/z=639 (M+H)⁺

Compound 4

As Compound 4, 4-hydroxy-4-(1-(4-methoxyphenyl)-5-(p-tolyl)-1H-pyrazol-3-yl)cyclohexan-1-one:

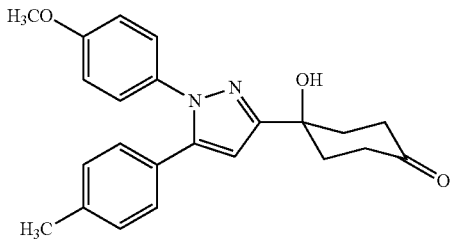

was synthesized by the following procedure.

To a solution of 8-(1-(4-methoxyphenyl)-5-(p-tolyl)-1H-pyrazol-3-yl)-1,4-dioxaspiro[4.5]decan-8-ol (Intermediate 18) (14.6 g, 34.7 mmol) in tetrahydrofuran (69.4 mL), 6 M hydrochloric acid (138.9 mL) was added, and the resulting mixture was stirred at room temperature for 15 hours. The reaction solution was cooled in ice, and a 50% aqueous sodium hydroxide solution was added dropwise thereto at 0° C. until it became basic, followed by extraction of the resulting solution with ethyl acetate. The organic layer was washed with brine, dried over anhydrous sodium sulfate, and concentrated under reduced pressure. The residue was purified by recrystallization (n-hexane/ethyl acetate, 70° C.) to obtain Compound 4 (10.5 g, 27.9 mmol, 80%) as a white solid.

$^1$H-NMR (400 MHz, CDCl$_3$) δ: 2.33-2.43 (9H, m), 2.87-2.95 (3H, m), 3.82 (3H, s), 6.39 (1H, s), 6.86 (2H, d, J=8.8 Hz), 7.10 (4H, s), 7.22 (2H, d, J=8.8 Hz).

IR (KBr, cm$^{-1}$): 3321, 2929, 1712, 1518, 1463, 1299, 1249, 1179, 1114, 1027, 961, 821.

ESI-MS: m/z=377 (M+H)$^+$

Intermediate 62

As Intermediate 62, 4-hydroxy-4-(1-(4-methoxyphenyl)-5-(6-methylpyridin-3-yl)-1H-pyrazol-3-yl)-cyclohexan-1-one:

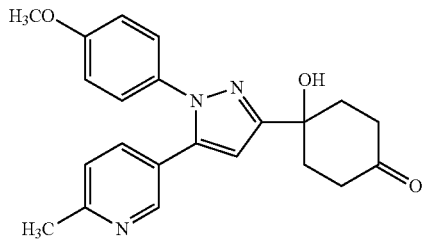

was synthesized by the following procedure.

To a solution of 8-(1-(4-methoxyphenyl)-5-(6-methylpyridin-3-yl)-1H-pyrazol-3-yl)-1,4-dioxaspiro[4.5]decan-8-ol (Intermediate 19) (128.8 mg, 0.30 mmol) in tetrahydrofuran (0.6 mL), 6 M hydrochloric acid (1.2 mL) was added, and the resulting mixture was stirred at room temperature for 3 hours. The reaction solution was cooled in ice, and a 50% aqueous sodium hydroxide solution was added dropwise thereto at 0° C. until it became basic, followed by extraction of the resulting solution with ethyl acetate. The organic layer was washed with brine, dried over anhydrous sodium sulfate, and concentrated under reduced pressure. The residue was purified by flash chromatography (silica gel, n-hexane/ethyl acetate) to obtain Intermediate 62 (109.5 mg, 0.29 mmol, 96%) as an amorphous product.

$^1$H-NMR (400 MHz, CDCl$_3$) δ: 2.34-2.44 (6H, m), 2.55 (3H, s), 2.87-2.95 (2H, m), 3.18 (1H, s), 3.82 (3H, s), 6.49 (1H, s), 6.87 (2H, d, J=8.8 Hz), 7.08 (1H, d, J=8.1 Hz), 7.19 (2H, d, J=8.8 Hz), 7.35 (1H, dd, J=2.2, 8.1 Hz), 8.40 (1H, d, J=2.2 Hz).

ESI-MS: m/z=378 (M+H)$^+$

Intermediate 63

As Intermediate 63, 4-(1,5-bis(4-methoxyphenyl)-1H-pyrazol-3-yl)-4-hydroxy-cyclohexan-1-one:

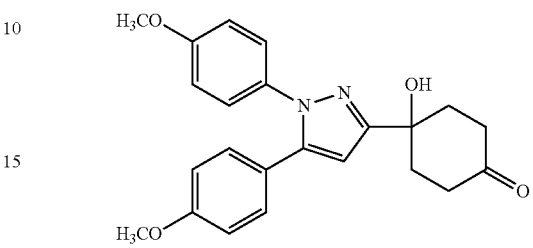

was synthesized by the following procedure.

To a solution of 8-(1,5-bis(4-methoxyphenyl)-1H-pyrazol-3-yl)-1,4-dioxaspiro[4.5]decan-8-ol (Intermediate 20) (658 mg, 1.50 mmol) in tetrahydrofuran (3.75 mL), 6 M hydrochloric acid (7.5 mL) was added at 0° C., and the resulting mixture was stirred at room temperature for 5 hours. The reaction solution was neutralized by pouring it into an ice-cooled 10% aqueous sodium hydroxide solution. The resulting solution was then basified by adding thereto a saturated sodium bicarbonate solution, and extracted with ethyl acetate. The organic layer was dried over anhydrous magnesium sulfate, and concentrated under reduced pressure. The residue was purified by flash chromatography (silica gel, n-hexane/ethyl acetate) to obtain Intermediate 63 (523 mg, 1.33 mmol, 89%) as an amorphous product.

$^1$H-NMR (400 MHz, CDCl$_3$) δ: 2.30-2.45 (6H, m), 2.86-2.96 (2H, m), 2.99 (1H, s), 3.80 (3H, s), 3.82 (3H, s), 6.36 (1H, s), 6.82 (2H, d, J=8.8 Hz), 6.87 (2H, d, J=8.8 Hz), 7.13 (2H, d, J=8.8 Hz), 7.21 (2H, d, J=8.8 Hz).

ESI-MS: m/z=393 (M+H)$^+$

Intermediate 64

As Intermediate 64, 4-(5-(4-chlorophenyl)-1-(4-methoxyphenyl)-1H-pyrazol-3-yl)-4-hydroxy-cyclohexan-1-one:

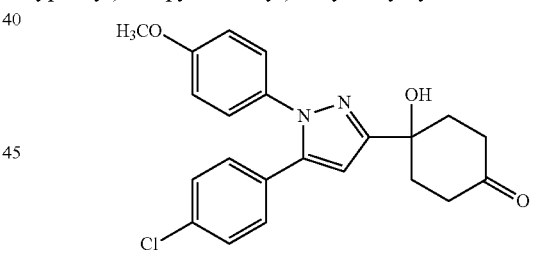

was synthesized by the following procedure.

To a solution of 8-(5-(4-chlorophenyl)-1-(4-methoxyphenyl)-1H-pyrazol-3-yl)-1,4-dioxaspiro[4.5]decan-8-ol (Intermediate 21) (756 mg, 1.71 mmol) in tetrahydrofuran (4.3 mL), 6 M hydrochloric acid (8.6 mL) was added, and the resulting mixture was stirred at room temperature for 15 hours. The reaction solution was cooled in ice, and a 50% aqueous sodium hydroxide solution was added dropwise thereto at 0° C. until it became basic, followed by extraction of the resulting solution with ethyl acetate. The organic layer was washed with brine, dried over anhydrous sodium sulfate, and concentrated under reduced pressure. The residue was purified by flash chromatography (silica gel, n-hexane/ethyl acetate) to obtain Intermediate 64 (619 mg, 1.56 mmol, 91%) as an amorphous product.

$^1$H-NMR (400 MHz, CDCl$_3$) δ: 2.31-2.45 (6H, m), 2.85-2.98 (3H, m), 3.82 (3H, s), 6.43 (1H, s), 6.86-6.90 (2H, m), 7.14 (2H, d, J=8.8 Hz), 7.19 (2H, d, J=8.8 Hz), 7.26-7.29 (2H, m).

ESI-MS: m/z=397 (M+H)$^+$

Intermediate 65

As Intermediate 65, 4-hydroxy-4-(1-(4-chlorophenyl)-5-(p-tolyl)-1H-pyrazol-3-yl)cyclohexan-1-one:

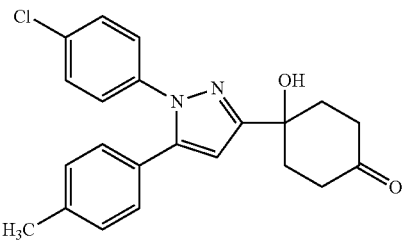

was synthesized by the following procedure.

To a solution of 8-(1-(4-chlorophenyl)-5-(p-tolyl)-1H-pyrazol-3-yl)-1,4-dioxaspiro[4.5]decan-8-ol (Intermediate 22) (931 mg, 2.19 mmol) in tetrahydrofuran (5.5 mL), 6 M hydrochloric acid (11 mL) was added, and the resulting mixture was stirred at room temperature for 15 hours. The reaction solution was basified by pouring it into a saturated aqueous sodium hydrogen carbonate solution, and the resulting solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain Intermediate 65 (513 mg, 1.35 mmol, 61%) as a white solid.

$^1$H-NMR (400 MHz, CDCl$_3$) δ: 2.32-2.36 (4H, m), 2.36 (3H, s), 2.38-2.44 (2H, m), 2.87-2.95 (2H, m), 2.90 (1H, s), 6.41 (1H, s), 7.10 (2H, d, J=8.0 Hz), 7.14 (2H, d, J=8.0 Hz), 7.23 (2H, d, J=8.8 Hz), 7.31 (2H, d, J=8.8 Hz).

ESI-MS: m/z=381 (M+H)$^+$

The following compounds were synthesized in the same manner as in the above-described Intermediates.

TABLE 12

| Intermediate Examples | Structural Formula | Compound Data |
| --- | --- | --- |
| 66 | | $^1$H-NMR (400 MHz, CDCl$_3$) δ: 2.31-2.45 (6H, m), 2.86-2.96 (3H, m), 6.45 (1H, s), 7.15 (2H, d, J = 8.8 Hz), 7.22 (2H, d, J = 8.8 Hz), 7.31-7.35 (4H, m). ESI-MS: m/z = 401 (M + H)$^+$ |
| 67 | | $^1$H-NMR (400 MHz, CDCl$_3$) δ: 2.32-2.44 (6H, m), 2.85-2.95 (2H, m), 3.10 (1H, brs), 6.45 (1H, s), 7.13-7.16 (2H, m), 7.26-7.39 (7H, m). ESI-MS: m/z = 367 (M + H)$^+$ |
| 68 | | $^1$H-NMR (400 MHz, CDCl$_3$) δ: 2.32-2.45 (6H, m), 2.34 (3H, s), 2.36 (3H, s), 2.87-2.95 (2H, m), 2.98 (1H, s), 6.37 (1H, s), 7.10-7.19 (8H, m). ESI-MS: m/z = 361 (M + H)$^+$ |
| 69 | | $^1$H-NMR (400 MHz, CDCl$_3$) δ: 2.32-2.45 (6H, m), 2.35 (3H, s), 2.87-2.96 (2H, m), 2.97 (1H, s), 6.41 (1H, s), 7.09-7.13 (4H, m), 7.27-7.37 (5H, m). ESI-MS: m/z = 347 (M + H)$^+$ |

TABLE 12-continued

| Intermediate Examples | Structural Formula | Compound Data |
|---|---|---|
| 70 | | $^1$H-NMR (400 MHz, CD$_3$OD) δ: 2.44-2.38 (6H, m), 2.87-2.96 (3H, m), 3.82 (3H, s), 6.43 (1H, s), 6.86 (2H, d, J = 9.0 Hz), 7.19-7.24 (4H, m), 7.29-7.32 (3H, m).<br>ESI-MS: m/z = 363 (M + H)$^+$ |
| 71 | | $^1$H-NMR (400 MHz, CDCl$_3$) δ: 2.32-2.44 (2H, m), 2.35-2.39 (5H, m), 2.43-2.50 (2H, m), 2.89-2.96 (2H, m), 6.43 (1H, s), 7.13 (2H, d, J = 8.8 Hz), 7.17 (2H, d, J = 8.8 Hz), 7.20-7.24 (2H, m), 7.29-7.32 (3H, m).<br>ESI-MS: m/z = 347 (M + H)$^+$ |
| 72 | | $^1$H-NMR (400 MHz, CDCl3) δ: 2.31-2.34 (2H, m), 2.36 (3H, s), 2.37-2.39 (2H, m), 2.41-2.43 (2H, m), 2.86-2.96 (2H, m), 2.99 (1H, s), 3.80 (3H, s), 6.36 (1H, s), 6.83 (2H, d, J = 8.8 Hz), 7.13-7.19 (6H, m).<br>ESI-MS: m/z = 377 (M + H)$^+$ |
| 73 | | $^1$H-NMR (400 MHz, CDCl3) δ: 2.31-2.35 (4H, m), 2.38-2.43 (2H, m), 2.86-2.96 (3H, m), 3.82 (3H, s), 6.38 (1H, s), 6.84 (2H, d, J = 9.0 Hz), 7.13 (2H, d, J = 11.7 Hz), 7.23 (2H, t, J = 8.9 Hz), 7.31 (2H, d, J = 11.5 Hz).<br>ESI-MS: m/z = 397 (M + H)$^+$ |
| 74 | | $^1$H-NMR (400 MHz, CDCl3) δ: 2.31-2.45 (6H, m), 2.86-2.96 (2H, m), 3.02 (1H, s), 3.80 (3H, s), 6.37 (1H, s), 6.83 (2H, d, J = 8.8 Hz), 7.14 (2H, d, J = 8.8 Hz), 7.28-7.37 (5H, m). |
| 75 | | $^1$H-NMR (400 MHz, CDCl3) δ: 2.33-2.37 (4H, m), 2.39-2.43 (2H, m), 2.87-2.95 (3H, m), 3.83 (3H, s), 6.50 (1H, s), 6.89 (2H, d, J = 8.0 Hz), 7.20 (2H, d, J = 8.0 Hz), 7.33 (2H, d, J = 8.0 Hz), 7.56 (2H, d, J = 8.0 Hz).<br>ESI-MS: m/z = 431 (M + H)$^+$ |

TABLE 12-continued

| Intermediate Examples | Structural Formula | Compound Data |
| --- | --- | --- |
| 76 | | $^1$H-NMR (400 MHz, CDCl3) δ: 1.23 (3H, t, J = 7.6 Hz), 2.31-2.45 (6H, m), 2.64 (2H, q, J = 7.6 Hz), 2.86-2.96 (3H, m), 3.82 (3H, s), 6.39 (1H, s), 6.83-6.89 (2H, m), 7.13 (4H, s), 7.20-7.25 (2H, m).<br>ESI-MS: m/z = 391 (M + H)$^+$ |
| 77 | | $^1$H-NMR (400 MHz, CDCl$_3$) δ: 2.31-2.45 (9H, m), 2.86-2.97 (3H, m), 3.90 (3H, s), 6.39 (1H, s), 6.89 (1H, t, J = 8.8 Hz), 6.98-7.01 (1H, m), 7.08-7.15 (5H, m).<br>ESI-MS: m/z = 395 (M + H)$^+$ |
| 78 | | $^1$H-NMR (400 MHz, CDCl$_3$) δ: 2.26 (3H, d, J = 1.6 Hz), 2.31-2.45 (6H, m), 2.85-2.96 (3H, m), 3.82 (3H, s), 6.41 (1H, s), 6.84-6.90 (4H, m), 7.10 (1H, t, J = 8.0 Hz), 7.18-7.23 (2H, m).<br>ESI-MS: m/z = 395 (M + H)$^+$ |
| 79 | | $^1$H-NMR (400 MHz, CDCl$_3$) δ: 2.30-2.45 (9H, m), 2.83 (1H, s), 2.86-2.97 (2H, m), 6.45 (1H, s), 7.10-7.20 (4H, m), 7.40-7.45 (2H, m), 7.59-7.64 (2H, m).<br>ESI-MS: m/z = 372 (M + H)$^+$ |
| 80 | | $^1$H-NMR (400 MHz, CDCl$_3$) δ: 2.31-2.46 (6H, m), 2.84-2.96 (3H, m), 3.83 (3H, s), 6.53 (1H, s), 6.87-6.92 (2H, m), 7.15-7.21 (2H, m), 7.30-7.34 (2H, m), 7.57-7.61 (2H, m).<br>ESI-MS: m/z = 425 (M + H)$^+$ |

Intermediate 81

As Intermediate 81, 4-(4-chloro-1-(4-methoxyphenyl)-5-(p-tolyl)-1H-pyrazol-3-yl)-c-4-hydroxy-cyclohexan-r-1-yl acetate:

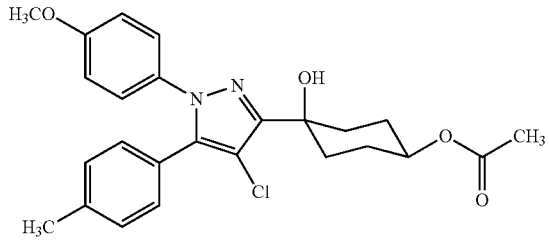

was synthesized by the following procedure.

To a solution of c-4-hydroxy-4-(1-(4-methoxyphenyl)-5-(p-tolyl)-1H-pyrazol-3-yl)cyclohexan-r-1-yl acetate (Compound 12) (140 mg, 0.333 mmol) in acetonitrile (1.66 mL), N-chlorosuccinimide (49 mg, 0.366 mmol) was added. The resulting mixture was stirred at 80° C. for 15 hours, and allowed to cool to room temperature. Brine was added to the reaction solution, and the resulting solution was extracted with ethyl acetate. The organic layer was dried over anhydrous magnesium sulfate, and concentrated under reduced pressure. The residue was purified by flash chromatography (silica gel, n-hexane/ethyl acetate) to obtain Intermediate 81 (67 mg, 0.147 mmol, 44%) as a white solid.

$^1$H-NMR (400 MHz, CDCl$_3$) δ: 1.92-2.04 (6H, m), 2.28-2.36 (8H, m), 3.10 (1H, s), 3.79 (3H, s), 4.85-4.88 (1H, m), 6.80-6.82 (2H, m), 7.11-7.16 (6H, m).

Intermediate 82

As Intermediate 82, 4-(4,5-bis(4-methoxyphenyl)oxazol-2-yl)-4-hydroxycyclohexan-1-one:

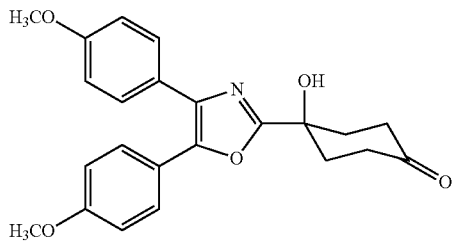

was synthesized by the following procedure.

To a solution of 8-(4,5-bis(4-methoxyphenyl)oxazol-2-yl)-1,4-dioxaspiro[4.5]decan-8-01 (Intermediate 52) (781 mg, 1.78 mmol) in tetrahydrofuran (4.5 mL), 6 M hydrochloric acid (9.0 mL) was added at 0° C., and the resulting mixture was stirred at room temperature for 2 hours. The reaction solution was cooled to 0° C., and alkalified by addition of a 10% aqueous sodium hydroxide solution and a saturated sodium bicarbonate solution. The resulting solution was extracted with ethyl acetate. The organic layer was dried over anhydrous magnesium sulfate, and concentrated under reduced pressure. The residue was purified by recrystallization (ethyl acetate/n-hexane) to obtain Intermediate 82 (445 mg, 1.13 mmol, 63%) as a pale yellow solid.

$^1$H-NMR (400 MHz, CDCl$_3$) δ: 2.32-2.54 (6H, m), 2.81-2.92 (2H, m), 3.17 (1H, m), 3.84 (6H, s), 6.90 (2H, d, J=8.8 Hz), 6.91 (2H, d, J=8.8 Hz), 7.49 (2H, d, J=8.8 Hz), 7.56 (2H, d, J=8.8 Hz).

ESI-MS: m/z=394 (M+H)$^+$

Intermediate 83

As Intermediate 83, 4-hydroxy-4-(4-(4-methoxyphenyl)-5-(p-tolyl)thiazol-2-yl)cyclohexan-1-one:

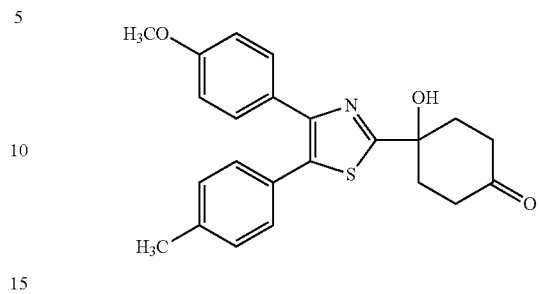

was synthesized by the following procedure.

To a solution of 8-(4-(4-methoxyphenyl)-5-(p-tolyl)thiazol-2-yl)-1,4-dioxaspiro[4.5]decan-8-ol (Intermediate 56) (469 mg, 1.07 mmol) in tetrahydrofuran (5.4 mL), 6 M hydrochloric acid (5.4 mL) was added at 0° C., and the resulting mixture was stirred at room temperature for 14 hours. The reaction solution was basified by pouring it into a saturated aqueous sodium hydrogen carbonate solution, and the resulting solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain Intermediate 83 (352 mg, 0.895 mmol, 83%) as a white solid.

$^1$H-NMR (400 MHz, CDCl$_3$) δ: 2.33-2.51 (6H, m), 2.37 (3H, s), 2.86-2.95 (2H, m), 3.50 (1H, s), 3.81 (3H, s), 6.81-6.84 (2H, m), 7.14 (2H, d, J=8.0 Hz), 7.24 (2H, d, J=8.0 Hz), 7.44-7.48 (2H, m).

ESI-MS: m/z=394 (M+H)$^+$

Intermediate 84

As Intermediate 84, c-4-hydroxy-1-(1-(4-methoxyphenyl)-5-(p-tolyl)-1H-pyrazol-3-yl)-cyclohexan-r-1-yl acetate:

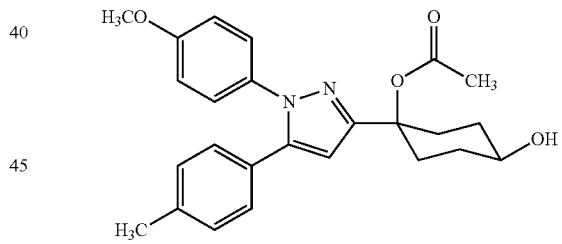

was synthesized by the following procedure.

Potassium carbonate (89.0 mg, 0.642 mmol) was added to a solution of 1-(1-(4-methoxyphenyl)-5-(p-tolyl)-1H-pyrazol-3-yl)-cyclohexan-cis-1,4-diyl diacetate (Intermediate 38) (297 mg, 0.642 mmol) in methanol (4.3 mL), and the resulting mixture was stirred at room temperature for 4 hours. Water was added to the reaction solution to stop the reaction, and the resulting solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain Intermediate 84 (213 mg, 0.507 mmol, 79%) as a white solid.

$^1$H-NMR (400 MHz, CDCl$_3$) δ: 1.49 (1H, d, J=4.4 Hz), 1.65-1.74 (2H, m), 1.90-1.98 (4H, m), 2.10 (3H, s), 2.32 (3H, s), 2.71-2.78 (2H, m), 3.74-3.81 (4H, m), 6.37 (1H, s), 6.83 (21-1, d, J=9.2 Hz), 7.08 (4H, s), 7.20 (2H, d, J=9.2 Hz).

ESI-MS: m/z=421 (M+H)$^+$

INDUSTRIAL APPLICABILITY

The cyclohexane derivatives or pharmaceutically acceptable salts thereof or prodrugs thereof can be utilized as a pharmaceutical, especially a therapeutic agent or prophylactic agent for Alzheimer's disease, comprising them as an effective ingredient.

The invention claimed is:

1. A method of treating Alzheimer's disease comprising administering a therapeutically effective amount of a cyclohexane derivative represented by the Formula (I):

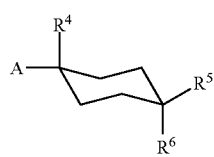

(I)

wherein

A is a substituent represented by the Formula (IIa) or (IIb):

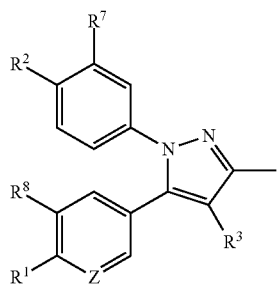

(IIa)

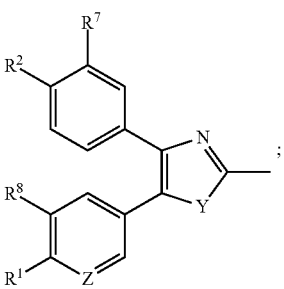

(IIb)

$R^1$ and $R^2$ are each independently a hydrogen atom, a chlorine atom, a $C_1$-$C_3$ haloalkyl group, a $C_1$-$C_4$ alkyl group or a $C_1$-$C_4$ alkoxy group;

$R^3$ is a hydrogen atom or a chlorine atom; $R^4$ is a fluorine atom, a hydroxymethyl group or a hydroxyl group;

$R^5$ and $R^6$ are each independently a hydrogen atom, a fluorine atom, a $C_1$-$C_3$ haloalkyl group, a carboxyl group, a methoxycarbonyl group, an ethoxycarbonyl group, a $C_1$-$C_4$ alkoxy group, a hydroxyl group or a $C_2$-$C_5$ alkylcarbonyloxy group, or optionally together form an oxo group;

$R^7$ and $R^8$ are each independently a hydrogen atom or a fluorine atom;

Y is an oxygen atom or a sulfur atom;

Z is a nitrogen atom or a methine group or a pharmaceutically acceptable salt thereof or a prodrug thereof.

2. The method according to claim 1, wherein $R^1$ and $R^2$ are each independently a trifluoromethyl group, a methyl group or a methoxy group.

3. The method according to claim 1, wherein $R^3$ is a hydrogen atom.

4. The method according to claim 1, wherein $R^4$ is a hydroxymethyl group or a hydroxyl group.

5. The method according to claim 1, wherein $R^5$ and $R^6$ are each independently a hydrogen atom, a fluorine atom, a trifluoromethyl group, a carboxyl group, a methoxy group, a hydroxyl group or an acetyloxy group, or optionally together form an oxo group.

6. The method according to claim 2, wherein $R^3$ is a hydrogen atom.

7. The method according to claim 2, wherein $R^4$ is a hydroxymethyl group or a hydroxyl group.

8. The method according to claim 3, wherein $R^4$ is a hydroxymethyl group or a hydroxyl group.

9. The method according to claim 2, wherein $R^5$ and $R^6$ are each independently a hydrogen atom, a fluorine atom, a trifluoromethyl group, a carboxyl group, a methoxy group, a hydroxyl group or an acetyloxy group, or optionally together form an oxo group.

10. The method according to claim 3, wherein $R^5$ and $R^6$ are each independently a hydrogen atom, a fluorine atom, a trifluoromethyl group, a carboxyl group, a methoxy group, a hydroxyl group or an acetyloxy group, or optionally together form an oxo group.

11. The method according to claim 4, wherein $R^5$ and $R^6$ are each independently a hydrogen atom, a fluorine atom, a trifluoromethyl group, a carboxyl group, a methoxy group, a hydroxyl group or an acetyloxy group, or optionally together form an oxo group.

* * * * *

UNITED STATES PATENT AND TRADEMARK OFFICE
CERTIFICATE OF CORRECTION

PATENT NO.        : 8,598,212 B2
APPLICATION NO.   : 13/643742
DATED             : December 3, 2013
INVENTOR(S)       : Nakao et al.

It is certified that error appears in the above-identified patent and that said Letters Patent is hereby corrected as shown below:

In the Specification

In Column 19

At line 15, please change "(II)" to -- (Ii) --.

Signed and Sealed this
Twenty-second Day of July, 2014

Michelle K. Lee
*Deputy Director of the United States Patent and Trademark Office*